United States Patent [19]
Pinney et al.

[11] Patent Number: 6,162,930
[45] Date of Patent: Dec. 19, 2000

[54] ANTI-MITOTIC AGENTS WHICH INHIBIT TUBULIN POLYMERIZATION

[75] Inventors: Kevin G. Pinney, Hewitt, Tex.; George R. Pettit, Paradise Valley, Ariz.; Vani P. Mocharla, Waco, Tex.; Maria del Pilar Mejia, Evanston, Ill.; Anupama Shirali, Pune, India

[73] Assignee: Baylor University, Waco, Tex.

[21] Appl. No.: 09/380,429

[22] PCT Filed: Mar. 6, 1998

[86] PCT No.: PCT/US98/04380

§ 371 Date: Dec. 3, 1999

§ 102(e) Date: Dec. 3, 1999

[87] PCT Pub. No.: WO98/39323

PCT Pub. Date: Sep. 11, 1998

[51] Int. Cl.[7] .............. C07D 333/56; C07D 333/52; C07C 41/00; C07C 49/115
[52] U.S. Cl. .............. 549/57; 549/58; 549/49; 568/632; 568/633; 568/327; 568/328; 514/443
[58] Field of Search .............. 549/57, 58, 49; 514/443; 568/632, 633, 327, 328

[56] References Cited

U.S. PATENT DOCUMENTS

| | | | |
|---|---|---|---|
| 5,886,025 | 3/1999 | Pinney | 514/443 |
| 6,030,986 | 2/2000 | Palkowitz | 514/324 |
| 6,040,309 | 3/2000 | Dack et al. | 514/253 |
| 6,048,875 | 4/2000 | De Manteuil et al. | 514/314 |
| 6,060,488 | 5/2000 | Dodge et al. | 514/324 |

*Primary Examiner*—Deborah C. Lambkin
*Attorney, Agent, or Firm*—Head, Johnson & Kachigian

[57] ABSTRACT

Methoxy and ethoxy substituted 3-aroyl-2-arylbenzo[b]thiophenes and benzo[b]thiophene analogues are described for use in inhibiting tubulin polymerization. The compounds' use for treating tumor cells is also described.

13 Claims, 16 Drawing Sheets

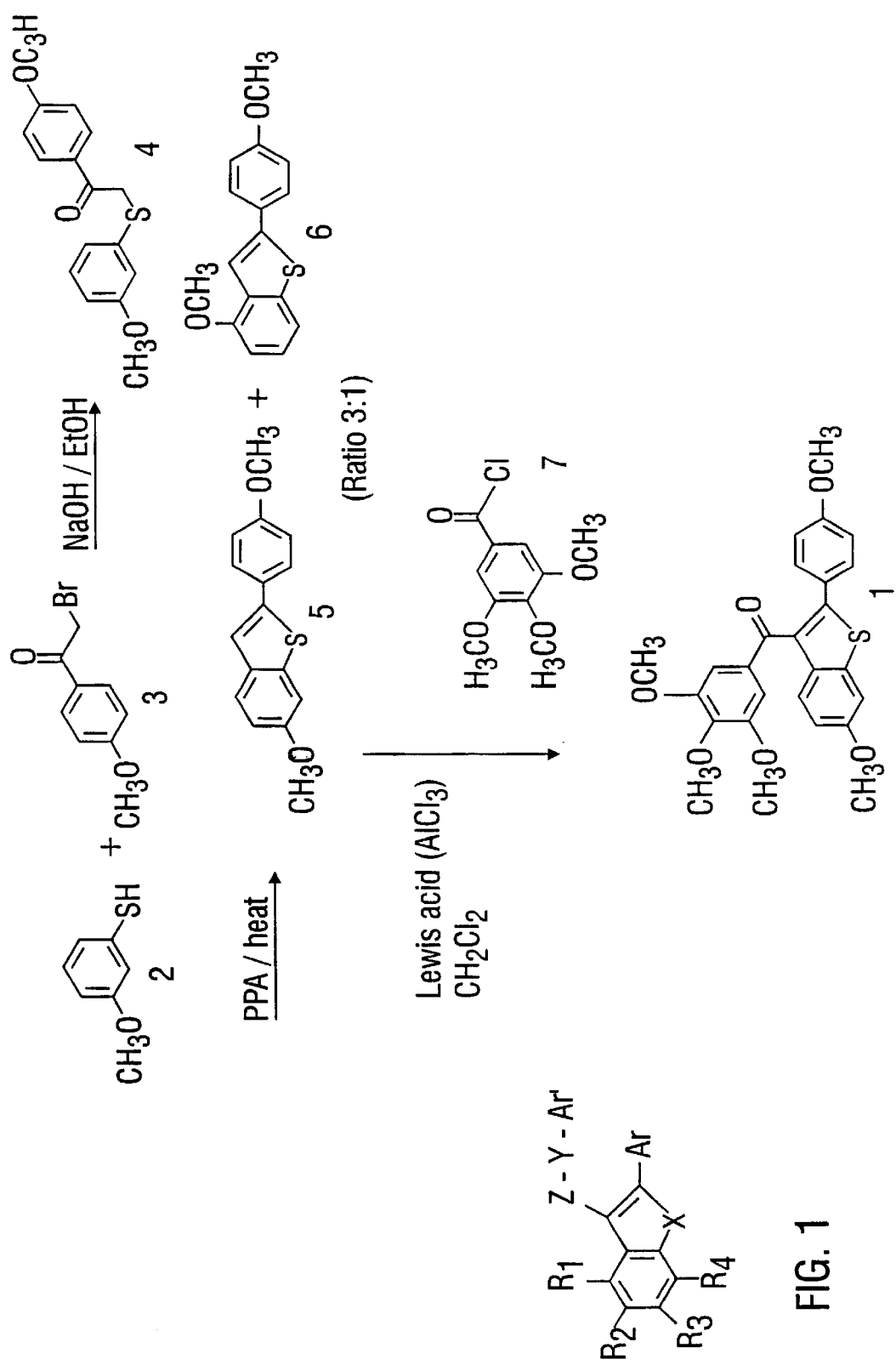

5A

6A

7A

8A

9A

10A

11A

12A

13A

14A

15A

16A

17A

18A

19A

20A

21A

22B

23B

24C

25D

26D

27E

28E

29E

30E

31E

32E

33E

34E

ANTI-MITOTIC AGENTS WHICH INHIBIT TUBULIN POLYMERIZATION

This application is a 371 of PCT/US98/04350 Mar. 6, 1998.

BACKGROUND OF THE INVENTION

1. Field of the Invention

The present invention relates generally to the field of tubulin polymerization inhibitors. More particularly, it concerns the use of 3-aroyl-2-aryl-benzo[b]thiophenes and analogues thereof as anti-tumor agents.

2. Description of Related Art

An aggressive chemotherapeutic strategy toward the treatment and maintenance of solid-tumor cancers continues to rely on the development of architecturally new and biologically more potent anti-tumor, anti-mitotic agents. A variety of clinically-promising compounds which demonstrate potent cytotoxic and anti-tumor activity are known to effect their primary mode of action through an efficient inhibition of tubulin polymerization (Gerwick et al.). This class of compounds undergoes an initial binding interaction to the ubiquitous protein tubulin which in turn arrests the ability of tubulin to polymerize into microtubules which are essential components for cell maintenance and cell division (Owellen et al.).

Currently the most recognized and clinically useful tubulin polymerization inhibitors for the treatment of cancer are vinblastine and vincristine (Lavielle, et al.). Additionally, the natural products rhizoxin (Nakada, et al., 1993a and 1993b; Boger et al.; Rao et al., 1992 and 1993; Kobayashi et al., 1992 and 1993) combretastatin A-4 and A-2 (Lin et al.; Pettit, et al., 1982, 1985, and 1987) and taxol (Kingston et al.; Schiff et al; Swindell, et a, 1991; Parness, et al.) as well as certain synthetic analogues including the 2-styrylquinazolin-4(3H)-ones (SQO) (Jiang et al.) and highly oxygenated derivatives of cis- and trans-stilbene (Cushman et al.) and dihydrostilbene are all known to mediate their cytotoxic activity through a binding interaction with tubulin. The exact nature of this interaction remains unknown and most likely varies somewhat between the series of compounds.

Tubulin is a heterodimer of the globular α and β tubulin subunits. A number of photoaffinity labeling reagents for tubulin have been developed and evaluated (Rao et al., 1992 and 1994; Chavan et al.; Sawada et al., 1991, 1993a and 1993b; Staretz et al.; Hahn et al; Wolff et al.; Floyd et al.; Safa et al.; Williams et al.). These reagents have identified three distinct small molecule binding sites on tubulin: the colchicine site, the vinblastine site and the maytansine/rhizoxin site. Additionally, a first generation rhizoxin-based photoaffinity labeling reagent has suggested binding to the Met-363-Lys-379 site on β-tubulin (Sawada et al., 1993a), and a taxol-based reagent has been found to label the N-terminal 31 amino acid residues of β-tubulin (Swindell et al, 1991 and 1994; Rao et al., 1994). Taxol itself is known to bind to polymerized microtubules, but not at distinct sites on the monomer subunits of tubulin (Kingston et al.; Schiff et al.; Swindell et al., 1991; Parness et al.).

The discovery of new antimitotic agents may result from the judicious combination of a molecular template which in appropriately substituted form (i.e. phenolic moieties, etc.) interacts with the estrogen receptor suitably modified with structural features deemed imperative for binding to the colchicine site on β-tubulin (arylalkoxy groups, certain halogen substitutions, pseudo aryl ring stacking, etc.). The methoxy aryl functionality seems especially important for increased interaction at the colchicine binding site in certain analogs. (Shirai et al., D'Amato et al., Hamel, 1996). Recent studies have shown that certain estrogen receptor (ER) binding compounds as structurally modified congeners (2-methoxyestradiol, for example) interact with tubulin and inhibit tubulin polymerization. (D'Amato et al., Cushman et al., 1995, Hamel, et al., 1996, Cushman et al., 1997). Estradiol is, of course, perhaps the most important estrogen in humans, and it is intriguing and instructive that the addition of the methoxy aryl motif to this compound makes it interactive with tubulin. As a steroid, however, the use of 2-methoxyestradiol as an anti-cancer agent may lead to unwanted side effects.

Even before the discovery and realization that molecular templates (of traditionally estrogen receptor active compounds) suitably modified with alkoxyaryl or other groups deemed necessary for tubulin binding often result in the formation of new classes of inhibitors of tubulin polymerization, antiestrogens were developed to treat hormone-dependent cancers and a number of nonsteroidal agents were developed. Tamoxifen, for instance, has been widely used to treat estrogen-dependent metastatic mammary carcinoma (Mouridsen, et al.). The structure of trioxifene mesylate, a tetralin based compound which exhibits anti-tumor effects at the same or higher level as tamoxifen (Jones et al., 1979), includes a ketone moiety as part of its triarylethylene core, thereby overcoming the isomerization tendencies of the ethylene double bond of this class of compounds, assuring the stability of the molecule's three-dimensional structure. Unfortunately, despite their antiestrogen properties, tamoxifen and the related triarylethylene derivatives retain some intrinsic estrogen agonist properties, reducing their ability to fully inhibit biological responses to exogenous or endogenous estrogens (Jones et al., 1984).

The benzo[b]thiophenes are another example of a class of compounds which often exhibit very high affinity for the estrogen receptor (Kym et al.; Pinney et al., 1991a and 1991b; WO 95/10513). The 2,3-diaryl substituted benzo[b]thiophenes greatly resemble the triarylethylene-based core structure of tamoxifen. The estrogenicity of the triarylethylene compounds has been shown to be substantially overcome in 3-aroyl-2-arylbenzo[b]thiophene compounds substituted at the 3-aroyl group with basic amine moieties (Jones et al., 1984). A prime example of this type of compound is LY117018 (U.S. Pat. No. 4,656,187). 3-aroyl-2-arylbenzo[b]thiophenes have also been found to be useful antifertility agents (U.S. Pat. No. 4,133,814) and as inhibitors for 5-lipoxygenase (U.S. Pat. No. 5,532,382).

SUMMARY OF THE INVENTION

The present invention provides benzo[b]thiophene-based inhibitors of tubulin polymerization, thereby providing novel anti-tumor compounds of increased cytotoxicity and fewer side effects. This is accomplished through the introduction of small alkoxy aryl substituents to the estrogenic benzo[b]thiophene skeleton or the skeleton of compounds similar to benzo[b]thiophene, such as indene, benzofuran, and indole. The tubulin polymerization inhibitors of this invention are illustrated by the structure:

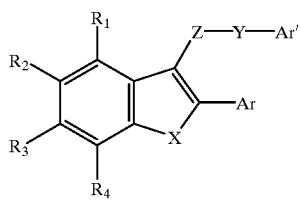

wherein

X is S, O, NH, or CH$_2$,

R$_1$–R$_4$ are independently chosen from the group including H, OH and C$_1$–C$_5$ alkoxy, Z is C=O, CH$_2$, C$_2$H$_2$, CHOH, or CHOCH$_3$, Y is a covalent bond, CH$_2$, or CH$_2$CH$_2$ Ar and Ar' are aryl moieties, chosen from the group consisting of phenyl and napthyl, wherein each aryl group is further substituted with at least one C$_1$–C$_5$ alkoxy group.

Preferably, the tubulin polymerization inhibitors of this invention will be of the above formula wherein X is S. The most preferred R group substitution pattern will be wherein R$_3$ is OCH$_3$ and R$_1$, R$_2$ and R$_4$ are H. Z will preferably be C=O, Y will preferably be a covalent bond, and Ar will preferably be 4-methoxyphenyl. The most preferred Ar' groups will be singly and multiply substituted phenyl groups containing para ethoxy or methoxy substituents. The most preferred tubulin polymerization inhibitor of this invention is 3-(3',4',5'-trimethoxybenzoyl)-2-(4'-methoxyphenyl)-6-methoxybenzo[b]-thiophene.

The term "C$_1$–C$_5$ alkoxy" as used herein contemplates both straight chain and branched chain alkyl radicals and therefore defines groups such as, for example, methoxy, ethoxy, n-propoxy, isopropoxy, n-butyloxy, isobutyloxy, tert-butyloxy, sec-butyloxy, pentyloxy, isopentyloxy, t-pentyloxy, neopentyloxy, and the like. The preferred alkoxy groups are methoxy and ethoxy.

The novel compounds of this invention are of the structure:

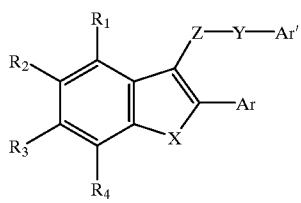

wherein

X is S, O, NH, or CH$_2$,

R$_1$–R$_4$ are independently chosen from the group including H, OH and C$_1$–C$_5$ alkoxy, Z is C=O, CH$_2$, C$_2$H$_2$, CHOH, or CHOCH$_3$, Y is a covalent bond, CH$_2$, or CH$_2$CH$_2$, Ar and Ar' are aryl moieties, chosen from the group containing phenyl and napthyl, each aryl group substituted with at least one C$_1$–C$_5$ alkoxy group; wherein when Ar' is 3,4,5-trimethoxyphenyl or 4-methoxyphenyl, X is S, Z is C=O, Y is a covalent bond, R$_3$ is OCH$_3$, R$_1$, R$_2$, and R$_4$ are H, and Ar is a phenyl group that contains at least one methoxy substituent, then Ar must be substituted with a total of at least two alkoxy groups.

The preferred novel compounds of this invention will be those wherein X is S, Z is C=O, R$_3$ is methoxy and Ar is 4-methoxyphenyl. The preferred novel compounds of this invention include:

3-(2',6'-dimethoxybenzoyl)-2-(4'-methoxyphenyl)-6-methoxybenzo[b]thiophene, 3-(3',5'-dimethoxybenzoyl)-2-(4'-methoxyphenyl)-6-methoxybenzo[b]thiophene, 3-(3',4'-dimethoxybenzoyl)-2-(4'-methoxyphenyl)-6-methoxybenzo[b]thiophene, 3-(4'-ethoxybenzoyl)-2-(4'-methoxyphenyl)-6-methoxybenzo[b]thiophene, 3-(3',4',5'-triethoxybenzoyl)-2-(4'-methoxyphenyl)-6-methoxybenzo[b]-thiophene, and 3-[3'-(3",4",5"-trimethoxyphenyl)propanoyl]-2-(4'-methoxyphenyl)-6-methoxybenzo[b]thiophene.

The most preferred novel compounds of this invention will be those wherein X is S, Z is C=O, Ar is 4-methoxyphenyl, R$_3$ is methoxy, and Ar' is a phenyl group substituted with an alkoxy group at the para position. The most preferred novel compounds of this invention include:

3-(3',4'-dimethoxybenzoyl)-2-(4'-methoxyphenyl)-6-methoxybenzo[b]thiophene, 3-(4'-ethoxybenzoyl)-2-(4'-methoxyphenyl)-6-methoxybenzo[b]thiophene, 3-(3',4',5'-triethoxybenzoyl)-2-(4'-methoxyphenyl)-6-methoxybenzo[b]-thiophene, and 3-[3'-(3",4",5"-trimethoxyphenyl)propanoyl]-2-(4'-methoxyphenyl)-6-methoxybenzo[b]thiophene.

As a preferred embodiment of the invention, the tubulin polymerization inhibitors will be used as part of pharmacologically active compositions for treating leukemias, melanomas, and colon, lung, ovarian, CNS, and renal cancers, as well as other cancers. In the most preferred embodiment of this aspect of the invention, the tubulin polymerization inhibitors will be used to treat colon cancers.

As a further preferred embodiment, the tubulin polymerization inhibitors of this invention may be used to treat any disease for which tubulin polymerization plays a crucial role. In addition to anti-tumor activity, caused by lack of mitosis in cells in which tubulin polymerization is absent, the tubulin polymerization inhibitors of this invention would also be useful in treating diseases caused by flagellated parasites, for whom tubulin polymerization is crucial to movement. In particular, the tubulin polymerization inhibitors of this invention will be useful in treating Chagas' disease or diseases caused by the parasite Leishmania.

The present invention also includes a compound of the structure

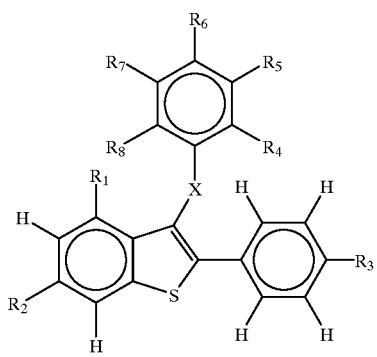

where R$_1$ is H or CH$_3$O; R$_2$ is H, CH$_3$O or C$_2$H$_5$O; R$_3$ is CH$_3$O or C$_2$H$_5$O; R$_4$, R$_5$, R$_7$ and R$_8$ are independently H, $CH_3O$, $C_2H_5O$, or F; $R_6$ is H, $CH_3O$, $C_2H_5O$, OH, F or $N(CH_3)_2$; and X is

The present invention also includes a compound of the structure

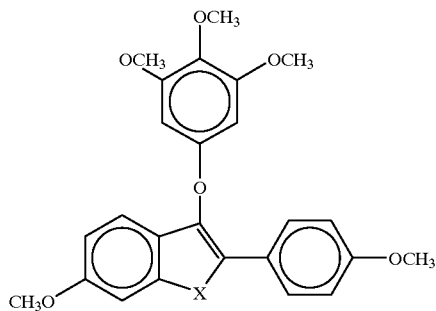

where X is S or S=O.
Also included is a compound of the structure

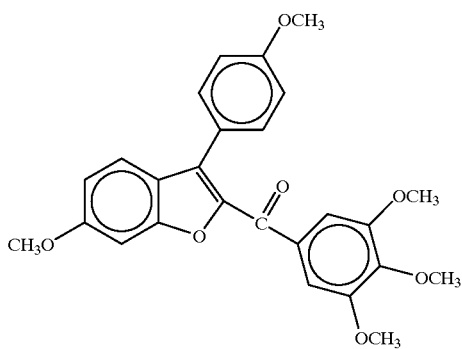

as well as a compound of the structure

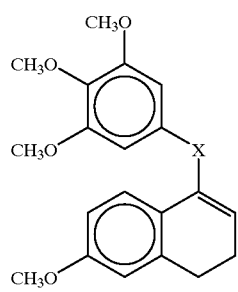

where X is CHOH or C=O. A compound of the following structure is also included in the present invention

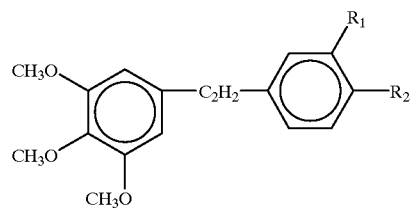

where $R_1$ and $R_2$ are independently $CH_3O$, $NO_2$, $NH_2$ or $N_3$ and $CH_3O$; and $C_2H_2$ is in the E or Z configuration; with the proviso that one of $R_1$ and $R_2$ is $CH_3O$ and the other is $NO_2$, NH, or $N_3$.

One preferred embodiment is where $C_2H_2$ is E $C_2H_2$, $R_1$ is $CH_3O$ and $R_2$ is $NH_2$ in the immediately prior structure. Another embodiment is where $C_2H_2$ is E $C_2H_2$, $R_1$ is $NH_2$ and $R_2$ is $CH_3O$ in the immediately prior structure. Yet another embodiment is where $C_2H_2$ is Z $C_2H_5$, $R_1$ is $CH_3O$ and $R_2$ is $NH_2$ in the immediately prior structure. Another embodiment is where $C_2H_2$ is Z $C_2H_2$, $R_1$ is $NH_2$ and $R_2$ is $CH_3O$ in the immediately prior structure. Another embodiment is where $C_2H_2$ is E $C_2H_2$, $R_1$ is $CH_3O$ and $R_2$ is $NO_2$ in the immediately prior structure. In another embodiment $C_2H_2$ is E $C_2H_2$, $R_1$ is $NO_2$ and $R_2$ is $CH_3O$ in the immediately prior structure.

One preferred embodiment of the present invention is where $C_2H_2$ is Z $C_2H_5$, $R_1$ is $CH_3O$ and $R_2$ is $NO_2$ in the immediately prior structure.

One embodiment is where $C_2H_2$ is Z $C_2H_2$, $R_1$ is $NO_2$ and $R_2$ is $CH_3O$ in the immediately prior structure.

Yet another embodiment is where $C_2H_2$ is E $C_2H_2$, $R_1$ is $CH_3O$ and $R_2$ is $N_3$ in the immediately prior structure. A preferred embodiment also is where $C_2H_2$ is E $C_2H_2$, $R_1$ is $N_3$ and $R_2$ is $CH_3O$ in the immediately prior structure. Also preferred is the compound where $C_2H_2$ is Z $C_2H_5$, $R_1$ is $CH_3O$ and $R_2$ is $N_3$ in the immediately prior structure. Another embodiment described is where $C_2H_2$ is Z $C_2H_2$, $R_1$ is $N_3$ and $R_2$ is $CH_3O$ in the immediately prior structure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the general structure of certain tubulin polymerization inhibitor compounds.

FIG. 4 shows a general scheme for the synthesis of the 3-aroyl-2-phenybenzo[b]thiophene compounds.

DESCRIPTION OF ILLUSTRATIVE EMBODIMENTS

Figure 2A:
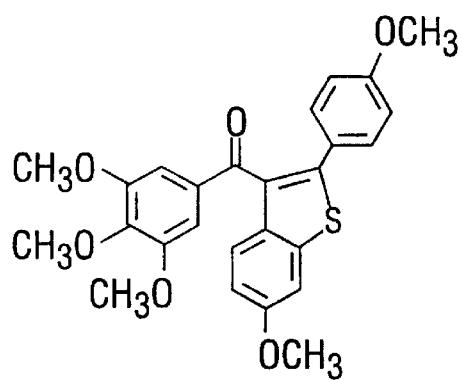
FIG. 2 shows the pseudo-cis (FIG. 2A) and pseudo-trans (FIG. 2B) orientations of 3-aroyl-benzo[b]thiophene compounds and the structure of Combretastatin A-4 (FIG. 2C).

The present example relates to the inventors' discovery that certain compounds described herein, including 3-(3'4'5'-trimethoxybenzoyl)-2-(4'-methoxyphenyl)-6-methoxybenzo[b]thiophene, inhibit tubulin polymerization and inhibit tumor cell population to nearly the same extent as Combretastatin A-4, one of the most potent inhibitors known. The tubulin polymerization $IC_{50}$ of the methoxyaroyl-substituted benzo[b]thiophene, for example, was 1.5–2.5 $\mu$M while that of Combretastatin A-4 was 0.75 $\mu$M. 3-(3'4'5'-trimethoxybenzoyl)-2-(4'-methoxyphenyl)-6-methoxybenzo[b]thiophene and other examples also showed significant cell growth inhibitory activity against the growth of several tumor cell lines. The compounds were particularly effective against the colon KM20L2 cell line, exhibiting a $GI_{50}$ of $4.9 \times 10^{-2}$ $\mu$g/ml or less.

The molecular structure of certain tubulin polymerization inhibitors of the present invention are based on the structure of benzo[b]thiophene and the similar structures of indole, benzofuran and indene (FIG. 1). The six-membered ring of these fused systems is substituted by one or more hydroxy or alkoxy groups, in any substitution pattern. C-2 of the benzo[b]thiophene, benzofuran or indole or C-3 of the indene is substituted with an aromatic moiety, preferably phenyl. This aromatic substituent will also contain one or more alkoxy substituents. Although it is unlikely that this group will interact at the colchicine binding site of tubulin, elaboration of the molecules at this site may provide interactions with other small molecule binding sites on tubulin. C-3 of the benzo[b]thiophene, indole, or benzofuran and C-2 of the indene is also substituted with an alkoxy-substituted aryl moiety, and will contain a linker group connecting the parent benzo[b]thiophene, benzofuran, indole, or indene structure and the aromatic substituent. The linker group is of between one and three carbons, and may or may not contain a carbonyl functionality or another oxygen-containing group, such as alpoxy such as methoxy or ethoxy, e.g. Possible linker groups include C=O, $CH_2$, $C_2H_2$, $C_2H_4$, $C_3H_6$, CHOH, $CHOCH_3$, C(=O)$CH_2$, CH(OCH$_3$)CH$_2$, CH(OH)CH$_2$, C(=O)CH$_2$CH$_2$, C(OCH$_3$)CH$_2$CH$_2$, and C(OH)CH$_2$CH$_2$.

The design of this new class of benzo[b]thiophene-based and related molecules takes advantage of the known estrogenicity of the benzo[b]thiophenes (Jones et al., 1984) and combines this trait with alkoxy substitution of the aryl rings, a factor recently discovered to be important in tubulin binding (Shirai, et al., D'Amato et al.) The 3-aroyl substituent of many of these new compounds is particularly useful because the carbonyl moiety, by forcing the adjoining atoms into or nearly into planarity, serves to reduce the number of three-dimensional configurations available to the substituted benzothiophene. Recent studies have shown that less flexible ligands, although they may bind to fewer molecules, generally have higher binding affinities. More flexible molecules, on the other hand, are less discriminatory in finding a binding partner, but usually bind with lower affinity (Eaton et al.).

Figure 2B:
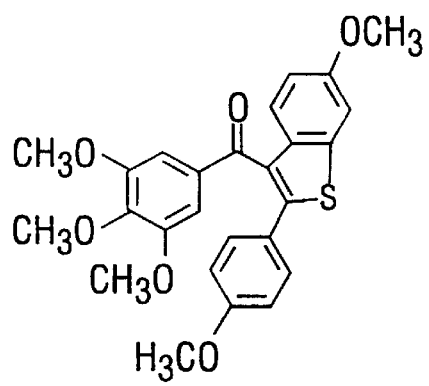
Figure 2C:
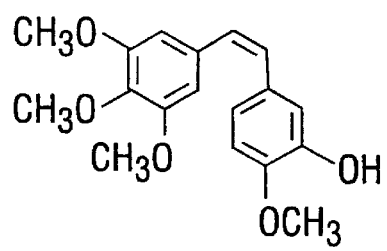
Figure 3A:
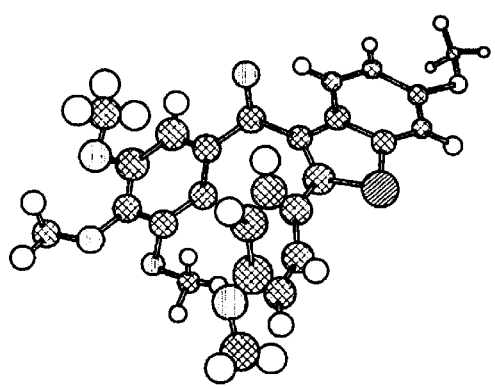
FIG. 3 shows the X-ray crystal structure of 3-(3',4',5'-trimethoxybenzoyl)-2-(4'-methoxyphenyl)-6-methoxybenzo[b]thiophene (FIG. 3A) and the energy minimized (MM2) structure of Combretastatin A-4 (FIG. 3B).
Figure 3B:
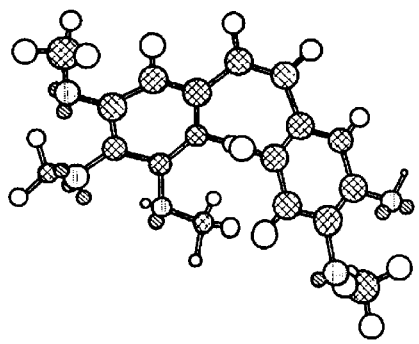

The most likely configurations for the 3-aroylbenzo[b] thiophenes is either the pseudo-cis configuration (FIG. 2A) or the pseudo-trans configuration (FIG. 2B). It is well know that the cis or Z form of the stilbenoid Combretastatin A-4 (FIG. 2C) has a much higher binding affinity for tubulin as compared to its trans or E counterpart (Cushman et al.). As shown in FIG. 2, both the pseudo-cis and pseudo-trans configurations of the aroyl benzo[b]thiophenes retain a great deal of structural overlap with the cis conformation of Combretastatin A-4. Recently, the X-ray crystal structures of 3-(3',4',5'-trimethoxybenzoyl)-2-(4'-methoxyphenyl)-6-methoxybenzo[b]thiophene and other 3-aroyl-2-phenylbenzo[b]thiophenes were solved and show that the preferred conformation of the 3-aroylbenzo[b]thiophene compounds is indeed the pseudo-trans configuration (Mullica et al.). The X-ray crystal structure of 3-(3',4',5'-trimethoxybenzoyl)-2-(4'-methoxyphenyl)-6-methoxybenzo[b]thiophene and the computationally minimized (MM2) structure of Combretastatin A-4 are shown for comparison in FIG. 3.

A typical synthesis of the benzo[b]thiophene compounds is shown in FIG. 4 for 3-(3',4',5'-trimethoxybenzoyl)-2-(4'-methoxyphenyl)-6-methoxybenzo[b]thiophene 1. Intermediate 5, 6-methoxy-2-(4'-methoxyphenyl)-benzo[b] thiophene, was prepared from 3-methoxybenzene thiol 2 and bromoacetotophenone 3 according to the method of Kost et al. The polyphosphoric acid (PPA) catalyzed cyclization of the substituted thiol 4 produced regioisomers 5 and 6 in a 3:1 ratio separable due to differences in the molecules' solubility (e.g., in acetone). The use of other thiols and acyl halides can allow for alternative substitution patterns on the benzene ring of the benzo[b]thiophene and the C-2 substituent aryl group. Alternatively, phenols or anilines may be used in place of the thiol to produce benzofurans or indoles. Friedel-Crafts aroylation of 5 results in functionalization at C-3 of the benzo[b]thiophene skeleton, giving the 3-aroyl-2-phenylbenzo[b]thiophene 1. By a similar scheme, Friedel-Crafts alkylation of 6-methoxy-2-(4'-methoxyphenyl)benzo [b]thiophene provides a route to the benzyl and phenylethyl substituted benzo[b]thiophenes, while reduction of the aroyl carbonyl can lead to the hydroxybenzyl compounds. Suitable reduction agents include lithium aluminum hydride and sodium borohydride. The hydroxy compounds can be further elaborated with the addition of alkoxy substituents through a variety of nucleophilic substitution reactions. For example, deprotonation of the benzylic alcohol formed from reduction of compound 1, followed by reaction with an alkyl halide could be used to form a benzylic ether. In addition, dehydration of a CH(OH)CH$_2$ or a CH(OH)CH$_2$CH$_2$ linker group would lead to linker groups containing double bonds. The indenes of this invention could be made by a different route, involving treatment of the proper 1-indanone with tosyl hydrazine followed by a modified Shapiro reaction with the resulting hydrazone to complete attachment of the alkoxy-substituted benzoyl moiety. An organocuprate 1,4 addition to the resultant α,β-unsaturated ketone will effect suitable attachment of the additional aryl group, while treatment with phenylselenium chloride, followed by oxidation and elimination would regenerate the indene double bond, completing the synthesis.

The ability of the various above described compounds to inhibit tubulin polymerization can be determined by in vitro assay. A suitable assay system is that described by Bai et al. A method for purifying tubulin from bovine brain cells is described by Hamel and Lin. The IC$_{50}$ values for tubulin polymerization determined for some of the compounds of this invention demonstrate the importance of the alkoxy substituent at the para position of the 3-aroyl phenyl group. As described above, the IC$_{50}$ of 3-(3',4',5'-trimethoxybenzoyl)-2-(4'-methoxyphenyl)-6-methoxybenzo[b]thiophene is comparable to that of Combretastatin A-4. Otherwise identical 3,5-dimethoxybenzoyl, 2,6-dimethoxybenzoyl and 3,5-dimethoxy-4-hydroxybenzoyl compounds showed no observable tubulin polymerization inhibition activity. It is contemplated, however, that any novel benzo[b]thiophene compounds of this invention that do not inhibit tubulin polymerization may still be useful based upon their inherent estrogenicity, for example, as anti-fertility theraputics.

A measurement of each compound's tubulin affinity may also be determined through the compound's ability to inhibit colchichine-tubulin binding. A suitable assay is that described by Kang et al., involving the use of commercially available tritiated colchicine. Decreases in the amount of [$^3$H]colchicine-tubulin interaction due to the competitive binding of one of the novel inhibitors of this invention may be measured by autoradiography or scintillation counting.

The tubulin polymerization compounds can also be tested for their ability to inhibit tumor cell growth. Initially, cytotoxicity of the various compounds may be measured against the leukemia P388 cell line or other appropriate cell lines in vitro to determine which compounds will be most effective against each type of tumor cell. As in the tubulin polymerization assays, the para methoxy substituent of the 3-aroyl phenyl group was very important in producing cytotoxic activity against P388 leukemia cells. Significantly, the compounds that failed to inhibit tubulin polymerization, the 3,5-dimethoxybenzoyl, 2,6-dimethoxybenzoyl and the 3,5-dimethoxy-4-hydroxybenzoyl compounds also failed to show measurable activity against the leukemia cells. Another significant finding was that 3-(3',4',5'-trimethoxybenzoyl)-2-(4'-methoxyphenyl)-6-methoxybenzo[b]thiophene had a smaller ED$_{50}$ value than a nitrogen derivative of combretastatin, 5-[(Z)-2-(3',4',5'-trimethoxyphenyl)ethenyl]-2-methoxy-N,N-bis-(phenylmethyl)aniline. The in vitro activities of 3-(3',4',5'-trimethoxybenzoyl)-2-(4'-methoxyphenyl)-6-methoxybenzo[b]thiophene against other cell lines are listed in Table 1 of Example 4 below.

As will be obvious to one of skill in the art, tubulin polymerization plays a role in diseases other than cancer. Chagas' disease, for example, is caused by *Trypanosoma cruzi*, a flagellate protozoa which has a substantial protein composition containing tubulin both as a component of the subpellicular microtubule system and the flagellum (De Souza). Chagas' disease is characterized by lesions in the heart, alimentary tract and nervous system. The disease currently affects approximately 16–18 million people and is the leading cause of myocarditis in the Americas (WHO). Inhibition of tubulin polymerization, crucial to the parasite's mobility, would provide an effective treatment. Indeed, the use of agents that selectively affect tubulin polymerization has precedence in the therapy of other parasitic diseases. The benzimidazoles are very effective anti-helmenthic drugs (Katiyar, et al.), and the dinitroanilines have shown promise against Leishmania, a parasite closely related to Trypanosoma (Chan and Gong). Currently, only two drugs exist for the treatment of Chagas' disease: benznidazole and nifurtimox. Both of these compounds are nitroheterocycles that are converted into nitro anion radicals that then interfere with macromolecular synthesis. These drugs have several adverse effects, including thrombocytopenic purpura and polyneropathy. These compounds may also cause genotoxicity in children (Marr et al., De Castro). A suitable assay for determining the tubulin polymerization inhibitors ability to treat parasites is described by Maldonado et al.

For their use in treating disease, the tubulin polymerization inhibitors may be present as part of pharmacologically active compositions suitable for the treatment of animals, particularly humans. The tubulin polymerization inhibitor or tubulin polymerization inhibitor-containing composition must then contact the tubulin-containing system wherein tubulin polymerization needs to be inhibited, for example, the tumor cells or the cells of the flagellate parasite. Pharmacologically active compositions of the tubulin polymerization inhibitors can be introduced via intravenous injection or orally in solid formulations such as tablets, chewable tablets or capsules. The preparation may also be a parenteral preparation for injection directly at the site of the tumor or parasitic infection.

The preferred dosage of the active ingredient inhibitor compound will vary depending upon the size and type of tumor or degree of parasitic infection, the patient's weight and age, and the exact identity of the tubulin polymerization inhibitor employed. The number of administrations of the pharmaceutically active composition will also vary according to the response of the individual patient to the treatment. For the treatment of cancer, suitable dosages of the tubulin polymerization inhibitors occur in amounts between 0.5 mg/kg of body weight to 100 mg/kg of body weight per day, preferably of between 1.0 mg/kg of body weight to about 20 mg/kg of body weight. It is contemplated that a similar dosage range would be suitable for the treatment of parasitic infections. Moreover, tubulin inhibition assays can also provide one of skill in the art with the appropriate concentrations of inhibitors that must reach the tubulin-containing cells, and the appropriate dosage can be calculated from that information.

The preparations of tubulin polymerization inhibitors may require the use of suitable pharmaceutically acceptable carriers. As used herein, "pharmaceutically acceptable carrier" includes any and all solvents, dispersion media, coatings, antibacterial and antifungal agents and isotonic agents and the like. The use of such media and agents for pharmaceutically active substances is well known in the art. Except insofar as any conventional media or agent is incompatible with the active ingredient, its use in the therapeutic composition is contemplated. Supplementary active ingredients can also be incorporated into the compositions. The phrase 'pharmaceutically acceptable" also refers to molecular entities and compositions that do not produce an allergic or similar untoward reaction when administered to an animal or a human.

The following examples are included to demonstrate preferred embodiments and best modes of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

BENZO[b]THIOPHENES

Synthesis of 3-(3',4',5'-trimethoxybenzoyl)-2-(4'-methoxyphenyl)-6-methoxy-benzo[b]thiophene (Compound 1 1and 1A)

2-(4'-methoxyphenyl)-6-methoxybenzo[b]thiophene was prepared according to the procedure of Kost et al. To a well-stirred solution of 5 (0.500 g, 1.85 mmol) and 3,4,5-trimethoxybenzoyl chloride (0.640 g, 2.77 mmol) in $CH_2Cl_2$ (20 ml), was added $AlCl_3$ (0.123 g, 0.925 mmol) portion-wise over a 15 minute period. After 5 hours (total reaction time), water was added, and the product was isolated initially by extraction with $CH_2Cl_2$ and subsequently by extraction with ethyl acetate (EtOAc). The organic layers were separately washed with brine and then combined and dried over $MgSO_4$. Purification by flash chromatography (silica gel, 60:40 EtOAc/hexane) afforded 3-(3',4',5'-trimethoxybenzoyl)-2-(4'-methoxyphenyl)-6-methoxybenzo[b]thiophene (0.537 g, 1.16 mmol, 63%) as an off-white solid. Recrystallization (hexane/ethanol) afforded a highly pure crystalline sample of the compound with mp 131–133° C. $^1$H-NMR ($CDCl_3$, 360 Mhz): δ=7.66 (d, J=8.9 Hz, 1H, ArH), 7.32 (d, J=2.4 Hz, 1H, ArH), 7.31 (d, J=8.8 Hz, 2H, ArH), 7.07 (s, 2H, ArH), 7.01 (dd, J=8.9, 2.4 Hz, 1H, ArH), 6.75 (d, J=8.8 Hz, 2H, ArH), 3.89 (s, 3H, —$OCH_3$), 3.83 (s, 3H, —$OCH_3$), 3.74 (s, 3H, —$OCH_3$), 3.73 (s, 6H, —$OCH_3$); $^{13}$C-NMR ($CDCl_3$, 90 Mhz): δ=192.9, 159.9, 157.7, 152.7, 143.7, 142.6, 140.1, 133.9, 132.3, 130.3, 129.9, 126.1, 124.2, 114.9, 114.1, 107.5, 104.4, 60.8, 56.1, 55.6, 55.2. HRMS (EI) $M^+$ calcd for $C_{26}H_{24}O_6S$ 464.1294, found 464.1294. Anal. Calcd for $C_{26}H_{24}O_6S$: C, 67.23; H, 5.21; S, 6.90. Found: C, 67.20; H, 5.26; S, 6.88.

Synthesis of 3-(2', 6'-dimethoxybenzoyl)-2-(4'-methoxyphenyl)-6-methoxybenzo[b]thiophene To a well-stirred solution of 2-(4'-methoxyphenyl)-6-methoxybenzo[b]thiophene (0.500 g, 1.85 mmol) and 2,6-dimethoxybenzoyl chloride (1.11 g, 5.56 mmol) in $CH_2Cl_2$ (40 mL) was added $AlCl_3$ (0.986 g, 7.40 mmol) portion-wise over a 15 minute period. After 6 hours, water was added, and the product was isolated initially by extraction with $CH_2Cl_2$ and subsequently by extraction with EtOAc. The organic layers were separately washed with brine and then combined and dried over $MgSO_4$. Purification by flash chromatography (silica gel, 60:40 EtOAc/hexane) afforded the title compound (0.484 g, 1.11 mmol, 60%) as an off-white solid. Recrystallization (hexane/ethanol) afforded a highly pure, crystalline sample with mp 146–152° C.: $^1$H-NMR ($CDCl_3$, 360 Mhz): δ=8.54 (dd, J=9.1, 0.3 Hz, 1H, ArH), 7.25 (d, J=2.1 Hz, 1H, ArH), 7.12 (d, J=8.8 Hz, 2H, ArH), 7.10 (dd, J=9.0, 2.5 Hz, 1H, ArH), 6.98 (t, J=8.4 Hz, 1H, ArH), 6.58 (d, J=8.8 Hz, 2H, ArH), 6.20 (d, J=8.4 Hz, 2H, ArH), 3.88 (s, 3H, —$OCH_3$), 3.73 (s, 3H, —$OCH_3$), 3.60 (s, 6H, —$OCH_3$); $^{13}$C-NMR ($CDCl_3$, 90 Mhz): δ=190.3, 159.5, 157.3, 157.3, 151.3, 139.3, 132.9, 131.9, 130.8, 130.5, 126.4, 125.7, 120.3 115.0, 112.6, 103.9, 103.6, 55.6, 55.5, 55.3. HRMS (EI) $M^+$ calcd for $C_{25}H_{22}O_5S$ 434.1188, found 434.1188. Anal. Calcd for $C_{25}H_{22}O_5S$: C, 69.11; H, 5.10; S, 7.38. Found: C, 69.19; H, 5.18; S, 7.28.

Synthesis of 3-(3', 5'-dimethoxybenzoyl)-2-(4'-methoxyphenyl)-6-methoxybenzo[b]thiophene To a well-stirred solution of 2-(4'-methoxyphenyl)-6-methoxybenzo[b]thiophene (0.615 g, 2.27 mmol) and 3,5-dimethoxybenzoyl chloride (1.37 g, 6.83 mmol) in $CH_2Cl_2$ (45 mL) was added $AlCl_3$ (1.21 g, 9.09 mmol) portion-wise over a 15 minute period. After 17 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 60:40 EtOAc/hexane) afforded the title compound (0.475 g, 1.09 mmol, 48%) as an off-white solid. Recrystallization (hexane/ethanol) afforded a highly pure, crystalline sample with mp 114–120° C.: $^1$H-NMR (CDCl$_3$, 360 Mhz): δ=7.59 (d, J=8.9 Hz, 1H, ArH), 7.32 (d, J=8.5 Hz, 2H, ArH), 7.32 (d, J=2.4 Hz, 1H, ArH), 6.98 (dd, J=9.0, 2.4 Hz, 1H, ArH), 6.94 (d, J=2.1 Hz, 2H, ArH), 6.76 (d, J=8.7 Hz, 2H, ArH), 6.52 (t, J=2.4 Hz, 1H, ArH), 3.89 (s, 3H, —OCH$_3$), 3.76 (s, 3H, —OCH$_3$), 3.71 (s, 6H, —OCH$_3$); $^{13}$C-NMR (CDCl$_3$, 90 Mhz): δ=194.0, 160.5, 159.8, 157.7, 143.9, 140.0, 139.3, 133.8, 130.3, 130.1, 126.0, 124.1, 114.9, 114.0, 107.6, 106.1, 104.4, 55.6, 55.5, 55.2. HRMS (EI) M$^+$ calcd for C$_{25}$H$_{22}$O$_5$S 434.1188, found 434.1245. Anal. Calcd. for C$_{25}$H$_{22}$O$_5$S: C, 69.11; H, 5.10; S, 7.38. Found: C, 69.00; H, 5.16; S, 7.34.

Synthesis of 3-(3', 4'-dimethoxybenzoyl)-2-(4'-methoxyphenyl)-6-methoxybenzo[b]thiophene To a well stirred solution of 2-(4'-methoxyphenyl)-6-methoxybenzo[b]thiophene (0.327 g, 1.21 mmol) and 3,4-dimethoxybenzoyl chloride (0.557 g, 2.77 mmol) in CH$_2$Cl$_2$ (20 ml) was added AlCl$_3$ (0.616 g, 4.62 mmol) portion-wise over a 15 minute period. After 7 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 60:40 Et$_2$O/hexanes) afforded the title compound (0.402 g, 0.92 mmol, 76%) as a pale yellow solid.

Synthesis of 3-(4'-methoxybenzoyl)-2-(4'-methoxyphenyl)-6-methoxybenzo[b]-thiophene To a well stirred solution of 2-(4'-methoxyphenyl)-6-methoxybenzo[b]thiophene (0.305 g, 1.13 mmol) and 4-methoxybenzoyl chloride (0.378 g, 2.22 mmol) in CH$_2$Cl$_2$ (45 ml) was added AlCl$_3$ (0.550 g, 4.12 mmol) portion-wise over a 15 minute period. After 1.3 hours, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.3576 g, 0.88 mmol, 78%) as a pale yellow solid. Recrystallization (EtOAc/hexanes) afforded a highly pure, crystalline sample with mp 119–120° C. $^1$H-NMR (CDCl$_3$, 360 MHz): δ=7.77 (d, J=9.0 Hz, 2H, ArH), 7.52 (d, J=8.9 Hz, 1H, ArH), 7.35 (d, J=8.9 Hz, 2H, ArH), 7.31 (d, J=2.3 Hz, 1H, ArH), 6.95 (dd, J=8.9, 2.4 Hz, 1H, ArH), 6.76 (d, J=9.0, 2H, ArH), 6.75 (d, J=8.9 Hz, 2H, ArH), 3.87 (s, 3H, —OCH$_3$), 3.79 (s, 3H, —OCH$_3$), 3.74 (s, 3H, —OCH$_3$); $^{13}$C-NMR (CDCl$_3$, 90 MHz): δ=193.2, 193.7, 159.7, 157.6, 142.4, 140.0, 134.0, 132.2, 130.5, 130.4, 130.2, 126.0, 124.0, 114.7, 114.0, 113.6, 104.5, 55.6, 55.4, 55.2. HRMS (EI) M$^+$ calcd for C$_{24}$H$_{20}$O$_4$S, 404.1082, found 404.1059. Anal. Calcd for C$_{24}$H$_{20}$O$_4$S: C, 71.27; H, 4.98; S, 7.93. Found: C, 71.39; H, 4.98; S, 7.90.

Synthesis of 3-(4'-ethoxybenzoyl)-2-(4'-methoxyphenyl)-6-methoxybenzo[b]-thiophene To a well stirred solution of 2-(4'-methoxyphenyl)-6-methoxybenzo[b]thiophene (0.300 g, 1.11 mmol) and 4-ethoxybenzoyl chloride (0.555 g, 3.01 mmol) in CH$_2$Cl$_2$ (45 ml) was added AlCl$_3$ (0.502 g, 3.76 mmol) portion-wise over a 15 minute period. After 45 minutes, water was added, and the product was isolated initially by extraction with CH$_2$Cl$_{12}$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.389 g, 0.93 mmol, 84%) as a white solid. Recrystallization (EtOAc/hexanes) afforded a highly pure, crystalline sample with mp 124–125° C. $^1$H-NMR (CDCl$_3$, 360 MHz): δ=7.77 (d, J=8.9 Hz, 2H, ArH), 7.52 (d, J=8.9 Hz, 1 Hz, ArH), 7.35 (d, J=8.8 Hz, 2H, ArH), 7.31 (d, J=2.4 Hz, 1H, ArH), 6.95 (dd, J=8.9, 2.4 Hz, 1H, ArH), 6.76 (d, J=8.8 Hz, 2H, ArH), 6.75 (d, J=8.9 Hz, 2H, ArH), 4.01 (q, J=7.0 Hz, 2H, CH$_2$), 3.88 (s, 3H, —OCH$_3$), 3.74 (s, 3H, —OCH$_3$), 1.39 (t, J=7.0, 3H, CH$_3$); $^{13}$C-NMR (CDCl$_3$, 90 Mhz): δ=193.1, 163.1, 159.7, 157.6, 142.3, 140.0, 134.0, 132.3, 130.6, 130.2, 126, 124.0, 114.7, 114.0, 114.0, 104.3, 63.7, 55.6, 55.2, 14.6. HRMS (EI) M$^+$ calcd for C$_{25}$H$_{22}$O$_4$S 418.1239, found 418.1241. Anal. Calcd for C$_{25}$H$_{22}$O$_4$S: C, 71.75; H, 5.30; S, 7.66. Found: C, 71.68; H, 5.30; S, 7.61.

Synthesis of 3-(3', 4', 5'-triethoxybenzoyl)-2-(4'-methoxyphenyl)-6-methoxybenzo[b]thiophene To a well stirred solution of 2-(4'-methoxyphenyl)-6-methoxybenzo[b]thiophene (0.501 g, 1.85 mmol) and 3,4,5-triethoxybenzoyl chloride (1.00 g, 3.66 mmol) in CH$_2$Cl$_2$ (45 ml) was added AlCl$_3$ (0.870 g, 6.52 mmol) portion-wise over a 15 minute period. After 30 minutes, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 70:30 EtOAc/hexanes) afforded the title compound (0.827 g, 1.63 mmol, 88%) as a pale yellow solid. Recrystallization (EtOAc/hexanes) afforded a highly pure, crystalline sample with mp 108–110° C. $^1$H-NMR (CDCl$_3$, 360 Mhz): δ=7.64 (d, J=8.9 Hz, 1H, ArH), 7.32 (d, J=2.3 Hz, 1H, ArH), 7.29 (d, J=8.7 Hz, 2H, ArH), 7.02 (s, 2H, ArH), 6.99 (dd, J=9.0, 2.4 Hz, 1H, ArH), 6.73 (d, J=8.7, 1H, ArH), 4.06 (q, J=7.1 Hz, 2H, CH$_2$), 3.91 (q, J=7.0, 4H, CH$_2$), 3.89 (s, 3H, —OCH$_3$), 3.74 (s, 3H, —OCH$_3$), 1.34 (t, J=7.0 Hz, 6H, CH$_3$), 1.28 (t, J=7.1 Hz, 3H, CH$_3$); $^{13}$C-NMR (CDCl$_3$, 90 MHz): δ=193.2, 159.8, 157.7, 152.5, 143.6, 142.6, 140.0, 133.9, 132.3, 130.3, 130.1, 126.0, 124.2, 114.8, 114.0, 108.9, 104.4, 68.8, 64.6, 55.6, 55.2, 15.4, 14.7. HRMS (EI) M$^+$ calcd for C$_{29}$H$_{30}$O$_6$S 506.1763, found 506.1777. Anal. Calcd for C$_{29}$H$_{30}$O$_6$S: C, 68.75; H, 5.97; S, 6.33. Found: C, 68.67; H, 5.97; S, 6.27.

Synthesis of 3-[3'-(3", 4", 5"-trimethoxyphenyl)propionyl]-2-(4'-methoxyphenyl)-6-methoxybenzo[b]thiophene To a well-stirred solution of 2-(4'-methoxyphenyl)-6-methoxybenzo[b]thiophene (0.206 g, 0.762 mmol) and 3-(3', 4', 5'-trimethoxyphenyl)propionyl chloride (0.390 g, 1.51 mmol) in CH$_2$Cl$_2$ (50 mL) was added AlCl$_3$ (0.520 g, 3.89 mmol) portion-wise over a 15 minute period. After 18 hours (total reaction time), water was added, and the product was isolated initially by extraction with CH$_2$Cl$_2$ and subsequently by extraction with EtOAc. The organic layers were separately washed sequentially with NaHCO$_3$ (sat) and brine and then combined and dried over MgSO$_4$. Purification by flash chromatography (silica gel, 70:30 EtOAc/hexane) afforded the title compound as an off-white solid. $^1$H-NMR (CDCl$_3$, 360 Mhz): δ=7.92 (d, J=8.9 Hz, 1H, ArH), 7.35 (d, J=8.7 Hz, 2H, ArH), 7.25 (m, 1H, ArH), 7.04 (dd, J=8.9, 2.4 Hz, 1H, ArH), 6.93 (d, J=8.7 Hz, 2H, ArH), 6.15 (s, 2H, ArH) 3.88 (s, 3H, —OCH$_3$), 3.85 (s, 3H, —OCH$_3$), 3.78 (s, 3H, —OCH$_3$), 3.72 (s, 6H, —OCH$_3$), 3.80 (t, 2H, CH$_2$), 3.70 (t, 2H, CH$_2$).

TUBULIN POLYMERIZATION ASSAY

IC$_{50}$ values for tubulin polymerization were determined according to the procedure described in Bai et al. Purified tubulin is obtained from bovine brain cells as described in Hamel and Lin. Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM $MgCl_2$, 4% DMSO and 0.1 M 4-morpholineethanesulfonate buffer (MES, pH 6.4). $IC_{50}$ is the amount of inhibitor needed to inhibit tubulin polymerization 50% with respect to the amount of inhibition that occurs in the absence of inhibitor. The $IC_{50}$ value determined for 3-(3',4',5'-Trimethoxybenzoyl)-2-(4'-methoxyphenyl)-6-methoxybenzo[b]thiophene was 1.5–2.5 $\mu$M.

CYTOTOXIC ASSAY WITH P388 LEUKEMIA CELLS

Some of the newly prepared compounds were evaluated for cytotoxic activity against P388 leukemia cells using an assay system similar to the National Institutes of Cancer procedure described below and in Monks et al. The $ED_{50}$ value (defined as the effective dosage required to inhibit 50% of cell growth) of 3-(3',4',5'-trimethoxybenzoyl)-2-(4'-methoxyphenyl)-6-methoxybenzo[b]thiophene was found to be 22.2 $\mu$g/ml. The $ED_{50}$ values of 3,5 -dimethoxybenzoyl, 2,6-dimethoxybenzoyl and 3,5-dimethoxy-4-hydroxybenzoyl derivatives of 2-(4-methoxyphenyl)-6-methoxybenzo-[b]thiophene compounds were estimated as greater than 100 $\mu$g/ml. The $ED_{50}$ value of a nitrogen derivative of combretastatin, 5-[(Z)-2-(3',4',5'-trimethoxyphenyl)ethenyl]-2-methoxy-N, N-bis-(phenylmethyl)aniline was 33.9 $\mu$g/ml.

GROWTH INHIBITORY ACTIVITY AGAINST OTHER CANCER CELL LINES 3-(3',4',5'-Trimethoxybenzoyl)-2-(4'-methoxyphenyl)-6-methoxybenzo[b]-thiophene was evaluated in terms of growth inhibitory activity against several human cancer cell lines, including ovarian CNS, renal, lung, colon and melanoma lines. The assay used is described in Monks et al. Briefly, the cell suspensions, diluted according to the particular cell type and the expected target cell density (5,000–40,000 cells per well based on cell growth characteristics), were added by pipet (100 $\mu$l) to 96-well microtiter plates. Inoculates were allowed a preincubation time of 24–28 hours at 37° C. for stabilization. Incubation with the inhibitor compounds lasted for 48 hours in 5% $CO_2$ atmosphere and 100% humidity. Determination of cell growth was done by in situ fixation of cells, followed by staining with a protein-binding dye, sulforhodamine B (SRB), which binds to the basic amino acids of cellular macromolecules. The solubilized stain was measured spectrophotometrically. The results of these assays are shown in Table 1. $GI_{50}$ is defined as the dosage required to inhibit tumor cell growth by 50%.

TABLE 1

Activity of 3-(3',4',5'-Trimethoxyphenyl)-2-(4'-methoxyphenyl)-6-methoxybenzo[b]thiophene Against Human Cancer Cell Lines

| Cell Type | Cell-Line | $GI_{50}$ $\mu$g/ml) |
|---|---|---|
| Ovarian | OVCAR-3 | $1.9 \times 10^{-1}$ |
| CNS | SF-295 | $2.0 \times 10^{-1}$ |
| Renal | A498 | $4.6 \times 10^{-1}$ |
| Lung-NSC | NCI-H460 | $1.3 \times 10^{-1}$ |

TABLE 1-continued

Activity of 3-(3',4',5'-Trimethoxyphenyl)-2-(4'-methoxyphenyl)-6-methoxybenzo[b]thiophene Against Human Cancer Cell Lines

| Cell Type | Cell-Line | $GI_{50}$ $\mu$g/ml) |
|---|---|---|
| Colon | KM20L2 | $4.9 \times 10^{-2}$ |
| Melanoma | SK-MEL-5 | $4.8 \times 10^{-1}$ |

EXAMPLE 1A

Improved Benzo[b]thiophene Derivative Syntheses

Experimental procedures for certain of the following compounds are described in Example 1. The biological activity presented in Example 1 (other than with P388 cells) related to compound 1 (and 1A) (3-(3', 4', 5'-trimethoxybenzoyl)-2-(4'-methoxyphenyl)-6-methoxybenzo[b]thiophene). The information for compound 1 is now updated. The inventors now report the $IC_{50}$ for inhibition of tubulin polymerization as an inhibition of the rate (Compound 1A and 10A) rather than a final "steady-state" number (all other compounds).

Compound 1A [same as compound 1 in Example 1]—3-(3', 4', 5'-trimethoxybenzoyl)-2-(4'-methoxyphenyl)-6-methoxybenzo[b]thiophene (see FIG. 2A, FIG. 2B and FIG. 4), was retested for various activities.

Inhibition of tubulin polymerization with compound 1A gave 50% inhibition of the maximum tubulin assembly rate at 1.1 $\mu$M. The same assay with combretastatin A-4 gave a maximum rate of 0.73 $\mu$m. Electron microscopy failed to demonstrate any morphological difference in polymer formed in the presence or absence of compound 1A. In both cases a mixture of microtubules and ribbons composed of parallel protofilaments was observed.

The human Burkitt lymphoma line CA46 was treated with varying concentrations of compound 1A, and a 50% growth inhibition occurred at 2 $\mu$M. Cells treated with a 10 $\mu$M concentration had a marked increase in the mitotic index, from 3% to 30%. Such an antimitotic effect, when combined with the tubulin assembly data, is strong evidence that tubulin is the intracellular target of compound 1A.

Modest inhibition (23%) of the binding of [$^3$H]colchicine to tubulin was observed with 5 $\mu$M compound 1A, as compared with the total inhibition caused by combretastatin A-4. Increasing the concentration of compound 1A to 50 $\mu$M resulted in little additional inhibition.

Figure 5:
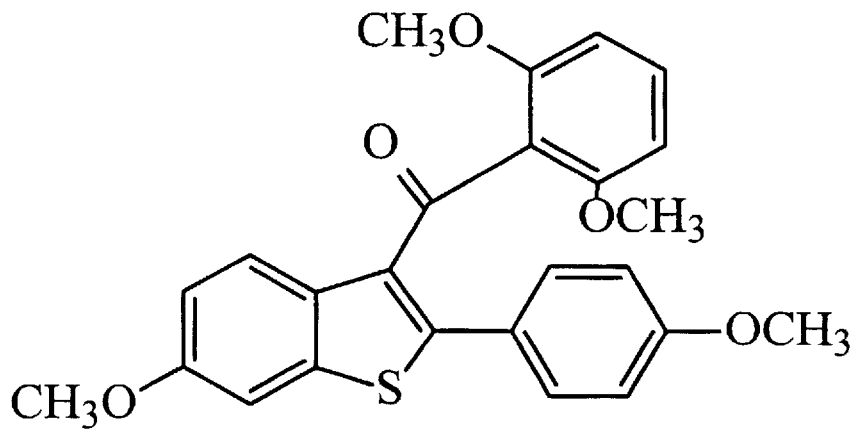
FIG. 5 shows compound 2A, 3-(2', 6'-dimethoxybenzoyl)-2-(4'-methoxyphenyl)-6-methoxybenzo[b]thiophene

Compound 2A—3-(2', 6'-dimethoxybenzoyl)-2-(4'-methoxyphenyl)-6-methoxybenzo[b]thiophene (see FIG. 5) was found only mildly active with P388 cells as shown in Table 2.

TABLE 2

P388 Leukemia Data (Compound 2A)

| Cell Type | Cell Line | $ED_{50}$ ($\mu$g/ml) |
|---|---|---|
| Mouse Leukemia | P388 | >100 |

Figure 6:
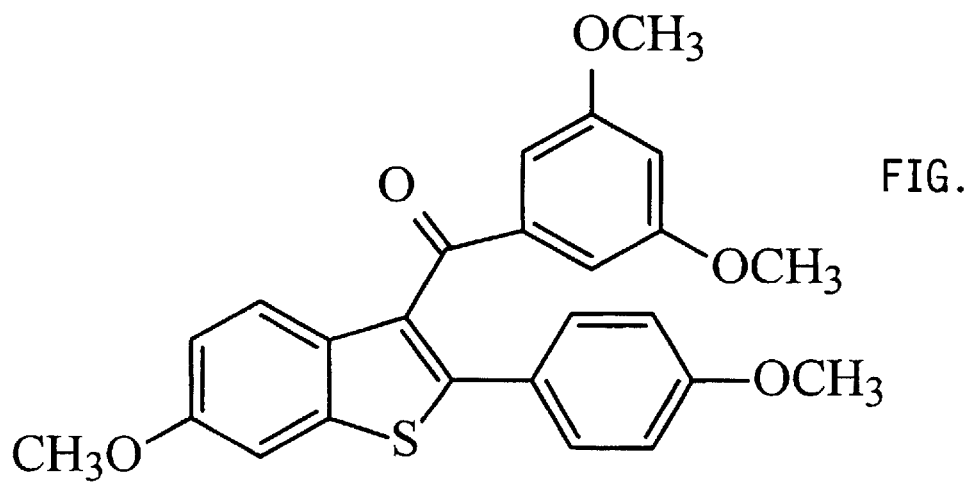
FIG. 6 shows compound 3A, 3-(3', 5'-dimethoxybenzoyl)-2-(4'-methoxyphenyl)-6-methoxybenzo[b]thiophene

Compound 3A—3-(3', 5'-dimethoxybenzoyl)-2-(4'-methoxyphenyl)-6-methoxybenzo[b]thiophene (see FIG. 6) was also only mildly active with the P388 cell line as shown in Table 3.

TABLE 3

P388 Leukemia Data (Compound 3A)

| Cell Type | Cell Line | ED$_{50}$ (µg/ml) |
|---|---|---|
| Mouse Leukemia | P388 | >100 |

Figure 7:
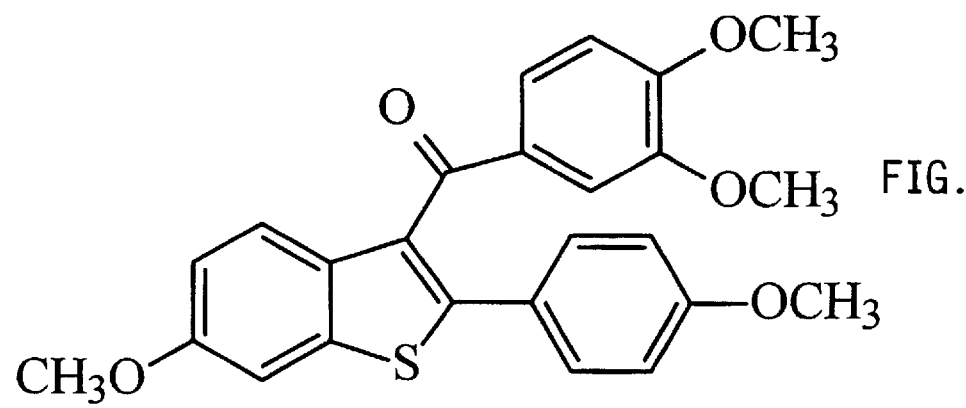
FIG. 7 shows compound 4A, 3-(3', 4'-dimethoxybenzoyl)-2-(4'-methoxyphenyl)-6-methoxybenzo[b]thiophene

Compound 4A—3-(3', 4'-dimethoxybenzoyl)-2-(4'-methoxyphenyl)-6-methoxybenzo[b]thiophene (see FIG. 7) was synthesized and tested anew. The improved experimental as compared to that in Example 1 is included (immediately below) for compound 4A, found better than that in Example 1.

To a well stirred solution of 2-(4'methoxyphenyl)-6-methoxybenzo[b]thiophene (0.327 g, 1.21 mmol) and 3,4-dimethoxybenzoyl chloride (0.557 g, 2.77 mmol) in CH$_2$Cl$_2$ (20 ml) was added AlCl$_3$ (0.616 g, 4.62 mmol) portion-wise over a 15 min period. After 7 h, water was added, and the product was isolated initially by extraction with CH$_2$Cl$_2$ and subsequently by extraction with EtOAc. The organic layers were separately washed with brine, combined and dried over MgSO$_4$. Purification by flash chromatography (silica gel, 60:40 Et$_2$O/hexanes) afforded 5 (0.402 g, 0.92 mmol, 76%) as a pale yellow solid. H-NMR (CDCl$_3$, 360 MHz) d 7.54 (d, J=8.9 Hz, 1H, ArH), 7.50 (d, J=1.9 Hz, 1H, ArH), 7.34 (d, J=8.9 Hz, 2H, ArH), 7.33 (m, 4H, ArH), 6.96 (dd, J=8.9, 2.4 Hz, 1H, ArH), 6.75 (d, J=6.7, 2H, ArH), 6.66 (d, J=8.5, 1H, ArH), 3.88 (s, 3H, —OCH$_3$), 3.85 (s, 6H, —OCH$_3$), 3.74 (s, 3H, —OCH$_3$).

Compound 4A, 3-(3', 4'-dimethoxybenzoyl)-2-(4'-methoxyphenyl)-6-methoxybenzo[b]thiophene, had biological activity as shown in Tables 4 and 5.

Compound 4A gave inhibition of tubulin polymerization with an IC$_{50}$>40 µM.

TABLE 4

P388 Leukemia Data (Compound 4A)

| Cell Type | Cell Line | ED$_{50}$ (µg/ml) |
|---|---|---|
| Mouse Leukemia | P388 | >10 |

TABLE 5

Human Cancer Cell Line Studies (Compound 4A)

| Cell Type | Cell Line | GI$_{50}$ (µg/ml) |
|---|---|---|
| Pancreas adn | BXPC-3 | 5.2 |
| Neuroblast | SK-N-SH | 3.2 |
| Thyroid ca | SW1736 | >10 |
| Lung-NSC | NCI-H460 | 4.6 |
| Pharynx-sqam | FADU | 4.7 |
| Prostate | DU-145 | >10 |

Figure 8:
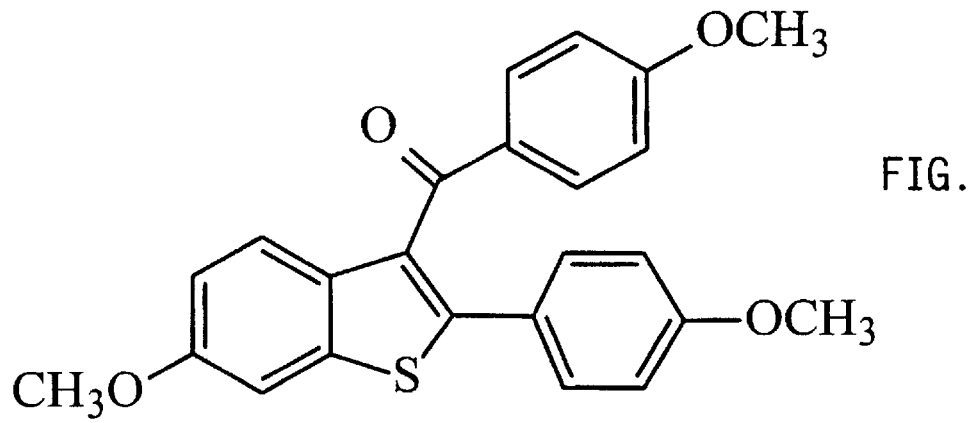
FIG. 8 shows compound 5A, 3-(4'-methoxybenzoyl)-2-(4'-methoxyphenyl)-6-methoxybenzo[b]thiophene

Compound 5A—3-(4'-methoxybenzoyl)-2-(4'-methoxyphenyl)-6-methoxybenzo[b]thiophene (see FIG. 8), as shown in Table 6 and 7, had certain biological activity.

TABLE 6

P388 Leukemia Data (Compound 5A)

| Cell Type | Cell Line | ED$_{50}$ (µg/ml) |
|---|---|---|
| Mouse Leukemia | P388 | >100 |

TABLE 7

Human Cancer Cell Line Studies (Compound 5A)

| Cell Type | Cell Line | GI$_{50}$ (µg/ml) |
|---|---|---|
| Pancreas adn | BXPC-3 | 8.9 |
| Melanoma | RPMI-7951 | >10 |
| CNS | U251 | >10 |
| Lung-NSC | NCI-H460 | >10 |
| Pharynx-sqam | FADU | >10 |
| Prostate | DU-145 | >10 |

Figure 9:
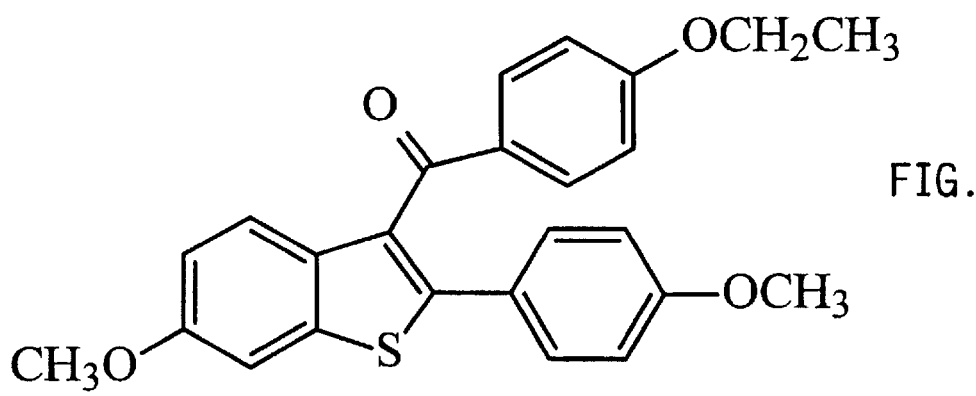
FIG. 9 shows compound 6A, 3-(4'-ethoxybenzoyl)-2-(4'-methoxyphenyl)-6-methoxybenzo[b]thiophene

Compound 6A—3-(4'-ethoxybenzoyl)-2-(4'-methoxyphenyl)-6-methoxybenzo[b]thiophene (see FIG. 9) has notable biological activity as seen in Tables 8 and 9.

TABLE 8

P388 Leukemia Data (Compound 6A)

| Cell Type | Cell Line | ED$_{50}$ (µg/ml) |
|---|---|---|
| Mouse Leukemia | P388 | >100 |

TABLE 9

Human Cancer Cell Line Studies (Compound 6A)

| Cell Type | Cell Line | GI$_{50}$ (µg/ml) |
|---|---|---|
| Pancreas adn | BXPC-3 | 0.65 |
| Melanoma | RPMI-7951 | 3.2 |
| CNS | U251 | 0.43 |
| Lung-NSC | NCI-H460 | 2.4 |
| Pharynx-sqam | FADU | 0.48 |
| Prostate | DU-145 | 3.9 |

Figure 10:
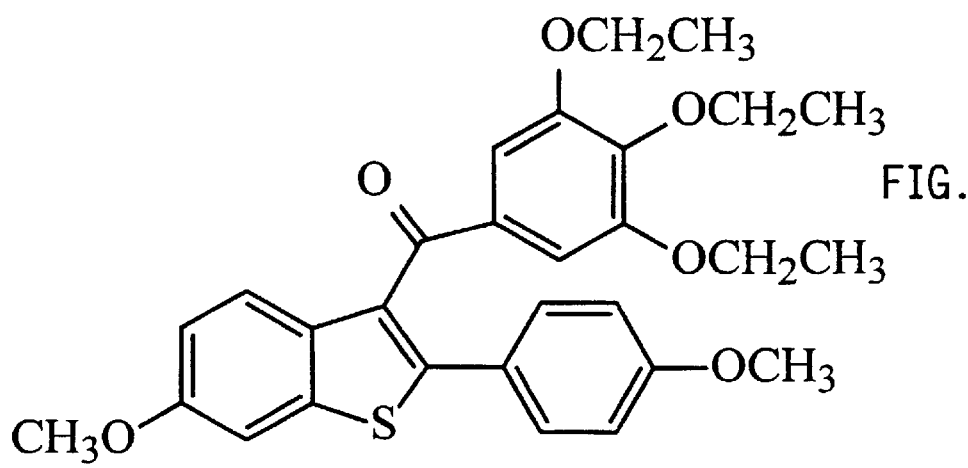
FIG. 10 shows compound 7A, 3-(3', 4', 5'-triethoxybenzoyl)-2-(4'-methoxyphenyl)-6-methoxybenzo[b]thiophene

Compound 7A—3-(3', 4', 5'-triethoxybenzoyl)-2-(4'-methoxyphenyl)-6-methoxybenzo[b]thiophene (see FIG. 10) is described in Example 1.

Compound 7A was found to be mildly active in the cell toxicity tests as shown in Tables 10 and 11.

TABLE 10

P388 Leukemia Data (Compound 7A)

| Cell Type | Cell Line | ED$_{50}$ (µg/ml) |
|---|---|---|
| Mouse Leukemia | P388 | >100 |

TABLE 11

Human Cancer Cell Line Studies (Compound 7A)

| Cell Type | Cell Line | GI$_{50}$ (µg/ml) |
|---|---|---|
| Pancreas adn | BXPC-3 | >10 |
| Melanoma | RPMI-7951 | >10 |
| CNS | U251 | >10 |

TABLE 11-continued

Human Cancer Cell Line Studies (Compound 7A)

| Cell Type | Cell Line | GI$_{50}$ (µg/ml) |
|---|---|---|
| Lung-NSC | NCI-H460 | >10 |
| Pharynx-sqam | FADU | >10 |
| Prostate | DU-145 | >10 |

Figure 11:
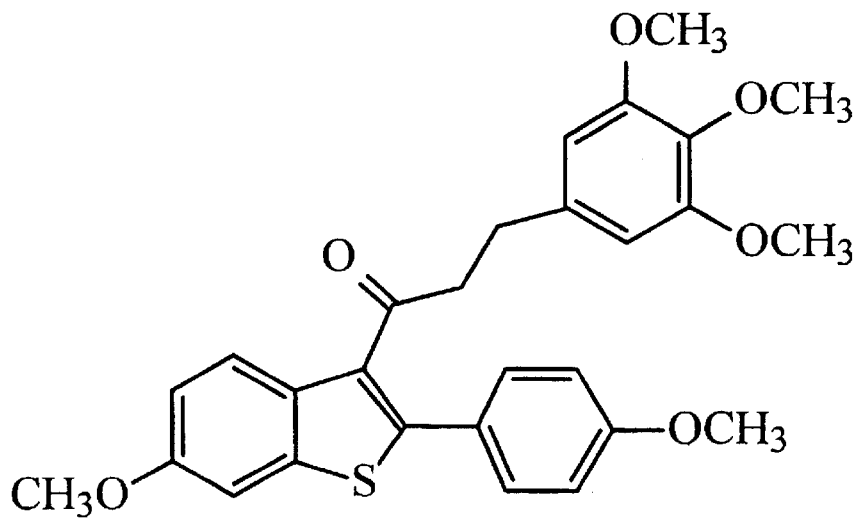
FIG. 11 shows compound 8A, 3-[3'-(3', 4', 5'-trimethoxyphenyl)propionyl]-2-(4'-methoxyphenyl)-6-methoxybenzo[b]thiophene

Compound 8A—3-[3'-(3', 4', 5'-trimethoxyphenyl) propionyl]-2-(4'-methoxyphenyl)-6-methoxybenzo[b] thiophene (see FIG. 11) was synthesized as follows (an improved synthesis is compared to that in Example 1).

To a well stirred solution of 2-(4'-methoxyphenyl)-6-methoxybenzo[b]thiophene (0.500 g, 1.85 mmol) and 3'-(3', 4',5'trimethoxyphenyl) propionyl chloride (1.43 g, 5.55 mmol) in CH$_2$Cl$_2$ (50 mL) was added AlCl$_3$ (1.00 g, 7.50 mmol) portion-wise over a 15 min period. After 18 h, water was added, and the product was isolated initially by extraction with CH$_2$Cl$_2$ and subsequently by extraction with EtOAc. The organic layers were separately washed with NaHCO$_3$ (sat) and brine, and then combined and dried over MgSO$_4$. Purification by flash chromatography (silica gel, 70:30 hexane/EtOAc) afforded 4 (0.089 g, 0.18 mmol, 9.8%) as an off-white solid. Recrystallization (ethanol/hexane) yielded a highly pure, crystalline sample with an mp=127–128° C. $^1$H-NMR (CDCl$_3$, 360 MHz) d 7.92 (d, J=8.9 Hz, 1H, ArH), 7.35 (d, J=8.7 Hz, 2H, ArH), 7.25 (d, J=2.4 Hz, 1H, ArH), 7.04 (dd, J=8.9 Hz, 2.4 Hz, 1H, ArH), 6.93 (d, J=8.7 Hz, 2H, ArH), 3.88 (s, 3H, —OCH$_3$), 3.85 (s, 3H, —OCH$_3$), 3.78 (s, 3H, —OCH$_3$), 3.72 (s, 6H, —OCH$_3$), 3.8 (t, J=7.5 Hz, 2H, CH$_2$), 3.7 (t, J=7.45 , 2H, CH$_2$); $^{13}$C-NMR(CDCl$_3$, 90 Mhz) 200.8, 160.5, 157.8, 153.0, 146.0, 140.0, 136.5, 136.2, 132.5, 132.3, 130.8, 126.2, 124.7, 115.1, 114.3, 105.2, 104.3, 60.8, 55.9, 55.6, 55.3, 44.8, 31.1. HRMS (EI) M$^+$ calcd for C$_{28}$H$_{28}$O$_6$S 492.1607, found 492.2337. Anal. Calcd for C$_{28}$H$_{28}$O$_6$S: C, 68.27; H, 5.73; S, 6.51. Found: C, 68.17; H, 5.80; S, 6.50.

Compound 8A, 3-[3-(3', 4', 5'-trimethoxyphenyl) propionyl]-2-(4'-methoxyphenyl)-6-methoxybenzo[b] thiophene (see FIG. 11), had biological activity as shown in Tables 12 and 13.

TABLE 12

P388 Leukemia Data (Compound 8A)

| Cell Type | Cell Line | ED$_{50}$ (µg/ml) |
|---|---|---|
| Mouse Leukemia | P388 | >10 |

TABLE 13

Human Cancer Cell Line Studies (Compound 8A)

| Cell Type | Cell Line | GI$_{50}$ (µg/ml) |
|---|---|---|
| Pancreas adn | BXPC-3 | >10 |
| Melanoma | RPMI-7951 | >10 |
| CNS | U251 | 4.5 |
| Lung-NSC | NCI-H460 | 3.8 |
| Pharynx-sqam | FADU | 9.1 |
| Prostate | DU-145 | >10 |

Figure 12:
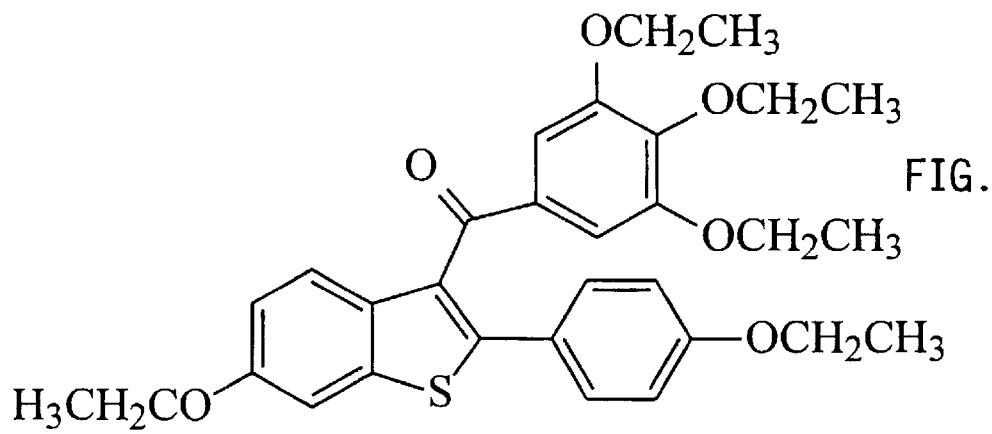
FIG. 12 shows compound 9A, 3-(3',4',5'-triethoxybenzoyl)-2-(4'-ethoxyphenyl)-6-ethoxybenzo[b]thiophene

Compound 9A—3-(3',4',5'-triethoxybenzoyl)-2-(4'-ethoxyphenyl)-6-ethoxybenzo[b]thiophene (see FIG. 12) was synthesized as follows.

To a well-stirred solution of 2-(4'ethoxyphenyl)-6-ethoxybenzo[b]thiophene (0.087 g, 0.291 mmol) and 3, 4, 5-triethoxybenzoyl chloride (0.200 g, 0.733 mmol) in CH$_2$Cl$_2$ (30 ml) was added AlCl$_3$ (0.126 g, 0.942 mmol) portionwise over a 5 min period. After 24 h, water was added, and the product was isolated initially by extraction with CH$_2$Cl$_2$ and subsequently by extraction with EtOAc. The organic layers were washed separately with brine and then combined and dried over MgSO$_4$. Purification by flash chromatography (silica gel, 80:20 hexane/EtOAc) afforded a highly pure sample of the desired product (0.043 g, 28%) as a white solid with mp 126–128° C. $^1$H-NMR (CDCl$_3$, 360 MHz) d 7.64 (d, J=8.9 Hz, 1H, ArH), 7.31 (d, J=2.3 Hz, 1H, ArH), 7.27 (d, J=9.3 Hz, 2H, ArH), 7.02 (s, 2H, ArH), 6.99 (dd, J=8.9, 2.3 Hz, 1H, ArH), 6.71 (d, J=8.7 Hz, 2H, ArH), 4.11 (q, J=6.9 Hz, 2H, —OCH$_2$), 4.06 (q, J=7.1 Hz, 2H, OCH$_2$), 3.95 (q, J=3.9 Hz, 2H, —OCH$_2$), 3.91 (q, J=6.96 Hz, 4H, —OCH$_2$), 1.46 (t, J=7.0 Hz, 3H, CH$_3$), 1.37 (t, J=7.0 Hz, 3H, CH$_3$), 1.34 (t, J=7.0 Hz, 6H, CH$_3$), 1.28 (t, J=7.0 Hz, 3H, CH$_3$); $^{13}$C-NMR (CDCl$_3$, 90 MHz) d 193.3, 159.2, 157.0, 152.5, 143.6, 143.3, 140.0, 133.9, 132.3, 130.3, 130.1, 126.0, 124.2, 115.3, 114.5, 109.0, 105.3, 68.9, 64.7, 63.9, 63.4, 15.5, 14.8, 14.8, 14.7. HRMS (EI) M$^+$ calc for C$_{31}$H$_{34}$O$_6$S 534.753, found 534.2185. Anal calcd for C$_{31}$H$_{34}$O$_6$S: C, 69.64; H,6.41; S, 5.99. Found: C, 69.45; H, 6.50; S, 5.94.

Compound 9A was tested for biological activity as shown in Tables 14 and 15.

TABLE 14

P388 Leukemia Data (Compound 9A)

| Cell Type | Cell Line | ED$_{50}$ (µg/ml) |
|---|---|---|
| Mouse Leukemia | P388 | >10 |

TABLE 15

Human Cancer Cell Line Studies (Compound 9A)

| Cell Type | Cell Line | GI$_{50}$ (µg/ml) |
|---|---|---|
| Pancreas adn | BXPC-3 | >10 |
| Melanoma | RPMI-7951 | >10 |
| CNS | U251 | >10 |
| Lung-NSC | NCI-H460 | >10 |
| Pharynx-sqam | FADU | >10 |
| Prostate | DU-145 | >10 |

Figure 13:
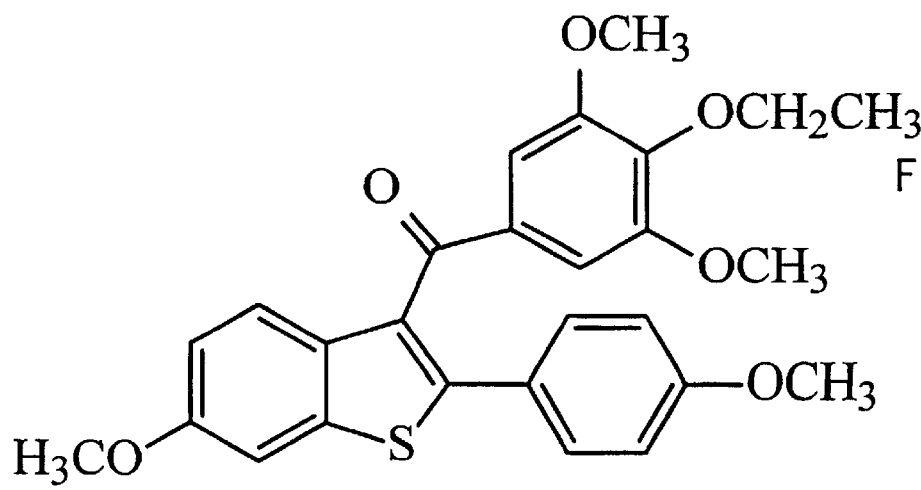
FIG. 13 shows compound 10A, 3-(4'-ethoxy-3', 5'-dimethoxybenzoyl)-2-(4'-methoxyphenyl)-6-methoxybenzo[b]thiophene

Compound 10A—3-(4'-ethoxy-3', 5'-dimethoxybenzoyl)-2-(4'-methoxyphenyl)-6-methoxybenzo[b]thiophene (see FIG. 13) was synthesized as follows.

To a well stirred solution of NaH (0.049 g, 2.041 mmol) and 3-(3', 5'-dimethoxy-4'hydroxybenzoyl)-2-(4'-methoxyphenyl)-6-methoxybenzo[b]thiophene (0.105 g, 0.233 mmol) in THF (30 ml), cooled in ice was added ethyltrifluoromethane sulfonate (0.1 ml, 0.137 g, 0.771 mmol). After 30 min, water was added and the product was isolated initially by extraction with CH$_2$Cl$_2$ and subsequently by extraction with EtOAc. The organic layers were washed with NaHCO$_3$ followed by brine and then the combined organic layers were dried over MgSO$_4$. Purification by flash chromatography (silica gel, 70:30 hexane/EtOAc) afforded the desired product as a white solid (0.037 g, 0.077 mmol, 35%) with mp 138–139° C. $^1$H -NMR (CDCl$_3$, 360 MHz) d 7.69 (d, J=8.9 Hz, 1H, ArH), 7.33 (d, J=2.3 Hz, 1H, ArH), 7.29 (d, J=8.7 Hz, 2H, ArH), 7.05 (s, 2H, ArH), 7.01 (dd, J=8.9, 2.4 Hz, 1H, ArH), 6.74 (d, J=8.7 Hz, 2H, ArH), 4.05 (q, J=7.1 Hz, 2H, —OCH$_2$), 3.90 (s, 3H, OCH$_3$), 3.74 (s, 3H, —OCH$_3$), 3.71 (s, 6H, —OCH$_3$), 1.29 (t, J=7.0, 3H, CH$_3$); HRMS (EI) M$^+$ calcd for C$_{27}$H$_{26}$O$_6$S 478.1450, found 478.1434.

Compound 10A behaves very similarly to compound 1A. It demonstrates clear inhibition of tubulin polymerization of rate, but not of plateau. The polymerization curves obtained with 4, 10, and 40 μM of compound 10A were nearly identical. Biological activity of compound 10A is shown in Table 16.

TABLE 16

Human Cancer Cell Line Studies (Compound 10A)

| Cell Type | Cell Line | GI$_{50}$ (μg/ml) |
|---|---|---|
| Pancreas adn | BXPC-3 | 0.22 |
| Melanoma | SK-N-SH | 0.17 |
| Thyroid ca | SW1736 | 0.31 |
| Lung-NSC | NCI-H460 | 0.32 |
| Pharynx-sqam | FADU | 0.31 |
| Prostate | DU-145 | 0.35 |

Figure 14:
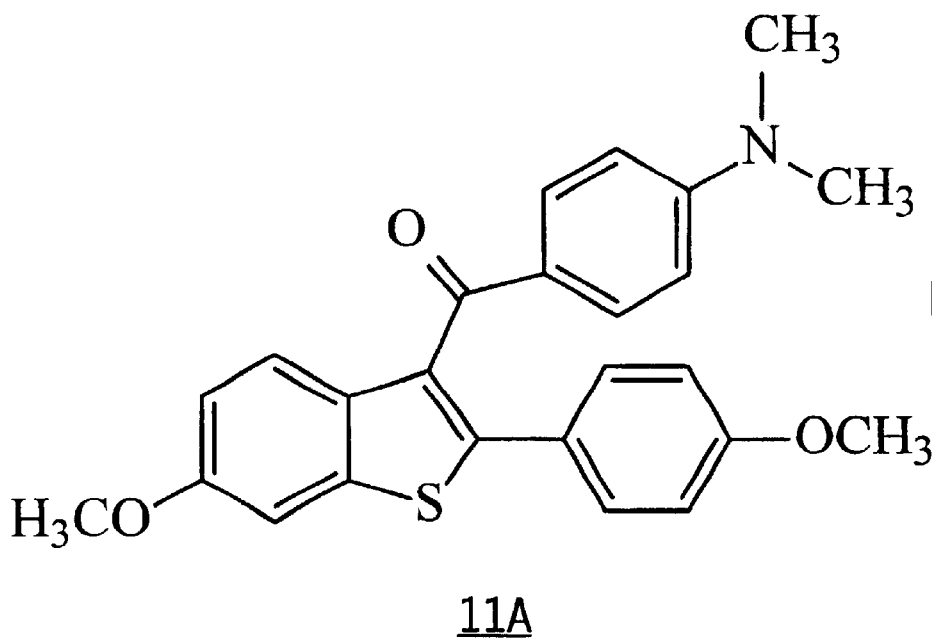
FIG. 14 shows compound 11A, 3-(4'-N,N-dimethylaminobenzoyl)-2-(4'-methoxyphenyl)-6-methoxybenzo[b]thiophene

Compound 11A—3-(4'-N,N-dimethylaminobenzoyl)-2-(4'-methoxyphenyl)-6-methoxybenzo[b]thiophene (see FIG. 14) was synthesized as follows.

To a well stirred solution of 2-(4'-methoxyphenyl)-6-methoxybenzo[b]thiophene (0.501 g, 1.85 mmol) and 4-N,N-dimethylaminobenzoyl chloride (1.43 g, 5.55 mmol) in CH$_2$Cl$_2$ (50 mL) was added AlCl$_3$ (1.147 g, 8.60 mmol) portion-wise over a 15 min period. After 24 h, the reaction mixture was refluxed for 2 h and then quenched with water. The product was isolated initially by extraction with CH$_2$Cl$_2$ and subsequently by extraction with EtOAc. The organic layers were separately washed with saturated NaHCO$_3$ and then with brine. They were then combined and dried over MgSO$_4$. Purification by flash chromatography (silica gel, 70:30 hexane/EtOAc) afforded 6 (0.408 g, 0.98 mmol, 53%) as an pale yellow solid. Recrystallization (ethanol/hexane/CH$_2$Cl$_2$) yielded a highly pure, crystalline sample of 6 with an mp=163–164° C. $^1$H -NMR (CDCl$_3$, 360 MHz) d 7.74 (dt, J=9.1, Hz, 2H, ArH), 7.45 (d, J=8.7 Hz, 1H, ArH), 7.42 (dt, J=8.9, 2.2 Hz, 2H, ArH), 7.31 (d, J=2.3 Hz, 1H, ArH), 6.92 (dd, J=8.9, 2.4 Hz, 1H, ArH), 6.75 (dt, J=8.9, 2.2 Hz, 2H, ArH), 6.51 dt, J=9.2, Hz, 2H, ArH), 3.87 (s, 3H, —OCH$_3$), 3.75 (s, 3H, —OCH$_3$), 3.01 (s, 6H, —N(CH$_3$)$_2$); $^{13}$C-NMR(CDCl$_3$, 90 MHz) HRMS (EI) M$^+$ calcd for C$_{25}$H$_{23}$O$_3$NS 417.1400, found 417.1390. Anal. Calcd for C$_{25}$H$_{23}$O$_3$NS: C, 71.92; H, 5.81; N, 3.36; S, 7.68. Found C, 71.81; H, 5.55; N, 3.38; S, 7.68.

Compound 11A showed an inhibition of tubulin polymerization with an IC$_{50}$>40 μM. Further biological activity of compound 11A is shown in Table 17.

TABLE 17

Human Cancer Cell Line Studies (Compound 11A)

| Cell Type | Cell Line | GI$_{50}$ (μg/ml) |
|---|---|---|
| Pancreas adn | BXPC-3 | >10 |
| Neuroblast | SK-N-SH | >10 |
| Thyroid ca | SW1736 | >10 |
| Lung-NSC | NCI-H460 | >10 |
| Pharynx-sqam | FADU | >10 |
| Prostate | DU-145 | >10 |

Figure 15:
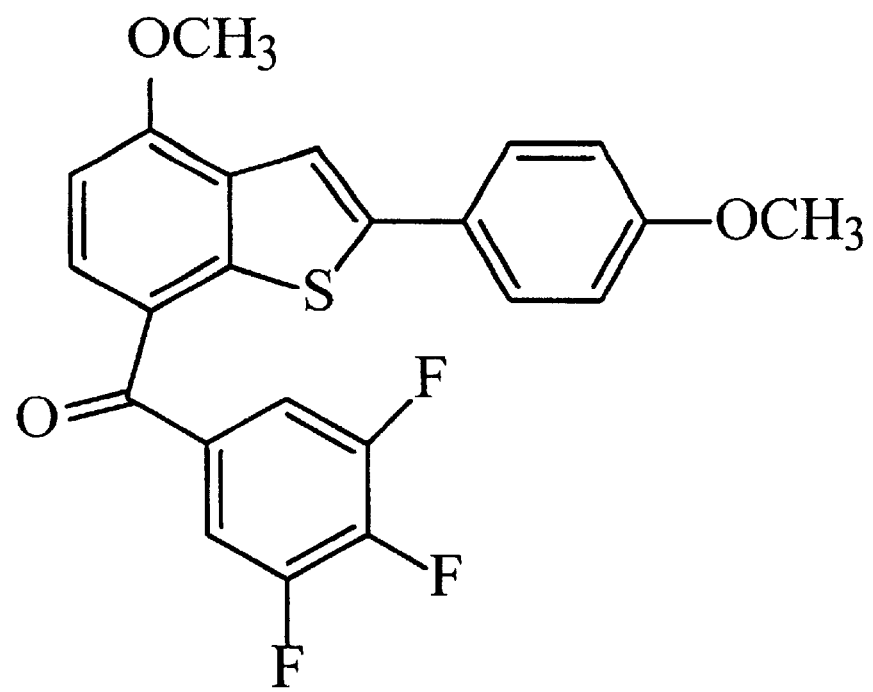
FIG. 15 shows compound 12A, 7-(3', 4', 5'-trifluorobenzoyl)-2-(4'-methoxyphenyl)-4-methoxybenzo[b]thiophene

Compound 12A—7-(3', 4', 5'-trifluorobenzoyl)-2-(4'-methoxyphenyl)-4-methoxybenzo[b]thiophene (see FIG. 15) was synthesized as follows:

To a well stirred solution of 2-(4'-methoxyphenyl)-4-methoxybenzo[b]thiophene (0.201 g, 0.74 mmol) and 3,4,5-trifluorobenzoyl chloride (0.288 g, 1.48 mmol) in CH$_2$Cl$_2$ (7 mL) was added AlCl$_3$ (0.304 g, 2.22 mmol) portion-wise over a 15 minute period. After 18 h, water was added, and the product was isolated initially with CH$_2$Cl$_2$ and subsequently by extraction with EtOAc. The organic layers were separately washed sequentially with NaHCO$_3$ and brine and then dried over MgSO$_4$. Purification by flash chromatography (silica gel, 80:20 hexane/EtOAc) afforded benzo[b]thiophene (0.032 g, 0.08 mmol, 10%) as a white solid. Recrystallization (Ethanol/hexane/CH$_2$Cl$_2$) yielded a highly pure crystalline sample. $^1$H-NMR(CDCl$_3$, 360 MHz) δ7.74 (d, J=8.9 Hz, 2H, ArH), 7.70 (d, J=9.3 Hz, 1H, ArH), 7.68 (s, 1H, ArH), 7.43 (dd, J=7.5, 6.6 Hz, 2H, ArH), 7.00 (d, J=8.9 Hz, 2H, ArH), 6.83 (d, J=8.4 Hz, 1H, ArH), 4.09 (s, 3H, —OCH$_3$), 3.87 (S, 3H, —OCH$_3$). $^{13}$C-NMR (CDCl$_3$, 90 MHz) 190.5, 160.1, 159.1, 152.3, 150.0, 146.6, 141.3, 134.4, 132.9, 132.1, 127.9, 126.9, 122.4, 114.5, 114.1, 114.1, 114.0, 113.9, 113.8, 56.0, 55.4. HRMS (EI) M$^+$ calcd for C$_{23}$H$_{15}$F$_3$O$_3$S 428.0694 found 428.0620. Compound 12A shows an inhibition of tubulin polymerization >40 μM. Biological activity of compound 12A is shown in Table 18.

TABLE 18

Human Cancer Cell Line Studies (Compound 12A)

| Cell Type | Cell Line | GI$_{50}$ (μg/ml) |
|---|---|---|
| Pancreas adn | BXPC-3 | >10 |
| Neuroblast | SK-N-SH | >10 |
| Thyroid ca | SW1736 | >10 |
| Lung-NSC | NCI-H460 | >10 |
| Pharynx-sqam | FADU | 6.7 |
| Prostate | DU-145 | >10 |

Figure 16:
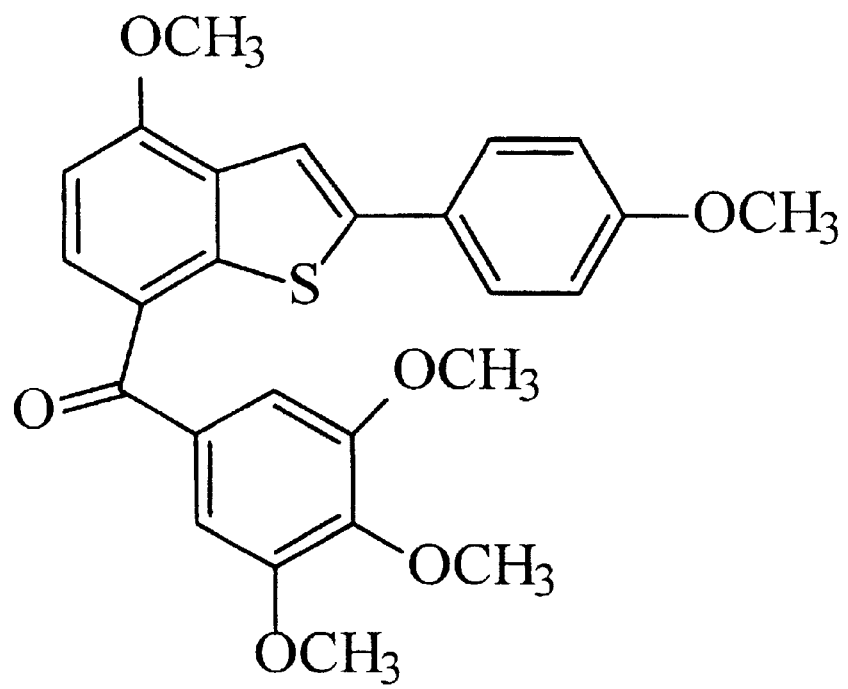
FIG. 16 shows compound 13A, 7-(3', 4', 5'-trimethoxybenzoyl)-2-(4'-methoxyphenyl)-4-methoxybenzo[b]thiophene

Compound 13A—7-(3', 4', 5'-trimethoxybenzoyl)-2-(4'-methoxyphenyl)-4-methoxybenzo[b]thiophene (see FIG. 16) are synthesized as follows:

To a well stirred solution of 2-(4'-methoxyphenyl)-4-methoxybenzo[b]thiophene (0.200 g, 0.74 mmol) and 3,4,5-trimethoxybenzoyl chloride (0.184 g, 0.74 mmol) in CH$_2$Cl$_2$ (7mL) was added AlCl$_3$ (0.200 g, 1.48 mmol) portion-wise over a 15 minute period. After 18 h, water was added, and the product was isolated initially with CH$_2$Cl$_2$ and subsequently by extraction with EtOAc. The organic layers were separately washed sequentially with NaHCO$_3$ and brine and then dried over MgSO$_4$. Purification by flash chromatography (silica gel, 70:30 hexane/EtOAc) afforded benzo[b]thiophene (0.023 g, 0.05 mmol, 7%) as a white solid. Recrystallization (Ethanol/hexane/CH$_2$Cl$_2$) yielded a highly pure crystalline sample. $^1$H-NMR (CDCl$_3$, 360 MHz) δ7.80 (d, J=8.4 Hz, 1H, ArH), 7.73 (d, J=8.8 Hz, 2H, ArH), 7.66 (s, 1H, ArH), 7.02 (s, 2H, ArH), 6.96 (d, J=8.8 Hz, 2H, ArH), 6.70 (d, J=8.3 Hz, 1H, arH), 4.08 (s, 3H, —OCH$_3$), 3.95 (s, 3H, —OCH$_3$), 3.91 (s, 6H, —OCH$_3$), 3.87 (S, 3H, —OCH$_3$), HRMS (EI) M$^+$ calcd for C$_{26}$H$_{24}$O$_6$S 464.1294, found 464.1310. Anal. Calcd for C$_{26}$H$_{24}$O$_6$S: C, 67.23; H, 5.21; S, 6.90. Found C, 67.19; H, 5.26; S, 6.87. Compound 13A shows an inhibition of tubulin polymerization >40 μM. Biological activity of compound 13A is shown in Table 19.

TABLE 19

Human Cancer Cell Line Studies (Compound 13A)

| Cell Type | Cell Line | GI$_{50}$ (μg/ml) |
|---|---|---|
| Pancreas adn | BXPC-3 | >10 |
| Neuroblast | SK-N-SH | >10 |
| Thyroid ca | SW1736 | >10 |
| Lung-NSC | NCI-H460 | >10 |
| Pharynx-sqam | FADU | 7.8 |
| Prostate | DU-145 | >10 |

Figure 17:
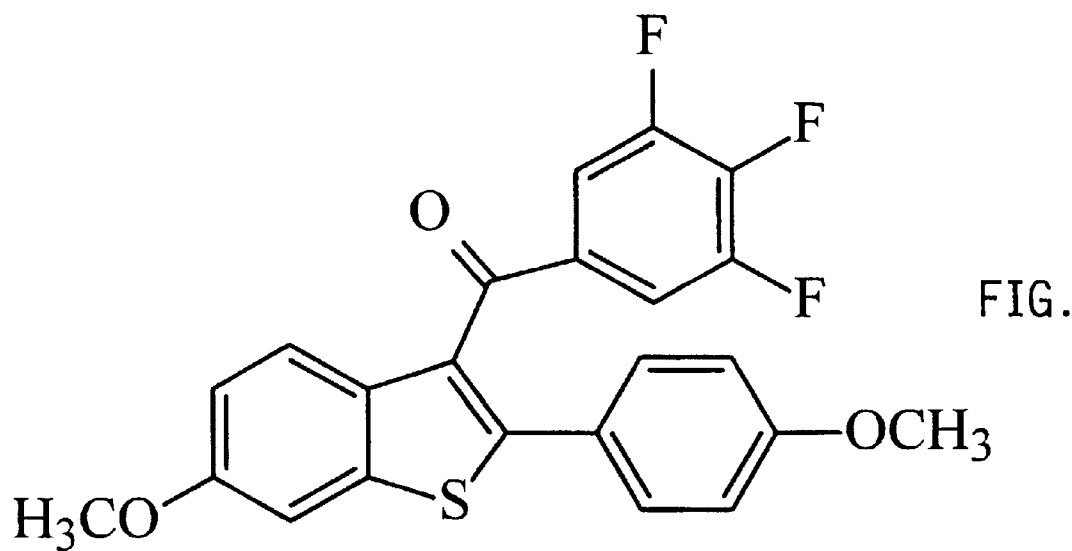
FIG. 17 shows compound 14A, 3-(3', 4', 5'-trifluorobenzoyl)-2-(4'-methoxyphenyl)-6-methoxybenzo[b]thiophene

Compound 14A—3-(3', 4', 5'-trifluorobenzoyl)-2-(4'-methoxyphenyl)-6-methoxybenzo[b]thiophene (see FIG. 17) was synthesized as follows.

To a well-stirred solution of 2-(4'methoxyphenyl)-6-methoxybenzo[b]thiophene (0.112 g, 0.414 mmol) and 3, 4, 5-trifluorobenzoyl chloride (0.437 g, 2.271 mmol) in CH$_2$Cl$_2$ (40 ml) was added AlCl$_3$ (0.471 g, 3.532 mmol) portionwise over a 15 min period under reflux conditions. After 30 h, water was added, and the product was isolated initially by extraction with CH$_2$Cl$_2$ and subsequently by extraction with EtOAc. The organic layers were washed separately with brine and then combined and dried over MgSO$_4$. Purification by flash chromatography (silica gel, first with hexanes then with 95:5 hexane/EtOAc) afforded a yellow liquid (0.068 g, 43%). $^1$H-NMR (CDCl$_3$, 360 MHz) d 7.69 (d, J=8.9 Hz, 1H, ArH), 7.37 (d, J=6.7 Hz, 1H, ArH), 7.35 (d, J=6.7 Hz, 1H, ArH), 7.33 (d, J=2.4 Hz, 1H, ArH), 7.26 (d, J=8.8 Hz, 2H, ArH), 7.04 (dd, J=8.9, 2.4 Hz, 1H, ArH), 6.77 (d, J=8.8 Hz, 2H, ArH), 3.90 (s, 3H, OCH$_3$), 3.77 (s, 3H, —OCH$_3$).

Compound 14A showed inhibition of tubulin polymerization with an IC$_{50}$>40 μM. Biological activity of compound 14A is shown in Table 20.

TABLE 20

Human Cancer Cell Line Studies (Compound 14A)

| Cell Type | Cell Line | GI$_{50}$ (μg/ml) |
|---|---|---|
| Pancreas adn | BXPC-3 | >10 |
| Neuroblast | SK-N-SH | >10 |
| Thyroid ca | SW1736 | >10 |
| Lung-NSC | NCI-H460 | >10 |
| Pharynx-sqam | FADU | 13.6 |
| Prostate | DU-145 | >10 |

Figure 18:
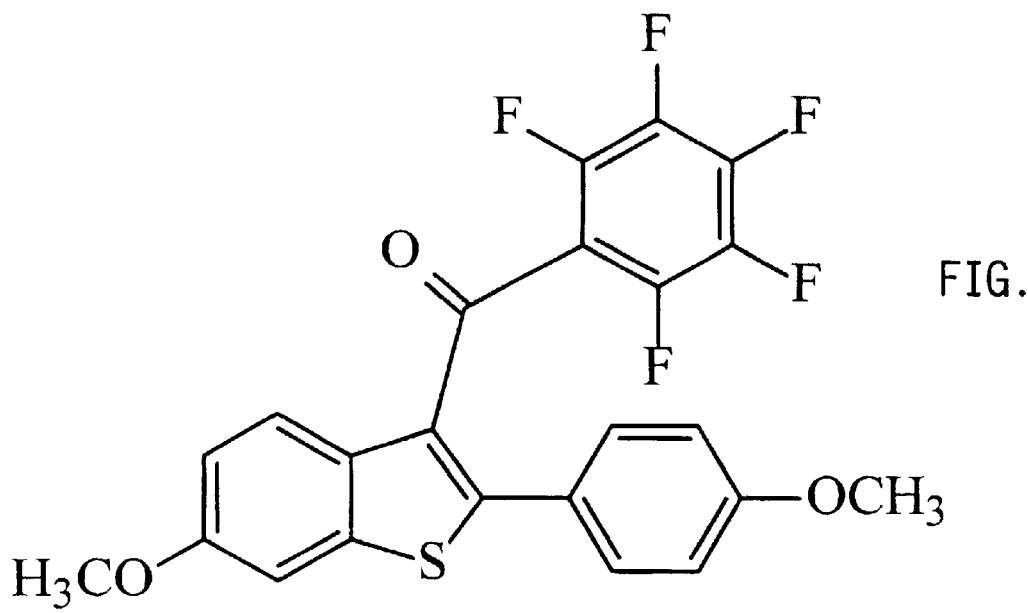
FIG. 18 shows compound 15A, 3-(2', 3', 4', 5', 6'-pentafluorobenzoyl)-2-(4'-methoxyphenyl)-6-methoxybenzo[b]thiophene

Compound 15A—3-(2', 3', 4', 5', 6'-pentafluorobenzoyl)-2-(4'-methoxyphenyl)-6-methoxybenzo[b]thiophene (see FIG. 18) was synthesized as follows.

To a well-stirred solution of 2-(4'methoxyphenyl)-6-methoxybenzo[b]thiophene (0.538 g, 1.989 mmol) and 2, 3, 4, 5, 6-pentafluoro benzoyl chloride (1.000 g, 4.338 mmol) in CH$_2$Cl$_2$ (80 ml) was added AlCl$_3$ (2.147 g, 16.103 mmol) portionwise over a 5 min period. After 4.5 h, water was added, and the product was isolated initially by extraction with CH$_2$Cl$_2$ and subsequently by extraction with EtOAc. The organic layers were washed separately with brine and then combined and dried over MgSO$_4$. Purification by flash chromatography (silica gel, 90:10 hexane/EtOAc then with 80:20 hexane/EtOAc) afforded the desired product (0.5086 g, 60%) as a yellow colored solid. Recrystallization with ethylacetate/hexane mixture, gave highly pure product (0.206 g). $^1$H-NMR (CDCl$_3$, 360 MHz) d 8.47 (d, J=9.0 Hz, 1H, ArH), 7.30 (d, J=2.4 Hz, 1H, ArH), 7.24 (d, J=8.8 Hz, 2H, ArH), 7.16 (dd, J=9.0, 2.2 Hz, 1H, ArH), 6.77 (d, J=8.8, Hz, 2H, ArH), 3.91 (s, 3H, —OCH$_3$), 3.78 (s, 3H, OCH$_3$). HRMS (EI) M$^+$ calc for C$_{23}$H$_{13}$O$_3$SF$_5$ 464.0537, found 464.0506.

Compound 15A shows an inhibition of tubulin polymerization with an IC$_{50}$>40 μM. Biological activity of compound 15A is shown in Table 21.

TABLE 21

Human Cancer Cell Line Studies (Compound 15A)

| Cell Type | Cell Line | GI$_{50}$ (μg/ml) |
|---|---|---|
| Pancreas adn | BXPC-3 | 5.9 |
| Neuroblast | SK-N-SH | 1.4 |
| Thyroid ca | SW1736 | 4.0 |
| Lung-NSC | NCI-H460 | 7.9 |
| Pharynx-sqam | FADU | 1.3 |
| Prostate | DU-145 | 5.0 |

Figure 19:
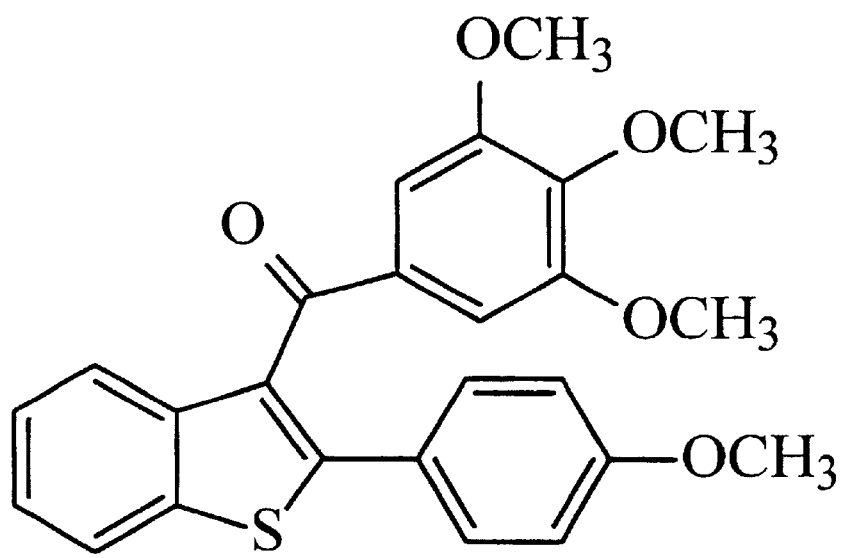
FIG. 19 shows compound 16A, 3-(3', 4', 5'-trimethoxybenzoyl)-2-(4'-methoxyphenyl)-benzo[b]thiophene

Compound 16A—3-(3', 4', 5'-trimethoxybenzoyl)-2-(4'-methoxyphenyl)-benzo[b]thiophene (see FIG. 19) was synthesized as follows:

To a well-stirred solution of 2-(4'-methoxyphenyl)benzo[b]thiophene (0.081 g, 0.32 mmol) and 3,4,5-trimethoxybenzoyl chloride (0.148 g, 0.64 mmol) in CH$_2$Cl$_2$ (15 mL) was added AlCl$_3$ (0.144 g, 1.08 mmol) portion-wise over a 5 minute period. After 3 h 20 min, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 90:10 hexane/EtOAc then with 80:20 hexane/EtOAc) afforded desired benzo[b]thiophene (0.035 g, 26%) as white solid. $^1$H-NMR (CDCl$_3$, 360 MHz) δ 7.87 (m, 1H, ArH), 7.78 (m, 1H, ArH), 7.37 (m, 4H, ArH), 7.07 (s, 2H, ArH), 6.76 (d, J=6.7, 2H, ArH), 3.84 (s, 3H, —OCH$_3$), 3.75 (s, 3H, —OCH$_3$), 3.73 (S, 6H, —OCH$_3$).

Compound 16A shows an inhibition of tubulin polymerization with an IC$_{50}$>40 μM. Biological activity of compound 16A is shown in Table 22.

TABLE 22

Human Cancer Cell Line Studies (Compound 16A)

| Cell Type | Cell Line | GI$_{50}$ (μg/ml) |
|---|---|---|
| Pancreas adn | BXPC-3 | 1.7 |
| Neuroblast | SK-N-SH | 0.83 |
| Thyroid ca | SW1736 | 4.6 |
| Lung-NSC | NCI-H460 | 2.7 |
| Pharynx-sqam | FADU | 0.63 |
| Prostate | DU-145 | 4.8 |

Figure 20:
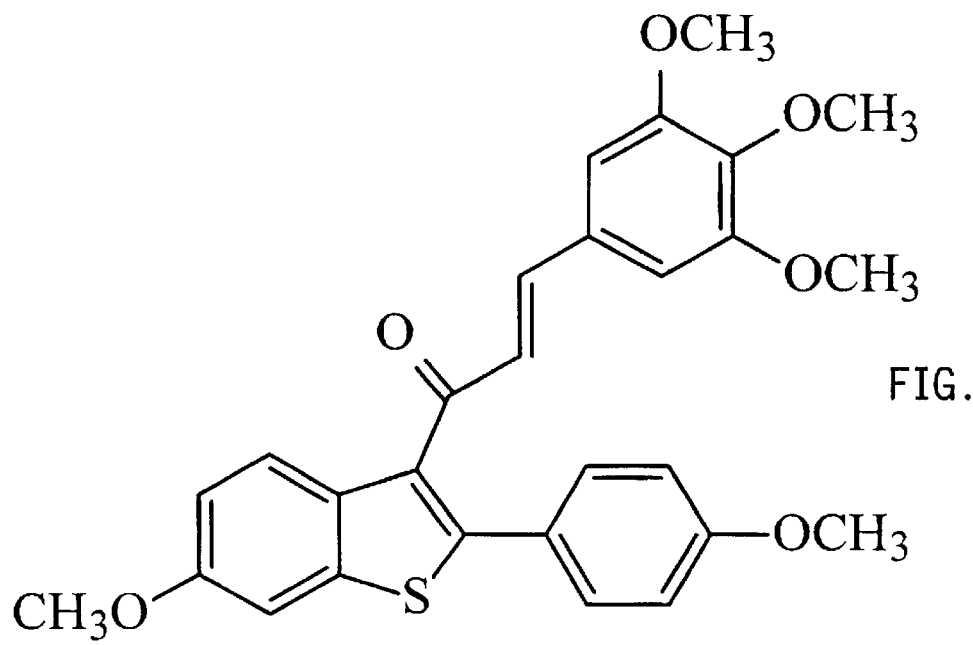
FIG. 20 shows compound 17A, E-3-[3'-(3', 4', 5'-trimethoxyphenyl)cinnamoyl]-2-(4'-methoxyphenyl)-6-methoxybenzo[b]thiophene

Compound 17A—E-3-[3'-(3', 4', 5'-trimethoxyphenyl) cinnamoyl]-2-(4'-methoxyphenyl)-6-methoxybenzo[b] thiophene (see FIG. 20) was synthesized as follows.

To a well stirred solution of 2-(4'-methoxyphenyl)-6-methoxybenzo[b]thiophene (1.006 g, 3.721 mmol) and 3-(3', 4',5'trimethoxy)cinnamoyl chloride (1.834 g, 7.146 mmol) in CH$_2$Cl$_2$ (50 mL) was added AlCl$_3$ (2.093 g, 15.697 mmol) portion-wise over a 15 min period. After 4 h, water was added, and the product was isolated initially by extraction with CH$_2$Cl$_2$ and subsequently by extraction with EtOAc. The organic layers were separately washed with saturated NaHCO$_3$ And then with brine. They were then combined and dried over MgSO$_4$. Purification by flash chromatography (silica gel, 60:40 hexane/EtOAc) afforded the desired product (0.586 g, 1.20 mmol, 32.1%) as a pale yellow solid.

Recrystallization (ethanol/hexane) yielded a highly pure, crystalline sample with an mp=154–155° C. $^1$H-NMR (CDCl$_3$, 360 MHz) d 8.18 (d, J=9.0 Hz, 1H, ArH), 7.5 (d, J=15 Hz, 1H, ArH), 7.49 (dt, J=8.9, 2.2 Hz, 2H, ArH), 7.30 (d, J=2.3 Hz, 1H, ArH), 7.08 (dd, J=9.0, 2.5 Hz, 1H, ArH), 6.95 (dt, J=8.8, 2.1 Hz, 2H, ArH), 6.55 (d, J=15.7 Hz, 1H, ArH), 6.41 (s, 2H, ArH), 3.90 (s, 3H, OCH3), 3.84 (s, 3H, OCH3), 3.80 (s, 3H, OCH3), 3.77 (s, 6H, OCH3); $^{13}$C-NMR (CDCl$_3$, 90 MHz), HRMS (EI) M$^+$ calcd for C$_{28}$H$_{26}$O$_6$S 490.1450, found 490.1300. Anal. Calcd for C$_{28}$H$_{26}$O$_6$S: C, 68.55; H, 5.30; S, 6.54. Found C, 68.57; H, 5.39; S, 6.52.

Compound 17A showed an inhibition of tubulin polymerization with an IC$_{50}$>40 µM. Biological activity of compound 17A is shown in Table 23.

TABLE 23

Human Cancer Cell Line Studies (Compound 17A)

| Cell Type | Cell Line | GI$_{50}$ (µg/ml) |
|---|---|---|
| Pancreas adn | BXPC-3 | 2.3 |
| Neuroblast | SK-N-SH | 1.3 |
| Thyroid ca | SW1736 | 5.2 |
| Lung-NSC | NCI-H460 | 3.9 |
| Pharynx-sqam | FADU | 1.8 |
| Prostate | DU-145 | 7.5 |

Figure 21:
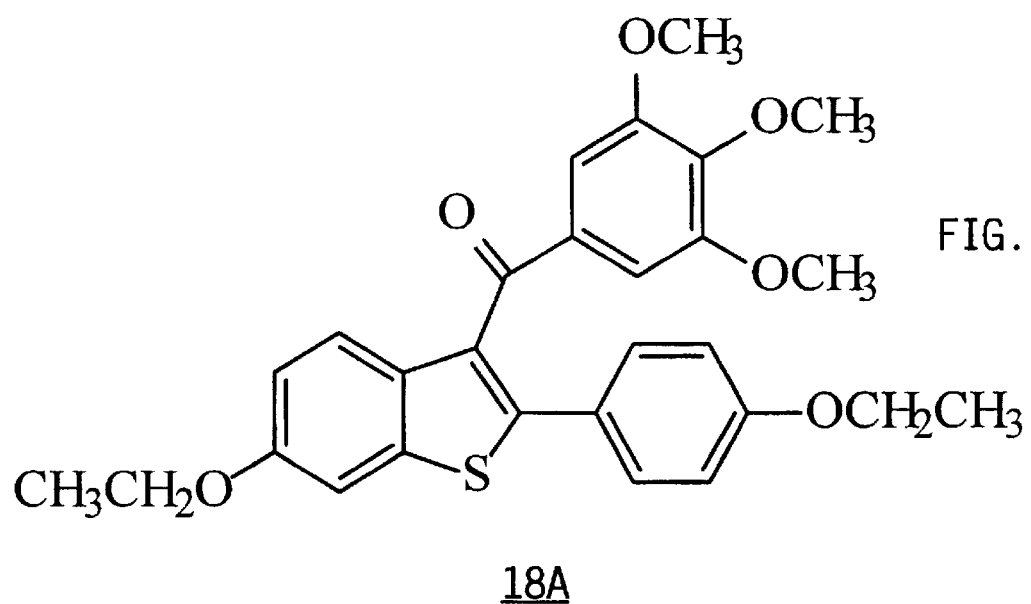
FIG. 21 shows compound 18A, 3-(3', 4', 5'-trimethoxybenzoyl)-2-(4'-ethoxyphenyl)-6-ethoxybenzo[b]thiophene

Compound 18A—3-(3', 4', 5'-trimethoxybenzoyl)-2-(4'-ethoxyphenyl)-6-ethoxybenzo[b]thiophene (see FIG. 21) was synthesized as follows.

To a well-stirred solution of 2-(4'-ethoxyphenyl)-6-ethoxybenzo[b]thiophene (0.095 g, 0.32 mmol) and 3,4,5-trimethoxybenzoyl chloride (0.159 g, 0.69 mmol) in CH$_2$Cl$_2$ (15 mL) was added AlCl$_3$ (0.139 g, 1.04 mmol) portion-wise over a 5 minute period. After 30 min., water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 80:20 hexane/EtOAc) afforded benzo[b]thiophene (0.110 g, 0.2 mmol, 69%) as an off-white solid. $^1$H-NMR (CDCl$_3$, 360 Mhz) δ 7.65 (d, J=8.9 Hz, 1H, ArH), 7.32 (d, J=2.3 Hz, 1H, ArH), 7.29 (d, J=8.8 Hz, 2H, ArH), 7.06 (s, 2H, ArH), 7.00 (dd, J=8.9, 2.4 Hz, 1H, ArH), 6.73 (d, J=8.7 Hz, 2H, ArH), 4.12 (q, J=7.0 Hz, 2H, —CH$_2$), 3.97 (q, J=6.9 Hz, 2H, —CH$_2$), 3.83 (s, 3H, —OCH$_3$), 3.73 (S, 6H, —OCH$_3$), 1.47 (t, J=6.9 Hz, 3H, —CH$_3$), 1.37 (t, J=7.0 Hz, 3H, —CH$_3$).

Compound 18A showed an inhibition of tubulin polymerization with an IC$_{50}$>40 µM. Biological activity of compound 18A is shown in Table 24.

TABLE 24

Human Cancer Cell Line Studies (Compound 18A)

| Cell Type | Cell Line | GI$_{50}$ (µg/ml) |
|---|---|---|
| Pancreas adn | BXPC-3 | 1.6 |
| Neuroblast | SK-N-SH | 0.33 |
| Thyroid ca | SW1736 | 2.3 |
| Lung-NSC | NCI-H460 | 1.4 |
| Pharynx-sqam | FADU | 0.60 |
| Prostate | DU-145 | 3.6 |

Figure 22:
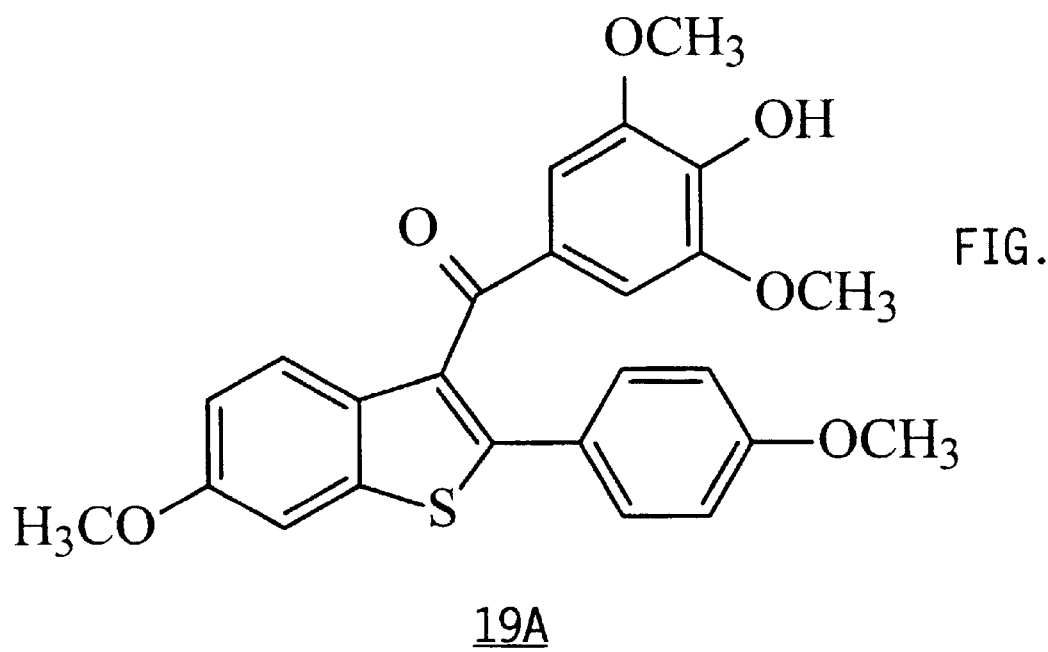
FIG. 22 shows compound 19A, 3-(4'-hydroxy-3',5'-dimethoxybenzoyl)-2-(4'-methoxyphenyl)-6-methoxybenzo[b]thiophene

Compound 19A—3-(4'-hydroxy-3',5'-dimethoxybenzoyl)-2-(4'-methoxyphenyl)-6-methoxybenzo[b]thiophene (see FIG. 22) was synthesized as follows.

To a well-stirred solution of 2-(4'-methoxyphenyl)-6-methoxybenzo[b]thiophene (0.250 g, 0.925 mmol) and 3,4,5-trimethoxybenzoyl chloride (0.320 g, 1.39 mmol) in CH$_2$Cl$_2$ (20 mL) was added AlCl$_3$ (0.925 g, 6.94 mmol) portion-wise over a 15 min period. After 20 h, water was added, and the product was isolated initially by extraction with CH$_2$Cl$_2$ and subsequently by extraction with EtOAc. The organic layers were separately washed with brine and then combined and dried over MgSO$_4$. Purification by flash chromatography (silica gel, 60:40 EtOAc/hexane) followed by recrystallization (hexane/ethanol) afforded a highly pure, crystalline sample of 2 (0.018 g, 0.040 mmol) with mp=142–143° C. $^1$H-NMR (CDCl$_3$, 360 MHz) d 7.62 (dd, J=8.9, 0.3 Hz, 1H, ArH), 7.33 (d, J=8.9 Hz, 2H, ArH), 7.33 (d, J=2.5 Hz, 1H, ArH), 7.12 (s, 2H, ArH), 7.00 (dd, J=8.9, 2.4 Hz, 1H, ArH), 6.76 (d, J=8.9 Hz, 2H, ArH), 5.90 (s, 1H, —OH), 3.89 (s, 3H, —OCH$_3$), 3.77 (s, 6H, —OCH$_3$), 3.76 (s, 3H, —OCH$_3$); $^{13}$C-NMR (CDCl$_3$, 90 MHz) d 192.7, 159.9, 157.8, 146.6, 142.9, 140.2, 139.9, 134.1, 130.3, 130.1, 128.7, 126.2, 124.2, 114.9, 114.2, 107.5, 104.5, 56.4, 55.7, 55.3. HRMS (EI) M$^+$ calcd for C$_{25}$H$_{22}$O$_6$S 450.1137, found 450.1139. Anal. Calcd for C$_{25}$H$_{22}$O$_6$S: C, 66.65; H, 4.92; S, 7.12. Found: C, 66.52; H, 5.01; S, 6.97.

Table 25 shows biological activity of compound 19A.

TABLE 25

P388 Leukemia Data (Compound 19A)

| Cell Type | Cell Line | ED$_{50}$ (µg/ml) |
|---|---|---|
| Mouse Leukemia | P388 | >100 |

Figure 23:
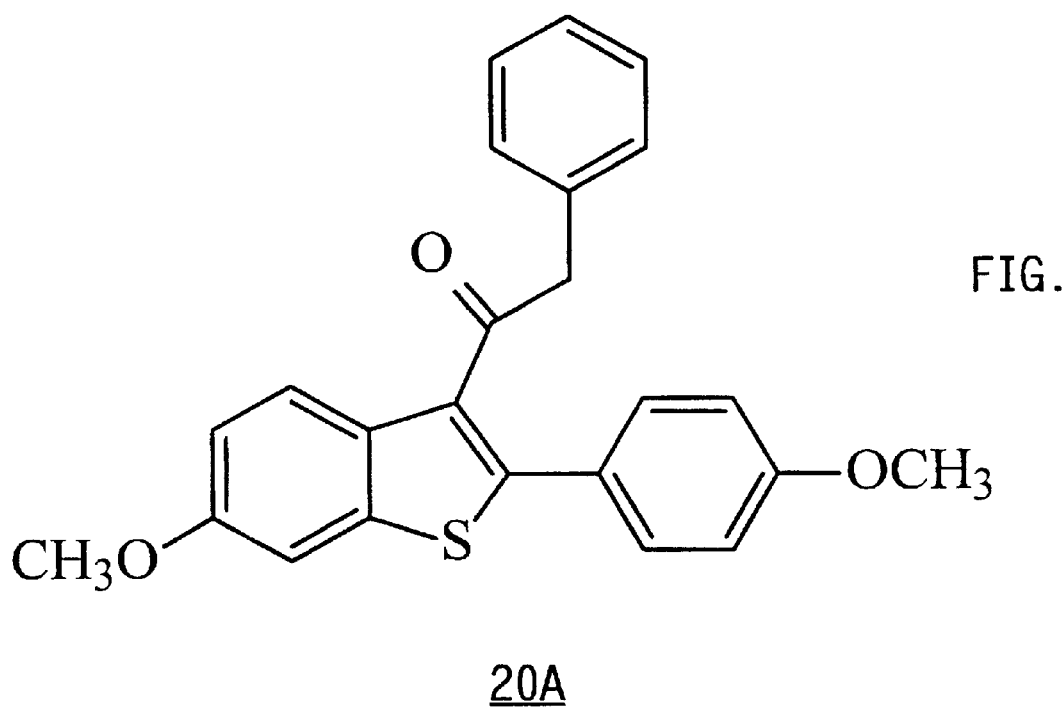
FIG. 23 shows compound 20A, 3-(phenylacetyl)-2-(4'-methoxyphenyl)-6-methoxybenzo[b]thiophene

Compound 20A—3-(phenylacetyl)-2-(4'-methoxyphenyl)-6-methoxybenzo[b]thiophene (see FIG. 23) was synthesized as follows.

To a well stirred solution of 2-(4'-methoxyphenyl)-6-methoxybenzo[b]thiophene (0.452 g, 1.67 mmol) and phenylacetyl chloride (0.52 g, 3.34 mmol) in CH$_2$Cl$_2$ (50 mL) was added AlCl$_3$ (0.670 g, 5.02 mmol) portion-wise over a 15 min period. After 1½ h (total reaction time), water was added, and the product was isolated initially by extraction with CH$_2$Cl$_2$ and subsequently by extraction with EtOAc. The organic layers were separately washed sequentially with NaHCO$_3$ and brine and then dried over MgSO$_4$. Purification by flash chromatography (silica gel, 70:30 hexane/EtOAc) afforded benzo[b]thiophene 2 (0.11 g, 0.29 mmol, 17.1%) as a white solid. Recrystallization (Ethanol/hexane) yielded a highly pure, crystalline sample. $^1$H-NMR (CDCl$_3$, 360 MHz) d 7.87 (d, J=9 Hz, 1H, ArH), 7.45 (td, J=8.82, 2.16 Hz, 2H, ArH), 7.2 (m, 4H, ArH), 7.0 (m, 5H, ArH), 3.88 (s, 3H, —OCH$_3$), 3.86 (s, 3H, —OCH$_3$), 3.73 (s, 2H, CH$_2$).

Tables 26 and 27 show biological activity of compound 20A.

TABLE 26

P388 Leukemia Data (Compound 20A)

| Cell Type | Cell Line | ED$_{50}$ (µg/ml) |
|---|---|---|
| Mouse Leukemia | P388 | >10 |

TABLE 27

Human Cancer Cell Line Studies (Compound 20A)

| Cell Type | Cell Line | $GI_{50}$ (μg/ml) |
|---|---|---|
| Pancreas adn | BXPC-3 | >10 |
| Melanoma | RPMI-7951 | >10 |
| CNS | U251 | >10 |
| Lung-NSC | NCI-H460 | >10 |
| Pharynx-sqam | FADU | 9.2 |
| Prostate | DU-145 | >10 |

Figure 24:
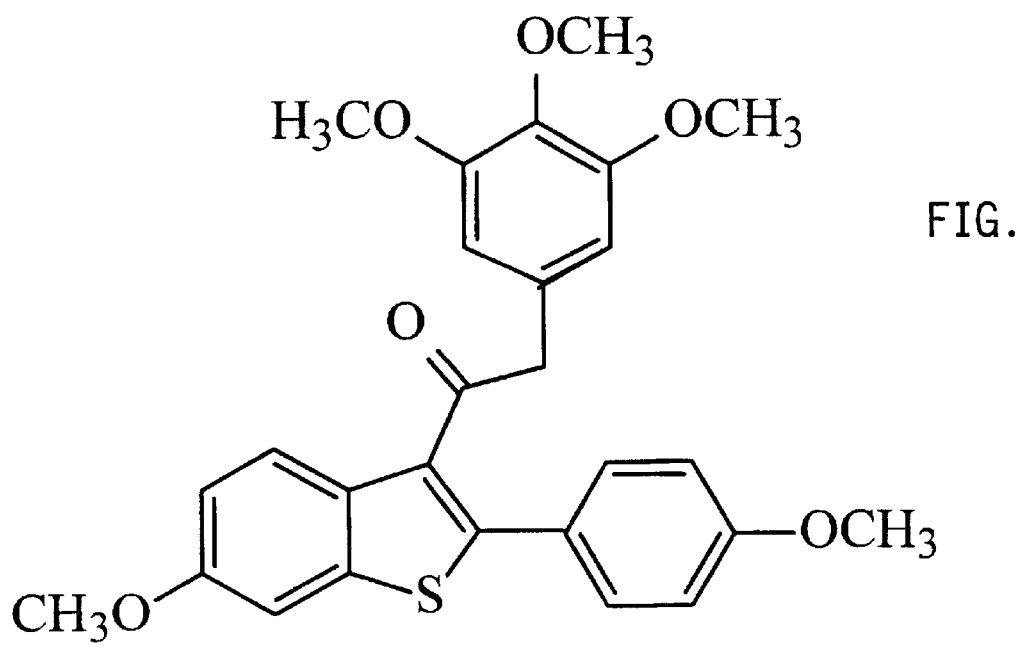
FIG. 24 shows compound 21A, 3-(3', 4', 5'-trimethoxy)phenylacetyl)-2-(4'-methoxyphenyl)-6-methoxybenzo[b]thiophene

Compound 21A—3-(3', 4', 5'-trimethoxy)phenylacetyl)-2-(4'-methoxyphenyl)-6-methoxybenzo[b]thiophene (see FIG. 24) was synthesized as follows.

To a well stirred solution of 2-(4'-methoxyphenyl)-6-methoxybenzo[b]thiophene (0.302 g, 1.12 mmol) and 3',4',5'trimethoxyphenyl acetyl chloride (0.541 g, 2.21 mmol) in $CH_2Cl_2$ (40 mL) was added $AlCl_3$ (0.600 g, 4.50 mmol) portion-wise over a 15 min period. After 4½ h, water was added, and the product was isolated initially by extraction with $CH_2Cl_2$ and subsequently by extraction with EtOAc. The organic layers were separately washed with $NaHCO_3$ (sat) and brine, and then combined and dried over $MgSO_4$. Purification by flash chromatography (silica gel, 60:40 hexane/EtOAc) afforded benzo[b]thiophene 3 (0.470 g, 0.99 mmol, 88.7%) as a white solid. Recrystallization (ethanol/hexane) yielded a highly pure, crystalline solid with an mp=117–118° C.

$^1$H-NMR ($CDCl_3$, 360 MHz) d 7.89 (d, J=9 Hz, 1H, ArH), 7.43 (td, J=8.82, 2.16 Hz, 2H, ArH), 7.25 (d, J=2.3 Hz, 1H, ArH), 7.0 (m, 3H, ArH), 6.15 (s, 2H, ArH), 3.88 (s, 3H, —$OCH_3$), 3.87 (s, 3H, —$OCH_3$), 3.77 (s, 3H, —$OCH_3$), 3.72 (s, 6H, —$OCH_3$), 3.66 (s, 2H, $CH_2$) $^{13}$C-NMR($CDCl_3$, 90 Mhz) 198.9, 160.6, 157.8, 153.0, 145.6, 140.0, 132.8, 130.9, 129.8, 126.1, 124.5, 115.2, 114.5, 106.4, 104.2, 60.8, 56.0, 55.6, 55.4, 49.9. HRMS (EI) $M^+$ calcd for $C_{27}H_{26}O_6S$ 478.1450, found 478.1609. Anal. Calcd for $C_{27}H_{26}O_6S$: C, 67.77; H, 4.48; S, S, 6.70. Found C, 67.85; H, 5.55; S, 6.73.

Tables 28 and 29 show biological activity of compound 21A.

TABLE 28

P388 Leukemia Data (Compound 21A)

| Cell Type | Cell Line | $ED_{50}$ (μg/ml) |
|---|---|---|
| Mouse Leukemia | P388 | >10 |

TABLE 29

Human Cancer Cell Line Studies (Compound 21A)

| Cell Type | Cell Line | $GI_{50}$ (μg/ml) |
|---|---|---|
| Pancreas adn | BXPC-3 | 9.8 |
| Melanoma | RPMI-7951 | >10 |
| CNS | U251 | >10 |
| Lung-NSC | NCI-H460 | >10 |
| Pharynx-sqam | FADU | 7.9 |
| Prostate | DU-145 | >10 |

EXAMPLE 2

DIARYL-ETHER benzo[b]thiophene DERIVATIVES

The following two compounds have been prepared by chemical synthesis and one of them has been evaluated in terms of its biological efficacy. The biological results on the other derivative are forthcoming.

Figure 25:
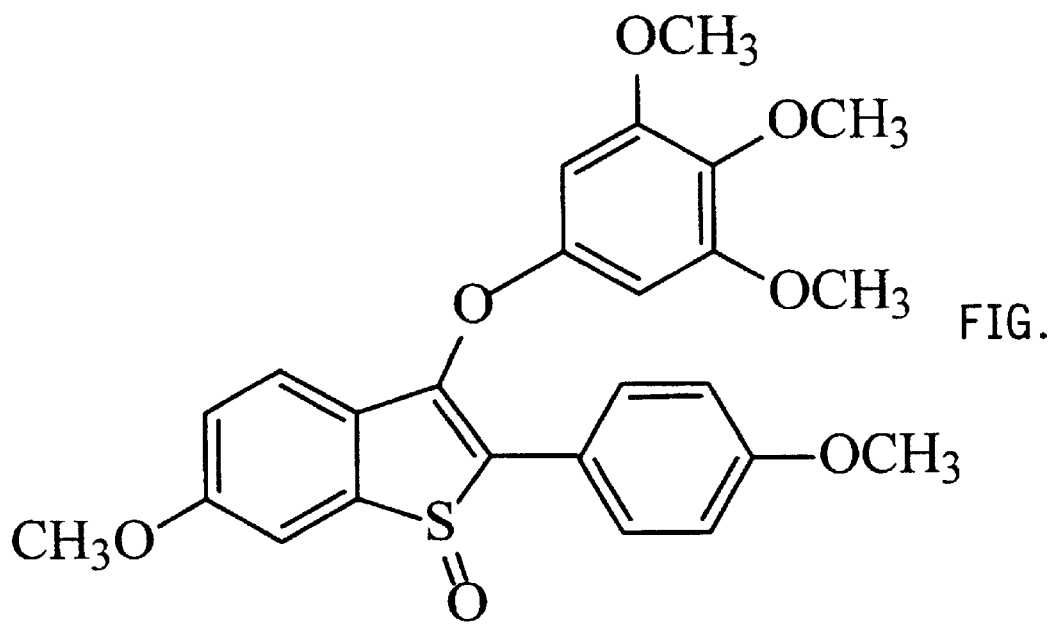
FIG. 25 shows compound 22B, 3-(3',4',5'-trimethoxyphenoxy)-2-(4'-methoxyphenyl)-6-methoxybenzo[b]thiophene S-oxide

Compound 22B—3-(3',4',5'-trimethoxyphenoxy)-2-(4'-methoxyphenyl)-6-methoxybenzo[b]thiophene S-oxide (see FIG. 25) was synthesized as follows.

To a well stirred solution of 3,4,5-trimethoxyphenol (0.081 g, 0.44 mmol) in DMF (5 ml) was added NaH (0.020 g, 0.84 mmol) and stirred at room temperature for 15 min followed by the addition of a mixture of 3,7-dibromo and 3-bromo -2-(4'-methoxyphenyl)-6-methoxybenzo[b]thiophene-S-oxide (0.150 g, 0.35 mmol). After 2 h the reaction mixture is partitioned between 10% ethanol-ethylacetate mixture and water. The aqueous phase was extracted 3× with 10% ethanol solution. Washing the organic layer with water (5×) followed by brine, drying over $MgSO_4$ and evaporation of the solvent gave a dark colored oil. Trituration of the residue with ether and hexane mixture resulted in desired products as a yellow fluffy solid. $^1$H-NMR ($CDCl_3$, 300 MHz) δ 7.65 (d, J=8.9 Hz, 2H, ArH), 7.34 (d, J=2.3 Hz, 1H, ArH), 7.22 (d, J=8.5 Hz, 1H, ArH), 6.99 (dd, J=8.6, 2.4 Hz, 1H, ArH), 6.86 (d, J=8.9, 2 H, ArH), 6.29 (s, 2H, ArH), 3.89 (s, 3H, —$OCH_3$), 3.79 (s, 3H, —$OCH_3$), 3.76 (s, 3H, —$OCH_3$), 3.75 (s, 6H, —$OCH_3$).

Figure 26:
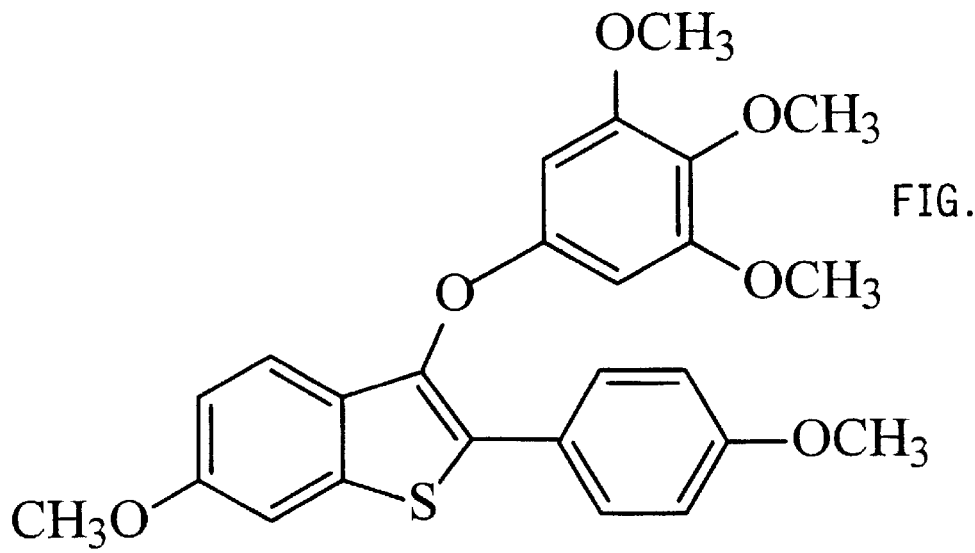
FIG. 26 shows compound 23B, 3-(3',4',5'-trimethoxyphenoxy)-2-(4'-methoxyphenyl)-6-methoxybenzo[b]thiophene

Compound 23B—3-(3',4',5'-trimethoxyphenoxy)-2-(4'-methoxyphenyl)-6-methoxybenzo[b]thiophene (see FIG. 26) was synthesized as follows.

To an ice cooled, well stirred solution of mixture of 3-(3',4',5'-trimethoxyphenoxy)-2-(4'-methoxyphenyl)-6-methoxybenzo[b]thiophene S-oxide and 7-bromo-3-(3',4',5'-trimethoxyphenoxy)-2-(4'-methoxyphenyl)-6-methoxybenzo[b]thiophene S-oxides (0.183 g, 0.34 mmol) in THF (10 ml) was added lithium aluminum hydride (0.028 g, 0.72 mmol). After 1.5 h, the reaction was quenched with water followed by usual work up with ethyl acetate, brine and dried over $MgSO_4$. Removal of the solvent followed by purification by flash chromatography (80:20 hexanes:ethylacetate) resulted in desired product (0.011 g, 0.025 mmol) as a white colorless solid with an mp=129–131° C. $^1$H-NMR ($CDCl_3$, 300 Mhz) δ 7.66 (d, J=8.9 Hz, 2H, ArH), 7.31 (d, J=8.7 Hz, 1H, ArH), 7.25 (d, J=2.2 Hz, 1H, ArH), 6.91 (d, J=9.0 Hz, 2H, ArH), 6.90 (dd, J=8.8, 2.3 Hz, 1H, ArH), 6.21 (s, 2H, ArH, 3.88 (s, 3H, —$OCH_3$), 3.82 (s, 3H, —$OCH_3$), 3.78 (s, 3H, —$OCH_3$), 3.71 (s, 6H, —$OCH_3$). HRMS (EI) $M^+$ calcd for $C_{25}H_{24}O_6S$ 452.1248, found 452, 1294. Anal. Calcd for $C_{25}H_{24}O_6S$: C, 66.36; H, 5.35; S, 7.08. Found: C, 65.12; H, 5.39; S, 6.96.

HRMS (EI) $M^+$ calcd for $C_{25}H_{24}O_6S$ 452.1248, found 452.1294. Anal. Calcd for $C_{25}H_{24}O_6S$: C, 66.36; H, 5.35; S, 7.08. Found: C, 65.12; H, 5.39; S, 6.96.

The biological activity of compound 23B was measured as seen in Tables 30 and 31. The inhibition of tubulin polymerization by compound 23 B gave an $IC_{50}$=1.4 μM.

TABLE 30

P388 Leukemia Data (Compound 23B)

| Cell Type | Cell Line | $ED_{50}$ (μg/ml) |
|---|---|---|
| Mouse Leukemia | P388 | 3.09 |

TABLE 31

Human Cancer Cell Line Studies (In Vitro) (Compound 23B)

| Cell Type | Cell Line | GI$_{50}$ ($\mu$g/ml) |
|---|---|---|
| Pancreas adn | BXPC-3 | 0.23 |
| Neuroblast | SK-N-SH | 0.063 |
| Thyroid ca | SW1736 | 0.73 |
| Lung-NSC | NCI-H460 | 0.31 |
| Pharynx-sqam | FADU | 0.098 |
| Prostate | DU-145 | 0.42 |

Significant biological activity is expected for the as yet untested compound based on the prevalence of such activity for compounds 23B and the compounds described in other Examples.

It will be apparent to anyone skilled in the art that the experimental procedures used to prepare the benzo[b]thiophene derivatives (Example 1 and 1A) can be suitably modified to incorporate a wide-variety of alkoxy groups and substitution patterns.

In addition, the availability of the vinyl bromide used as a precursor in the preparation of diaryl ether derivatives (22B and 23B—Example 2) provides a myriad of reaction possibilities for the preparation of related derivatives. For example, the vinylbromide may undergo halogen-metal exchange to form a very nucleophilic vinyl-metal species which will prove very reactive with a wide variety of electrophiles (most notably carbonyl groups). The vinylbromide may also be subject to direct attack by organocuprate reagents which upon 1,4 addition and subsequent elimination of bromide, will render new compounds which are substituted at the 3-position of the benzo[b]thiophene core structure. This should be especially useful for installing aryl groups (both substituted and unfunctionalized) directly on the 3-position of the benzo[b]thiophene core structure.

EXAMPLE 3

BENZOFURAN DERIVATIVES

Figure 27:
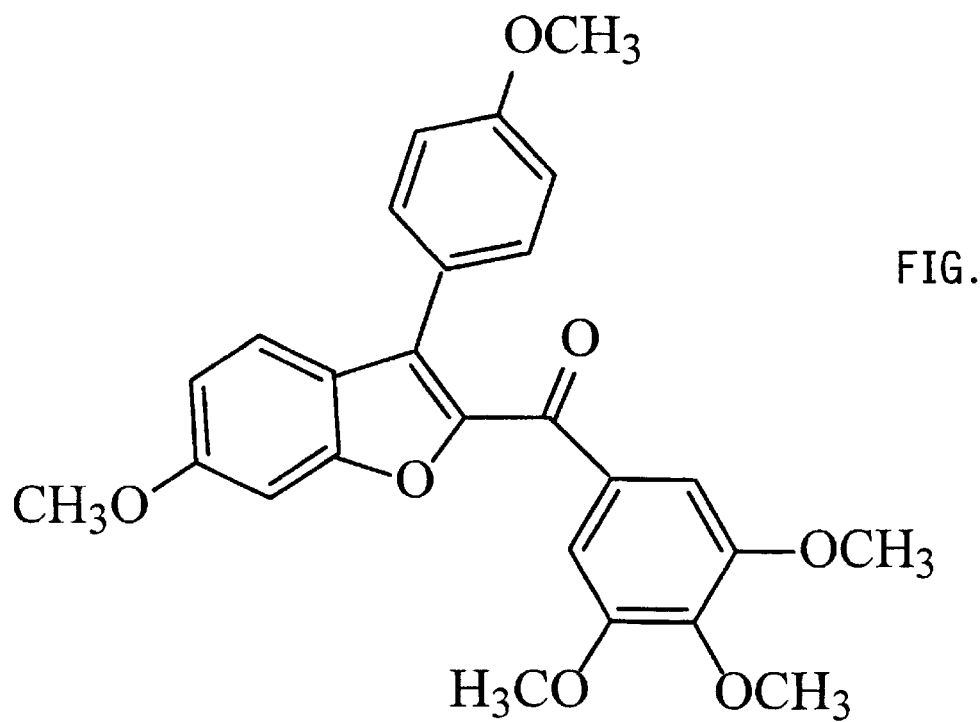
FIG. 27 shows compound 24C, 3-(3',4',5'-trimethoxybenzoyl)-2-(4'-methoxyphenyl)-6-methoxybenzo[b]furan

Compound 24C—3-(3',4',5'-trimethoxybenzoyl)-2-(4'-methoxyphenyl)-6-methoxybenzo[b]furan (see FIG. 27) was prepared as follows.

To a well-stirred solution of 2-(4'methoxyphenyl)-6-methoxybenzo[b]furan (1.104 g, 0.409 mmol) and 3, 4, 5-trimethoxybenzoyl chloride (0.195 g, 0.846 mmol) in CH$_2$Cl$_2$ (25 ml) was added AlCl$_3$ (0.169 g, 1.270 mmol) portionwise over a 5 min period. After 3 h, water was added, and the product was isolated initially by extraction with CH$_2$Cl$_2$ and subsequently by extraction with EtOAc. The organic layers were washed separately with brine and then combined and dried over MgSO$_4$. Purification by flash chromatography (silica gel, 90:10 hexane/EtOAc then with 80:20 hexane/EtOAc) afforded a highly pure sample of the desired product (0.045 g, 25%) as a yellow colored liquid. $^1$H-NMR (CDCl$_3$, 360 MHz) d 7.58 (d, J=8.8 Hz, 1H, ArH), 7.39 (d, J=8.9 Hz, 2H, ArH), 7.12 (s, 2H, ArH), 7.10 (d, J=2.2 Hz, 1H, ArH), 6.98 (dd, J=8.8, 2.2 Hz, 1H, ArH), 6.89 (d, J=8.9 Hz, 2H, ArH), 3.91 (s, 3H, —OCH$_3$), 3.87 (s, 3H, OCH$_3$), 3.81 (s, 3H, —OCH$_3$), 3.79 (s, 3H, —OCH$_3$). $^{13}$C-NMR (CDCl$_3$, 90 MHz) $\delta$ 184.2, 161.1, 159.6, 156.1, 152.6, 146.3, 141.9, 132.5, 131.2, 129.7, 123.4, 122.8, 121.4, 114.2, 113.8, 107.3, 95.4, 60.9, 56.1, 55.8, 55.3. HRMS (EI) M$^+$ calc for C$_{26}$H$_{24}$O$_7$ 448.1522, found 448.1522. Anal. Calcd for C$_{26}$H$_{24}$O$_7$: C, 69.63; H, 5.39. Found: C, 69.56; H, 5.33.

Compound 24C had the biological activity shown in Table 32. Compound 24C showed inhibition of tubulin polymerization with an IC$_{50}$=2.1 $\mu$M (totally flat at 4 $\mu$M).

TABLE 32

Human Cancer Cell Line Studies (Compound 31C)

| Cell Type | Cell Line | GI$_{50}$ ($\mu$g/ml) |
|---|---|---|
| Pancreas adn | BXPC-3 | 0.038 |
| Neuroblast | SK-N-SH | 0.025 |
| Thyroid ca | SW1736 | 0.047 |
| Lung-NSC | NCI-H460 | 0.041 |
| Pharynx-sqam | FADU | 0.035 |
| Prostate | DU-145 | 0.062 |

EXAMPLE 4

DIHYDRONAPHTHALENE DERIVATIVES

Figure 28:
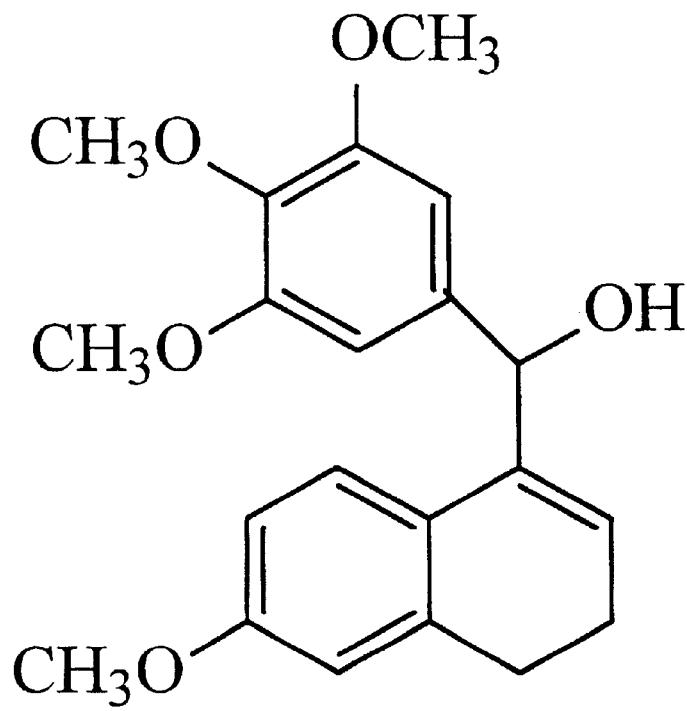
FIG. 28 shows compound 25D, 1-(hydroxymethyl-3',4', 5'-trimethoxyphenyl)-6-methoxy-3,4-dihydronaphthalene

Compound 25D—1-(hydroxymethyl-3',4',5'-trimethoxyphenyl)-6-methoxy-3,4-dihydronaphthalene (see FIG. 28), was prepared as follows.

To a well stirred solution of tetramethylethylenediamine (20 mL) and BuLi (4.6 mL of 2.5 M solution in hexane, 11.500 mmol) cooled to –50° C. in dry ice/acetone bath was added 6-methoxy-3,4-dihydro-1(2H)-naphthalene p-toluenesulfonylhydrazone (1.008 g, 2.927 mmol) and stirred at that temperature for 30 min. It was then allowed to warm to room temperature and stirred at room temperature for 30 min. The reaction mixture was cooled to 0° C. in ice water, followed by the addition of 3,4,5-trimethoxybenzaldehyde (2.279 g, 11.616 mmol). After 1 h of stirring at 0° C., the reaction was quenched with water, extracted with ethylacetate. The organic layer was washed with aqueous copper sulfate solution followed by brine and dried over MgSO$_4$. Purification of the compound by flash chromatography yielded the desired product as thick yellow oil (0.2897 mg, 0.8128 mmol) in 28% yield which solidified upon keeping it in the refrigerator. 1H-NMR (CDCl$_3$, 360 MHz) d 7.19 (d, J=8.6 Hz, 1H, ArH), 6.72 (d, J=2.65, 1H, ArH), 6.68 (s, 2H, ArH), 6.6 (dd, J=2.7, 8.5 Hz, 1H, ArH), 6.02 (t, J=4.7 Hz, 1H, CH), 5.67 s, 1H, CH), 3.84 (s, 6H, OCH$_3$), 3.83 (s, 3H, OCH$_3$), 3.78 (s, 3H, OCH$_3$), 2.75 (t, J=7.7 Hz, 2H, CH$_2$), 2.34 (m, 2H, CH$_2$). $^{13}$C-NMR (CDCl$_3$, 90 MHz) d 157.9, 152.7, 138.2, 138.1, 137.6, 136.7, 125.8, 124.6, 124.4, 113.4, 110.4, 103.6, 73.7, 60.3, 55.6, 54.7, 28.3, 22.6. HRMS (EI) M$^+$ calc for C$_{21}$H$_{24}$O$_5$ 356.4, found mp=89–92° C.

Certain biological activity of compound 25D is shown in Table 33. Compound 25D showed inhibition of tubulin polymerization with an IC$_{50}$>40 $\mu$M.

TABLE 33

Human Cancer Cell Line Studies (Compound 25D)

| Cell Type | Cell Line | GI$_{50}$ ($\mu$g/ml) |
|---|---|---|
| Pancreas adn | BXPC-3 | 0.53 |
| Neuroblast | SK-N-SH | 0.30 |
| Thyroid ca | SW1736 | 2.1 |
| Lung-NSC | NCI-H460 | 1.5 |
| Pharynx-sqam | FADU | 0.51 |
| Prostate | DU-145 | 2.6 |

Figure 29:
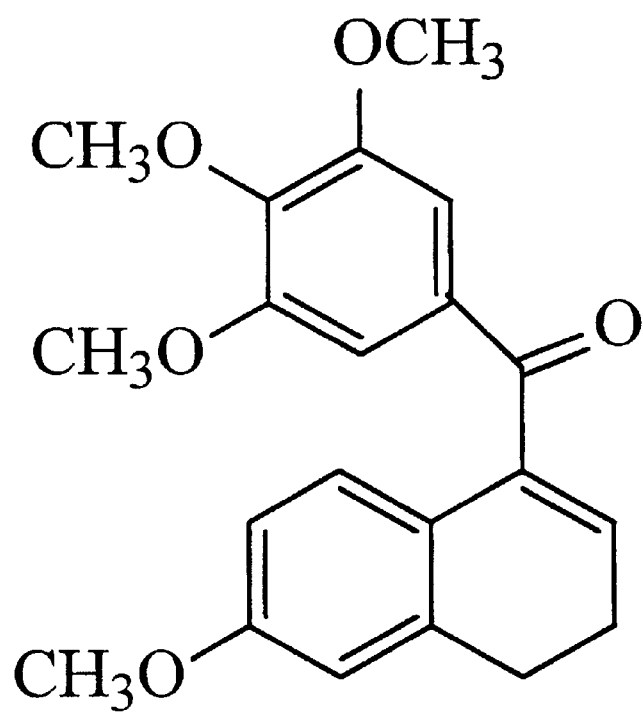
FIG. 29 shows compound 26D, 1-(3',4',5'-trimethoxybenzoyl)-6-methoxy-3,4-dihydronaphthalene

Compound 26D—1-(3',4',5'-trimethoxybenzoyl)-6-methoxy-3,4-dihydronaphthalene (see FIG. 29) was prepared as follows.

To a well stirred solution of Dess-martin reagent (0.313 g, 0.736 mmol) in CH$_2$Cl$_2$ (10 ml) was added 6-methoxy-3,4-dihydronaphthyl-3,4,5-trimethoxyphenyl-methanol (0.050 g, 0.140 mmol). After 2 h water was added and the suspension was partitoned between 1.3 M NaOH (20 mL) and CH$_2$Cl$_2$ (50 mL) and the organic layer was washed with more of NaOH (20 mL, 1.3 M) followed by many times with water, once with brine and dried over MgSO$_4$. Purification by flash chromatography (silica gel, 80:20 hexane/EtOAc) afforded a highly pure sample of the desired product (0.0495 g, 99.6%) as an yellow colored solid. $^1$H-NMR (CDCl$_3$, 360 MHz) d 7.19 (d, J=8.5 Hz, 1H, ArH), 7.15 (s, 2H, ArH), 6.77 (d, J=2.5 Hz, 1H, ArH), 6.70 (dd, J=2.6, 8.5 Hz, 1H, ArH), 6.35 (t, J=4.7 Hz, 1H, ArH), 3.92 (s, 3H, OCH$_3$), 3.86 (s, 6H, OCH$_3$), 3.81 (s, 3H, OCH$_3$), 2.86 (t, J=7.8 Hz, 2H, CH$_2$), 2.49 (m, 2H, CH$_2$). $^{13}$C-NMR (CDCl$_3$, 90 MHz) d 196.1, 159.2, 152.9, 142.5, 138.3, 137.6, 133.0, 132.9, 126.9, 125.2, 114.0, 111.3, 107.6, 60.9, 56.3, 55.2, 28.1, 23.1. HRMS (EI) M$^+$ calc for C$_{21}$H$_{22}$O$_5$ 354.1467, found 354.0859.

Certain biological activity of compound 26D is shown in Table 34. Compound 26D showed inhibition of tubulin polymerization with an IC$_{50}$=1.7 μM (total flat at 4 μM).

TABLE 34

Human Cancer Cell Line Studies (Compound 26D)

| Cell Type | Cell Line | GI$_{50}$ (μg/ml) |
|---|---|---|
| Pancreas adn | BXPC-3 | 0.003 |
| Neuroblast | SK-N-SH | <0.001 |
| Thyroid ca | SW1736 | 0.0048 |
| Lung-NSC | NCI-H460 | 0.0033 |
| Pharynx-sqam | FADU | 0.0013 |
| Prostate | DU-145 | 0.0038 |

It will be apparent to anyone skilled in the art that the experimental procedures used to prepare the dihydronaphthalene derivatives 25D and 26D (Example 4) can be readily modified by appropriate substrate choice to prepare a wide variety of 3,4-dihydronaphthalene derivatives. For example, treating the vinyl-lithium intermediate (generated in situ) with 3,4,5-triethoxybenzaldehyde (instead of 3,4,5-trimethoxybenzaldehyde) will result in the preparation of ethoxylated ligands. This example can similarly be applied to the preparation of numerous other alkoxy dihydronaphthalene derivatives.

In addition, oxidation of the secondary alcohol to a ketone moiety (as in the conversion of 25D to 26D) renders a molecule (like 26D) which contains an α,β-unsaturated ketone will readily undergo 1,4 addition by organocuprate reagents to generate new tetralin compounds which are substituted at both the 1 and 2-positions. This establishes the requisite protocol to install a wide variety of groups (alkyl, vinyl, aryl) both substituted with alkoxy or halogen moieties, and unfunctionalized. These 1,2-disubstituted tetralins can also be treated with organoselenium reagents followed by oxidation and elimination to regenerate the 3,4-dihydronaphthalene core structure (with substituents now at both the 1 and 2 positions).

EXAMPLE 5

NITROGEN ANALOGS OF COMBRETASTATIN

Combretastatins are seen in U.S. Pat Nos. 5,409,953 (Pettit et al.), 5,561,122 (Pettit), 4,996,237 (Pettit et al.), and 4,940,726 (Pettit et al.). Related compounds are seen in U.S. Pat. No. 5,430,062 (Cushman et al.).

Figure 30:
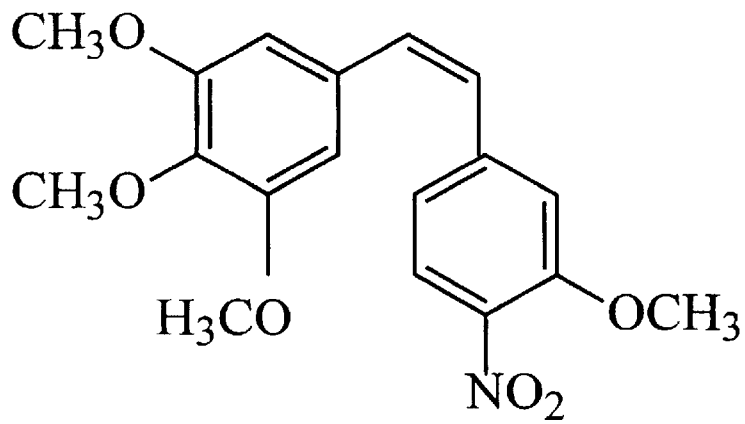
FIG. 30 shows compound 27E, (Z)-1-(3'-methoxy-4'-nitrophenyl)-2-(3",4",5"-trimethoxyphenyl) ethene
Figure 31:
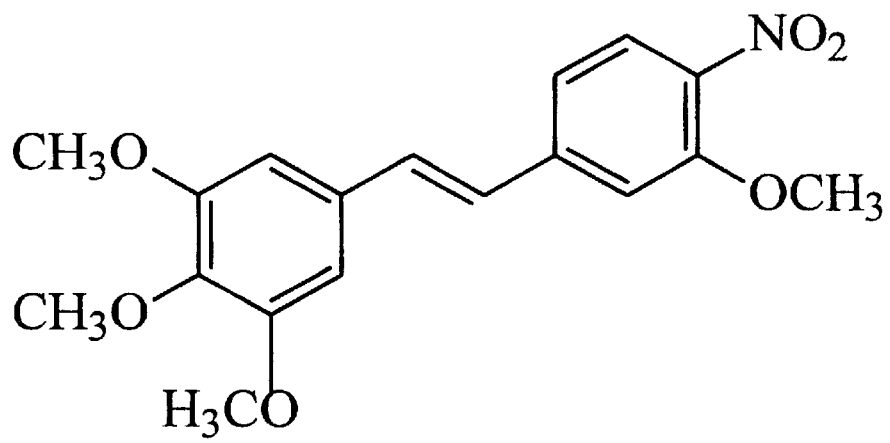
FIG. 31 shows compound 28E, (E)-1-(3'-methoxy-4'-nitrophenyl)-2-(3",4",5"-trimethoxyphenyl) ethene

Compounds 27E and 28E—(E/Z)-1-(3'-methoxy-4'-nitrophenyl)-2-(3",4",5"-trimethoxyphenyl) ethene (see FIG. 30 and FIG. 31), isomeric compounds, were prepared as follows.

A solution of 3,4,5-trimethoxybenzyltriphenylphosphonium bromide 1 (1.50 g, 2.86 mmol) and 3-methoxy-4-nitrobenzaldehyde 2 (0.518 g, 2.86 mmol) in CH$_2$Cl$_2$ (50 mL) was stirred under a nitrogen atmosphere. After 30 min, NaH (0.412 g, 17.16 mmol) was added. After 16 h, water was added and the product was isolated by extraction with CH$_2$Cl$_2$. The organic phase was washed with brine and dried over MgSO$_4$. The solvent was removed under reduced pressure to afford ethene 3 as a mixture of isomers (Z/E: 1.46/1.00 as determined by careful integration of $^1$H-NMR signals).

Purification and characterization of (Z) isomer, compound 27E, was done as follows. Purification by flash chromatography (silica gel, 70:30 hexanes:ethyl acetate) afforded (Z)-ethene 27E (0.319 g, 0.923 mmol, 32%) as a bright yellow solid. Recrystallization (hexanes/CH$_2$Cl$_2$) afforded an analytically pure sample of ethene 27E, mp=83–85° C. $^1$H-NMR (CDCL$_3$, 360 MHz) d 7.80 (d, J=8.4 Hz, 1H, ArH), 6.98 (d, J=1.3 Hz, 1H, ArH), 6.95 (dd, J=8.6 Hz, 1.4 Hz, 1H, ArH), 6.72 (d, J=12.1, 1H, vinyl CH), 6.54 (d, J=12.1, 1H, vinyl CH), 6.46 (s, 2H, ArH), 3.84 (s, 3H, OCH$_3$), 3.77 (s, 3H, OCH$_3$), 3.71 (s, 6H, OCH$_3$); $^{13}$C-NMR (CDCL$_3$, 90 MHz) d 153.2, 153.0, 143.9, 138.0, 137.9, 133.5, 131.6, 127.9, 125.9, 121.1, 113.8, 106.0, 60.9, 56.3, 56.1. HRMS (EI) M$^+$ calcd for C$_{18}$H$_{19}$NO$_6$ 345.1212, found 345.1229. Anal. Calcd for C$_{18}$H$_{19}$NO$_6$: C, 62.60; H, 5.55; N, 4.06. Found: C, 62.68; H, 5.58; N, 4.05.

Compound 27E showed inhibition of tubulin polymerization with an IC$_{50}$>40 μM and biological activity as seen in Table 35.

TABLE 35

Human Cancer Cell Line Studies (Compound 27E)

| Cell Type | Cell Line | GI$_{50}$ (μg/ml) |
|---|---|---|
| Pancreas adn | BXPC-3 | 1.9 |
| Neuroblast | SK-N-SH | 2.1 |
| Thyroid ca | SW1736 | 3.3 |
| Lung-NSC | NCI-H460 | 2.3 |
| Pharynx-sqam | FADU | 1.1 |
| Prostate | DU-145 | 2.6 |

Purification and characterization of (E) isomer, compound 28E, was done as follows. Purification by flash chromatography (silica gel, 70:30 hexanes:ethyl acetate) afforded (E)-ethene 28E (0.274 g, 0.793 mmol, 28%) as a bright yellow solid. Recrystallization (hexanes/CH$_2$Cl$_2$) gave an analytically pure sample of (E)ethene 28E, mp=187–188° C. $^1$H-NMR (CDCL$_3$, 360 MHz) d 7.92 (d, J=8.6 Hz, 1H, ArH), 7.16 (m, 2H, ArH), 7.15 (d, J=16.4 Hz, 1H, vinyl CH), 6.99 (d, J=16.4 Hz, 1H, vinyl CH), 6.77 (s, 2H, ArH), 4.03 (s, 3H, OCH$_3$), 3.93 (s, 6H, OCH$_3$), 3.89 (s, 3H, OCH$_3$); $^{13}$C-NMR (CDCL$_3$, 90 MHz) d 153.7, 153.5, 143.8, 138.9, 138.0, 132.9, 131.8, 126.6, 125.9, 117.9, 111.0, 104.1, 61.0, 56.5, 56.2. HRMS (EI) M$^+$ calcd for C$_{18}$H$_{19}$NO$_6$ 345.1212, found 345.1220. Anal. Calcd for C$_{18}$H$_{19}$NO$_6$: C, 62.60; H, 5.55; N, 4.06. Found: C, 62.51; H, 5.53; N, 3.95.

Figure 32:
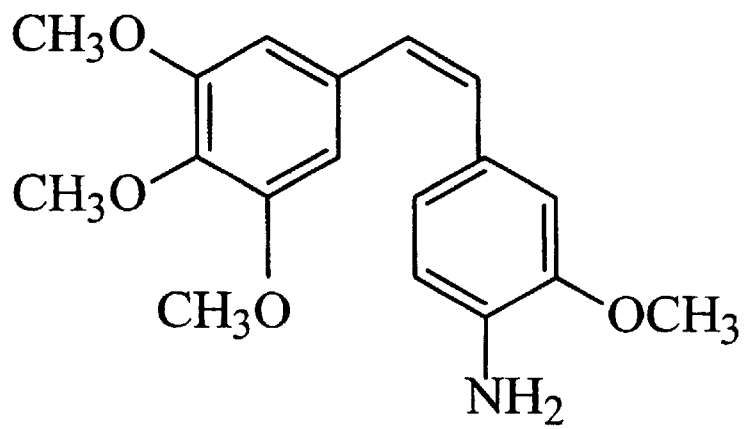
FIG. 32 shows compound 29E, (Z)-1-(4'amino-3'-methoxyphenyl)-2-(3",4",5"-trimethoxyphenyl)ethene

Compound 29E—(Z)-1-(4'amino-3'-methoxyphenyl)-2-(3",4",5"-trimethoxyphenyl)ethene (see FIG. 32), was prepared as follows.

(Z)-ethene 27E (0.454 g, 1.31 mmol) was dissolved in a mixture acetone (10 mL) and water (5 mL) and heated at 50°

C. After 30 min, $Na_2S_2O_4$ (4.57 g, 26.28 mmol) was added slowly. After 1 h of reflux at 50° C. the mixture was cooled to room temperature and water was added. The product was rinsed with $NaHCO_3$, and then it was isolated by extraction with ethyl acetate. The organic layer was dried over $Na_2SO_4$. The solvent was removed under reduced pressure, and the crude product (0.302 g, 0.956 mmol, 73%) obtained was also usable in azide formation.

Figure 33:
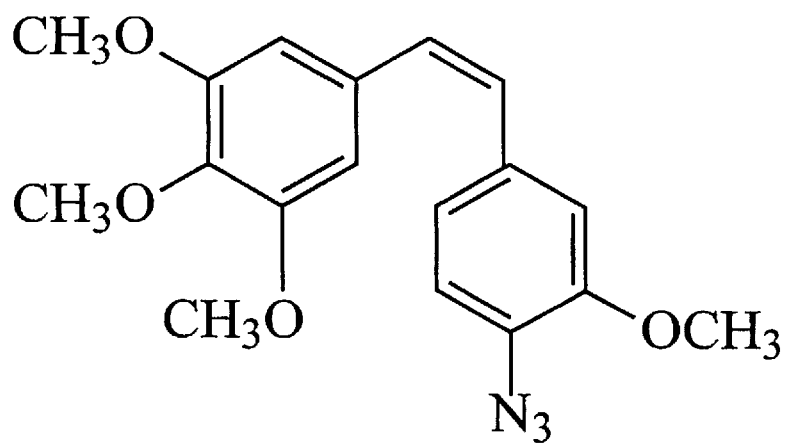
FIG. 33 shows compound 30E, (Z)-1-(4'azido-3'-methoxyphenyl)-2-(3",4",5"-trimethoxyphenyl)ethene

Compound 30E—(Z)-1-(4'azido-3'-methoxyphenyl)-2-(3",4",5"-trimethoxyphenyl)ethene (see FIG. 33) was prepared as follows.

(Z)-amino ethene 29E (0.166 g, 0.526 mmol) was dissolved in acetone (7.5 mL) in the dark, and cooled to 0° C., then HCl (0.22 M, 7.5 ml) was added. After 10 min of stirring under a nitrogen atmosphere, $NaNO_2$ (0.160 g, 2.31 mmol) was added. After 30 min, $NaN_3$ (0.427 g, 6.58 mmol) was added. After 15 min. at 0° C., dry ether (7.5 mL) was layered in. After 45 min, water was added and the product was isolated by extraction with ether. The organic layer was extracted with brine and dried over $MgSO_4$. The solvent was removed under reduced pressure and purified by flash chromatophy (silica gel, 70:30 hexanes:ethyl acetate). (Z)-compound 30E was obtained as a white solid (0.077 g, 0.226 mmol, 43%) with mp=61–63° C. $^1$H-NMR ($CDCl_3$, 360 MHz), d 6.89 (s, 2H, ArH), 6.81 (s, 1H, ArH), 6.54 (d, J=12.1 Hz, 1H, vinyl CH), 6.50 (s, 2H, ArH), 6.49 (d, J=12.1 Hz, 1H, vinyl CH), 3.83 (s, 3H, $OCH_3$), 3.71 (s, 6H, $OCH_3$), 3.67 (s, 3H, $OCH_3$). $^{13}$C-NMR ($CDCL_3$, 90 MHz) d 153.0, 151.3, 137.3, 134.7, 132.5, 130.2, 129.1, 127.1, 122.3, 119.8, 112.5, 105.9, 60.8, 55.9, 55.7. HRMS (EI) $M^+$ calcd for $C_{18}H_{19}N_3O_4$ 341.1376, found 341.1360. Anal. Calcd. for $C_{18}H_{19}N_3O_4$: C, 63.33; H, 5.62; N, 12.31. Found: C, 63.23; H, 5.62; N, 12.21.

Compound 30E showed inhibition of tubulin polymerization with an $IC_{50}$=1.5 µM. Certain biological activity of compound 30E, (Z)-1-(4'azido-3'-methoxyphenyl)-2-(3",4",5"-trimethoxyphenyl)ethene, is shown in Table 36.

TABLE 36

Human Cancer Cell Line Studies (Compound 30E)

| Cell Type | Cell Line | $GI_{50}$ (µg/ml) |
| --- | --- | --- |
| Pancreas adn | BXPC-3 | 0.30 |
| Neuroblast | SK-N-SH | 0.24 |
| Thyroid ca | SW1736 | 0.45 |
| Lung-NSC | NCI-H460 | 0.35 |
| Pharynx-sqam | FADU | 0.42 |
| Prostate | DU-145 | 0.70 |

Figure 34:
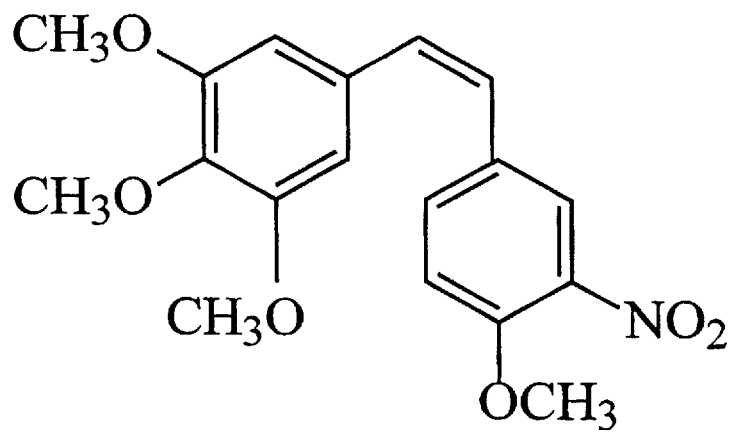
FIG. 34 shows compound 31E, (Z)-1-(4"-methoxy-3"-nitrophenyl)-2-(3',4',5'-trimethoxyphenyl)ethene
Figure 35:
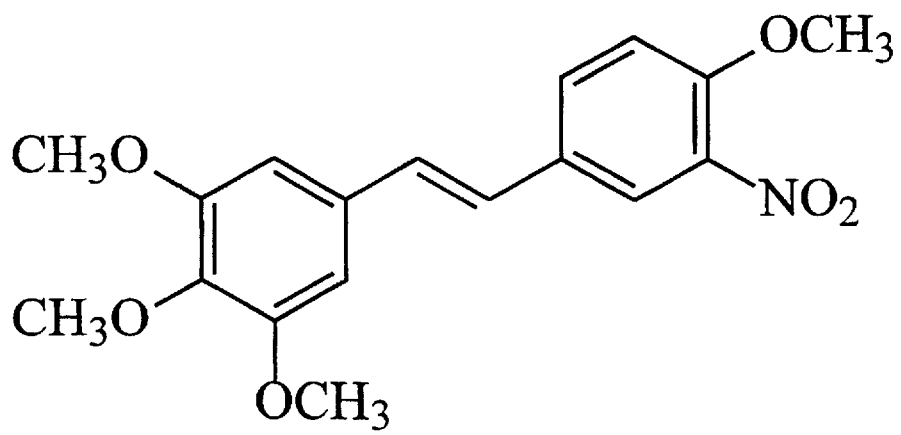
FIG. 35 shows compound 32E, (E)-1-(4"-methoxy-3"-nitrophenyl)-2-(3',4',5'-trimethoxyphenyl)ethene

Compounds 31E and 32E—(E/Z)-1-(4"-methoxy-3"-nitrophenyl)-2-(3',4',5'-trimethoxyphenyl)ethene (see FIG. 34 and FIG. 35), isomeric compounds, were prepared as follows.

3,4,5-Trimethoxybenzaldehyde (1.17 g, 5.98 mmol) and 3-methoxy-4-nitrobenzyltriphenylphosphonium bromide 6 (3.01 g, 5.92 mmol) were dissolved in $CH_2Cl_2$ (40 mL) and stirred under a nitrogen atmosphere. After 30 min, NaH (0.710 g, 29.6 mmol) was added. After 14 h, water was added carefully and the product was isolated by extraction with $CH_2Cl_2$. The organic phase was washed with brine and dried over $MgSO_4$ to afford a mixture of ethenes compound 32E and 31E (Z/E: 2.9/1.0).

Purification and characterization of (Z)-ethene (compound 31E) was done as follows. Purification by flash chromatography (silica gel, 70:30 hexanes:ethyl acetate) afforded (Z)-ethene 31E (1.44 g, 4.16 mmol, 73%) as a light yellow solid. Recrystallyzation (hexanes/$CH_2Cl_2$) afforded an analytically pure sample of ethene 31E, mp=119–121° C. $^1$H-NMR ($CDCl_3$, 360 MHz) d 7.80 (d, J=2.2 Hz, 1H, Ar), 7.43 (dd, J=8.6, 2.2 Hz, 1H, Ar), 6.94 (d, J=8.6 Hz, 1H, ArH), 6.58 (d, J=12.2 Hz, 1H, vinyl CH), 6.45 (d, J=13.3 Hz, 1H, vinyl CH), 6.47 (s, 2H, ArH), 3.94 (s,3H, $OCH_3$), 3.85 (s, 3H, $OCH_3$), 3.72 (s, 6H, $OCH_3$); $^{13}$C-NMR ($CDCL_3$, 90MHz) d 153.2, 151.7, 139.5, 137.7, 134.6, 131.8, 131.3, 129.7, 126.8, 125.9, 113.1, 105.9, 60.9, 56.5, 56.0. HRMS (EI) $M^+$ calcd for $C_{18}H_{19}NO_6$ 345.1212, found 345.1191. Anal. Calcd for $C_{18}H_{19}NO_6$: C, 62.60; H, 5.55; N, 4.06. Found: C, 62.53; H, 5.61; N, 3.97.

Compound 31E, (Z)-1-(4"-methoxy-3"-nitrophenyl)-2-(3',4',5'-trimethoxyphenyl)ethene, showed certain biological activity as seen in Tables 37 and 38.

TABLE 37

P388 Leukemia Data (Compound 31E)

| Cell Type | Cell Line | $ED_{50}$ (µg/ml) |
| --- | --- | --- |
| Mouse Leukemia | P388 | 4.0 |

TABLE 38

Human Cancer Cell Line Studies (Compound 31E)

| Cell Type | Cell Line | $GI_{50}$ (µg/ml) |
| --- | --- | --- |
| Pancreas adn | BXPC-3 | 0.037 |
| Neuroblast | SK-N-SH | >10 |
| Thyroid ca | SW1736 | 0.056 |
| Lung-NSC | NCI-H460 | 0.043 |
| Pharynx-sqam | FADU | 2.6 |
| Prostate | DU-145 | 0.046 |

Purification and characterization of (E)-ethene 32E was done as follows. Purification by flash chromatography (silica gel, 70:30 hexanes:ethyl acetate) afforded ethene 32E (0.541 g, 1.57 mmol, 27%) as a bright yellow solid. Recrystalyzation (hexanes/$CH_2Cl_2$) afforded an analytically pure sample, mp=147–148° C. $^1$H-NMR ($CDCl_3$, 360 MHz) d 8.01 (d, J=2.2 Hz, 1H, ArH), 7.65 (dd, J=8.7, 2.3 Hz, 1H, ArH), 7.15 (d, J=8.7 Hz, 1H, ArH), 7.00 (d, J=16.2 Hz, 1H, vinyl CH), 6.93 (d, J=16.2 Hz, 1H, vinyl CH), 6.73 (s, 2H, ArH), 3.99 (s, 3H, $OCH_3$), 3.92 (s, 6H, $OCH_3$), 3.88 (s, 3H, $OCH_3$); $^{13}$C-NMR ($CDCl_3$, 90 MHz) d 153.5, 150.2, 140.0, 138.5, 132.4, 131.8, 130.4, 129.6, 125.2, 123.1, 113.8, 103.8, 61.0, 56.7, 56.2. HRMS (EI) $M^+$ calcd for $C_{18}H_{19}NO_6$ 345.1212, found 345.1206. Anal. Calcd for $C_{18}H_{19}NO_6$: C, 62.60; H, 5.55; N, 4.06. Found: C, 62.60; H, 5.60; N, 3.97.

Figure 36:
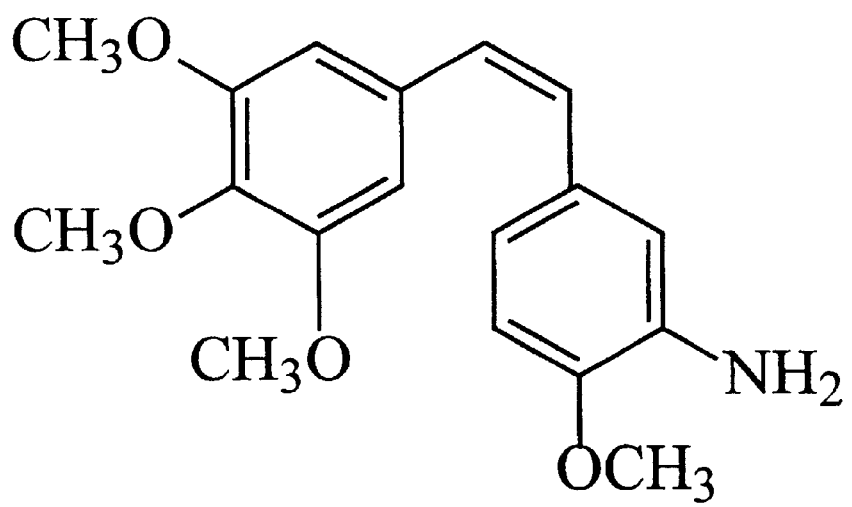
FIG. 36 shows compound 33E, (Z)-1-(3'-amino-4'-methoxyphenyl)-2-(3",4",5"-trimethoxyphenyl)ethene

Compound 33E—(Z)-1-(3'-amino-4'-methoxyphenyl)-2-(3",4",5"-trimethoxyphenyl)ethene (see FIG. 36) was prepared as follows.

Ethene 31E (1.24 g, 3.58 mmol) was dissolved in a mixture of acetone (40 mL) and water (20 mL) and heated at 50° C. After 30 min, $Na_2S_2O_4$ (12.47 g, 71.61 mmol) was added slowly. After 30 min of reflux at 50° C. the mixture was cooled to room temperature and water was added. The product was isolated by extraction with ethyl acetate. The organic layer was dried over $Na_2SO_4$. The solvent was removed under reduced pressure and the product was purified by flash chromatography (70:30, hexanes:ethyl acetate) to afford a pure sample of arylamine (0.423 g, 1.34 mmol, 37%) 33E, mp=64–66° C. $^1$H-NMR ($CDCL_3$, 360 MHz) d 6.71 (s, 1H, ArH), 6.68 (s, 2H, ArH), 6.55 (s, 2H, ArH), 6.46 (d, J=12.2 Hz, 1H, vinyl CH), 6.37 (d, J=12.0 Hz, 1H, vinyl CH), 3.84 (s, 3H, OCH$_3$), 3.83 (s, 3H, OCH$_3$), 3.71 (s, 6H, OCH$_3$); $^{13}$C-NMR (CDCl$_3$, 90 MHz) d 152.9, 146.7, 137.2, 135.8, 133.0, 130.2, 130.0, 128.4, 119.5, 115.3, 110.1, 106.2, 60.9, 56.0, 55.5. HRMS (EI) M$^+$ calcd for C$_{18}$H$_{21}$NO$_4$ 315.1471, found 315.1466

Compound 33E showed inhibition of tubulin polymerization with an IC$_{50}$=1.7 μM. Compound 33E, (Z)-1-(3'-amino-4'-methoxyphenyl)-2-(3",4",5"-trimethoxyphenyl)ethene, had certain biological activity as shown in Table 39.

TABLE 39

Human Cancer Cell Line Studies (Compound 33E)

| Cell Type | Cell Line | GI$_{50}$ (μg/ml) |
|---|---|---|
| Pancreas adn | BXPC-3 | 0.0013 |
| Neuroblast | SK-N-SH | <0.0010 |
| Thyroid ca | SW1736 | <0.0010 |
| Lung-NSC | NCI-H460 | 0.00068 |
| Pharynx-sqam | FADU | <0.0010 |
| Prostate | DU-145 | 0.00096 |

Figure 37:
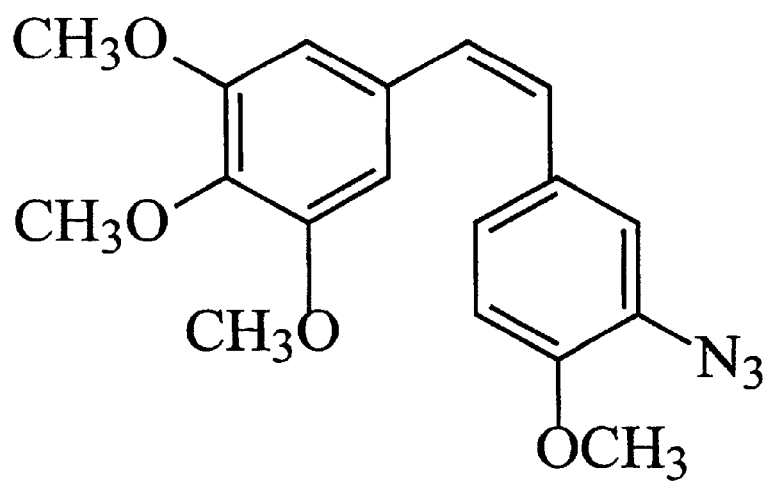
FIG. 37 shows compound 34E, (Z)-1-(3'azido-4'-methoxyphenyl)-2-(3",4",5"-trimethoxyphenyl)ethene

Compound 34E—(Z)-1-(3'azido-4'-methoxyphenyl)-2-(3",4",5"-trimethoxyphenyl)ethene (see FIG. 37) was prepared as follows.

(Z)-amino ethene 33E (0.327 g, 1.04 mmol) was dissolved in acetone (15 mL) and cooled to 0° C., then HCl (0.22 M, 15 mL) was added. After 10 min of stirring under a nitrogen atmosphere, the NaNO$_2$ (0.316 g, 4.58 mmol) was added. After 30 min, NaN$_3$ (0.852 g, 13.10 mmol) was added. After 15 min. at 0° C., dry ether (17 mL) was layered in. After 45 min of stirring the mixture was extracted with brine, the product was dried over MgSO$_4$. The solvent was removed under reduced pressure and purified by flash column chromatography (70:30 hexanes:ethyl acetate). The product obtained was a yellow oil (0.163 g, 0.478 mmol, 46%). 1H-NMR (CDCL$_3$, 360 MHz) d 7.03 (dd, J=8.4 Hz, 2.1 Hz, 1H, ArH), 6.97 (d, J=2.1 Hz, 1H, ArH), 6.76 (d, J=8.4 Hz, 1H, ArH), 6.49 (s, 2H, ArH), 6.49 (d, J=11.9 Hz, 1H, vinyl CH), 6.43 (d, J=12.2 Hz, 1H, vinyl CH), 3.84 (s, 6H, OCH$_3$), 3.71 (s, 6H, OCH$_3$); $^{13}$C-NMR (CDCl$_3$, 90 MHz) d 152.9, 150.7, 137.3, 132.4, 130.3, 129.6, 128.3, 127.8, 126.5, 120.4, 111.5, 105.8, 60.8, 55.8. Anal. Calcd for C$_{18}$H$_{19}$N$_3$:O$_4$: C, 63.33; H, 5.61 N, 12.31. Found: C, 63.38; H, 5.64; N, 12.28.

Compound 34E, (Z)-1-(3'azido-4'-methoxyphenyl)-2-(3",4",5"-trimethoxyphenyl)ethene, had certain biological activity as shown in Tables 40 and 41. Compound 34E showed inhibition of tubulin polymerization with an IC$_{50}$=1.3 μM.

TABLE 40

P388 Leukemia Data (Compound 34E)

| Cell Type | Cell Line | ED$_{50}$ (μg/ml) |
|---|---|---|
| Mouse Leukemia | P388 | 0.0384 |

TABLE 41

Human Cancer Cell Line Studies (Compound 34E)

| Cell Type | Cell Line | GI$_{50}$ (μg/ml) |
|---|---|---|
| Pancreas adn | BXPC-3 | 0.0050 |
| Neuroblast | SK-N-SH | 0.0033 |
| Thyroid ca | SW1736 | 1.2 |

TABLE 41-continued

Human Cancer Cell Line Studies (Compound 34E)

| Cell Type | Cell Line | GI$_{50}$ (μg/ml) |
|---|---|---|
| Lung-NSC | NCI-H460 | 0.0056 |
| Pharynx-sqam | FADU | 0.0076 |
| Prostate | DU-145 | 0.0091 |

Functionalization of the nitrogen analogs of combretastatin is as follows. The amino analogs of combretastatin described in this application may be suitably modified through amide linkages to incorporate short peptide oligomers. The new compounds prepared in this fashion may have improved bioavailability (especially in terms of water solubility) and enhanced molecular recognition for the selective colchicine binding site on β-tubulin. A wide variety of amino acid residues may be attached to the nitrogen atom in an analogous fashion. A typical experimental procedure (in this case for the attachment of a serine residue) is described below.

To a well-stirred solution of serine and amino-combretastatin in diethyl ether was added diisopropylcarbodiimide (DIC). After stirring for 12 hours, the solvent was removed under reduced pressure and the amide product was purified by flash chromatography and recrystallization.

It should be clear to anyone skilled in the art that this general procedure may be employed to prepare amides incorporating many amino acid residues (both naturally occurring and synthetic) and may be used to prepare short, medium, or large oligomers.

In addition, functionalization of the amino analogs of combretastatin to include the taxol side-chain through an amide linkage may result in combretastatin-taxol hybrid drugs of enhanced cytotoxicity and selectivity. The taxol side chain may be incorporated through direct reaction with the ojima β-lactam (Ojima et al., Nicolaou et al.).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bai, Schwartz, Kepler, Pettit and Hamel, *Cancer Res.*, 56:4398–4406, 1996.

Black and Clemens, U.S. Pat. No. 4,656,187

Boger and Curran, *J. Org. Chem.*, 57:2235, 1992.

Cameron et al., WO 95/10513.

Carlson et al., U.S. Pat. No. 5,532,382.

Chan and Gong, *Science,* 249:924–926, 1990.
Chavan, Richardson, Kim, Haley, Watt, Forskolin, *Bioconjugate Chem.,* 4:268, 1993.
Cushman et al., U.S. Pat. No. 5,430,062
Cushman, He, Katzenellenbogen, Varma, Hamel, Lin, Ram, Sachdeva, *J. Med. Chem.,* 40:2323, 1997.
Cushman, Katzenellenbogen, Lin, Hamel, *J. Med. Chem.,* 38:2041, 1995.
Cushman, Nagarathnam, Gopal, Chakraborti, Lin, Hamel, *J. Med. Chem.,* 34:2579, 1991.
D'Amato, Lin, Flynn, Folkman, Hamel, *Proc. Natl. Acad. Sci. USA,* 91:3964, 1994.
De Castro, *Acta. Trop.,* 53:83–98, 1993.
De Souza, *Internat. Rev. Cytol.,* 86:197–275, 1984.
Eaton, Gold, Zichi, *Chemistry and Biology,* 2: 633–638, 1995.
Floyd, Barnes, Williams, *Biochemistry,* 28:8515, 1989.
Gerwick, Proteau, Nagle, Hamel, Blokhin, Slate, *J. Org. Chem.,* 59:1243, 1994.
Hahn, Hastie, Sundberg, *Photochem. Photobiol.,* 55:17, 1992.
Hamel, *Medicinal Research Reviews,* 16:207, 1996.
Hamel, Lin, Flynn, D'Amato, *Biochemistry,* 35:1304, 1996.
Hamel and Lin, *Biochemistry,* 23:4173, 1984.
Jiang, Hesson, Dusak, Dexter, Kang, Hamel, *J. Med. Chem.,* 33:1721, 1990.
Jones and Suarez, U.S. Pat. No. 4,133,814.
Jones, Jevnikar, Pike, Peters, Black, Thompson, Falcone, Clemens, *J. Med. Chem.,* 27:1057, 1984.
Jones, Suarez, Massey, Black, Tinsley, *J. Med. Chem.,* 22:962, 1979.
Kang, Getohun, Muzaffar, Brossi, Hamel, *J. Biol. Chem.,* 265, 10255, 1990.
Katiyar, Gordon, McLaughlin, Edlind, *Antimicrob. Agents Chemother.,* 38:2086–2090, 1994.
Kingston, Samaranayake, Ivey, *J. Nat. Prod.,* 53:1, 1990.
Kobayashi, Nakada, Ohno, *Indian J. Chem.,* 32B:159, 1993.
Kobayashi, Nakada, Ohno, *Pure Appl. Chem.,* 64:1121, 1992.
Kost, Budylin, Matveeva and Sterligov, *Zh. Org Khim,* 6:1503, 1970.
Kym, Anstead, Pinney, Wilson, Katzenellenbogen, *J. Med. Chem.,* 36:3910, 1993.
Laitman, *TDR News,* 30:5, 1989.
Lavielle, Havtefaye, Schaeffer, Boutin, Cudennec, Pierre, *J. Med. Chem.,* 34:1998, 1991.
Lin, Ho, Pettit, Hamel, *Biochemistry,* 28:6984, 1989.
Maldonado, Molina, Payeres and Urbina, *Antimicrobial Agents and Chemotherapy,* 37:1353–1359, 1993.
Marr and Docamp, *Rev. Infect. Dis.,* 8:884–903, 1986.
Monks, Scudiero, Skehan, Shoemaker, Pauli, Vistica, Hose, Langley, Cronise, Vaigro-Wolff, Gray-Goodrich, Campbell, Mayo, and Boyd, *J. Nat. Cancer Inst.,* 83:757–766, 1991.
Mouridsen, Palshof, Patterson and Battersby, *Cancer Treat. Rev.,* 5:131, 1978.
Mullica, Pinney, Dingeman, Bounds, Sappenfield, *J. Chem. Cryst.,* 26:801–806, 1996.
Mullica, Pinney, Mocharla, Dingeman, Bounds, Sappenfield, *J. Chem. Cryst.,* 1997, (Accepted, In Press).
Muzaffar, Brossi, Lin, Hamel, *J. Med. Chem.,* 33:567, 1990.
Nakada, Kobayashi, Iwasaki, Ohno, *Tetrahedron Lett.,* 34:1035, 1993.
Nicolaou, Yang, Liu, Ueno, Nantermet, Guy, Claiborne, Renaud, Couladouros, Paulvannan, Sorensen, *Nature,* 367:630, 1994.
Ojima, Habus, Zhao, Zucco, Park, Sun, Brigaud, *Tetrahedron,* 48:6985, 1992.
Owellen, Hartke, Kickerson, Hains, *Cancer Res.,* 36:1499, 1976.
Parness and Horwitz, J. Cell Biol., 91:479, 1981.
Pettit et al., U.S. Pat. No. 4,940,726
Pettit et al., U.S. Pat. No. 4,996,237
Pettit et al., U.S. Pat. No. 5,409,953
Pettit, Cragg, Herald, Schmidt, Lohavanijaya, *Can. J. Chem.,* 60:1374, 1982.
Pettit, Cragg, Singh, *J. Nat. Prod.,* 50:386, 1987.
Pettit, Singh, Cragg, *J. Org. Chem.,* 50:3404, 1985.
Pettit, U.S. Pat. No. 5,561,122
Pinney and Katzenellenbogen, *J. Org. Chem.,* 56:3125, 1991.
Pinney, Carlson, Katzenellenbogen, Katzenellenbogen, *Biochemistry,* 30:2421, 1991.
Pinney, Dingeman, Bounds, Mocharla, Pettit, Hamel, *J. Org. Chem.,* 1998, (Submitted).
Prata, *Infect. Dis. Clin. North. Amer.,* 8:61–76, 1994.
Rao, Bhanu, Sharma, *Tetrahedron Lett.* 34:707, 1993.
Rao, Horwitz, Ringel, *J. Natl. Cancer Inst.,* 84:785, 1992.
Rao, Krauss, Heerding, Swindell, Ringel, Orr, Horwitz, *J. Biol. Chem.,* 269:3132, 1994.
Rao, Sharma, Bhanu, *Tetrahedron Lett.* 33:3907, 1992.
Safa, Hamel, Felsted, *Biochemistry,* 26:97, 1987.
Sawada, Hashimoto, Li, Kobayashi, Iwasaki, *Biochem. Biophys. Res. Commun.,* 178:558, 1991.
Sawada, Kato, Kobayashi, Hashimoto, Watanabe, Sugiyama, Iwasaki, *Bioconjugate Chem.,* 4:284, 1993.
Sawada, Kobayashi, Hashimoto, Iwasaki, *Biochem Pharmacol.,* 45:1387, 1993.
Schiff, Fant, Horwitz, *Nature,* 277:665, 1979.
Shirai, Tokuda, Koiso, Iwasaki, *Biomedical Chem. Lett.,* 699, 1994.
Staretz and Hastie, *J. Org. Chem.,* 58:1589, 1993.
Swindell, Heerding, Krauss, Horwitz, Rao, Ringel, *J. Med. Chem.,* 37:1446, 1994.
Swindell, Krauss, Horwitz, Ringel, *J. Med. Chem.,* 34:1176, 1991.
Williams, Mumford, Williams, Floyd, Aivaliotis, Martinez, Robinson, Barnes, *J. Biol. Chem.,* 260:13794, 1985.
Wolff, Knipling, Cahnmann, Palumbo, *Proc. Natl. Acad. Sci. USA,* 88:2820, 1991.
World Health Organization, Tropical disease research progress, 1991–1992.

What is claimed is:

1. A compound of the structure:

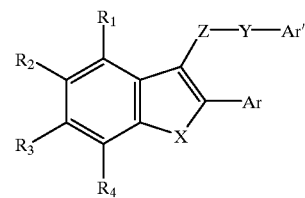

wherein

X is S, $R_1$–$R_4$ are independently chosen from the group consisting of H, OH and $C_1$–$C_5$ alkoxy, Z is chosen from the group consisting of C=O, $CH_2$, $C_2H_2$, CHOH, and $CHOCH_3$, Y is chosen from the group consisting of a covalent bond, $CH_2$, and $CH_2CH_2$, and Ar and Ar' are aryl moieties chosen from the group consisting of phenyl and napthyl, further substituted with at least one $C_1$–$C_5$, alkoxy group, at least one of which has at least two $C_1$–$C_5$ alkoxy groups, wherein when Ar is 3,4,5-trimethoxyphenyl, Z is C=O, Y is a covalent bond, $R_3$ is methoxy, $R_1$, $R_2$ and $R_4$ are H, and Ar is substituted with a methoxy group.

2. The compound of claim 1, wherein Z is C=O.

3. The compound of claim 1 wherein Ar' is chosen from the group consisting of 3,4,5-trimethoxyphenyl, 3,4-dimethoxyphenyl, 3,4 diethoxyphenyl and 3,4,5-triethoxyphenyl.

4. The compound of claim 1 wherein Ar is 4-methoxyphenyl.

5. The compound of claim 1 wherein $R_3$ is $OCH_3$.

6. A compound of the structure:

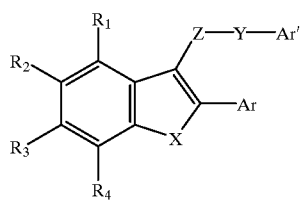

wherein $R_1$–$R_4$ are independently chosen from the group consisting of H, OH and $C_1$–$C_5$ alkoxy, Z is C=O, Y is chosen from the group consisting of a covalent bond, $CH_2$, and $CH_2CH_2$, Ar is a phenyl group with at least one $C_1$–$C_5$ alkoxy group and Ar' is a phenyl group with at least two $C_1$–$C_5$ alkoxy groups, wherein when Ar' is 3,4,5-trimethoxyphenyl Z is C=O, Y is a covalent bond, $R_3$ is methoxy and $R_1$, $R_2$ and $R_4$ are H, and Ar is substituted with a methoxy group.

7. The compound of claim 6 wherein Ar' is chosen from the group consisting of 3,4,5-trimethoxyphenyl, 3,4-dimethoxyphenyl, 3,4 diethoxyphenyl and 3,4,5-triethoxyphenyl.

8. The compound of claim 6 wherein Y is a covalent bond.

9. The compound of claim 6 wherein Ar is 4-methoxyphenyl.

10. The compound of claim 6 selected from the group containing 3-(3',4'-dimethoxybenzoyl)-2-(4'-methoxyphenyl)-6-methoxybenzol[b]-thiophene, and 3-[3', 4',5'-triethoxy-benzoyl)-2-(4'-methoxyphenyl)-6-methoxybenzo[b]-thiophene, and 3-[3'-(3",4",5"-trimethoxyphenyl)propanoyl]-2-(4'methoxyphenyl)-6-methoxybenzo[b] thiophene.

11. A compound of the structure

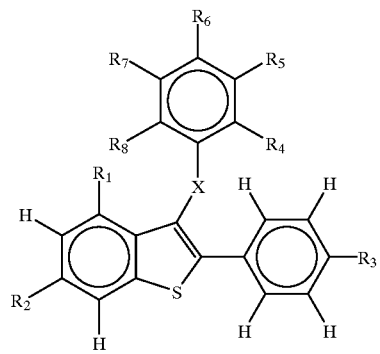

where $R_1$ is H or $CH_3O$;
$R_2$ is H, $CH_3O$ or $C_2H_5O$;
$R_3$ is $CH_3O$ of $C_2H_5O$;
$R_4$, $R_5$, $R_7$ and $R_8$ are independently H, $CH_3O$, $C_2H_5O$, or F;
$R_6$ is H, $CH_3O$, $C_2H_5O$, OH, F or $N(CH_3)_2$; wherein at least one of $R_4$, $R_5$, $R_6$, $R_7$ or $R_8$ is F or $N(CH_3)_2$; and X is

12. A compound of the structure

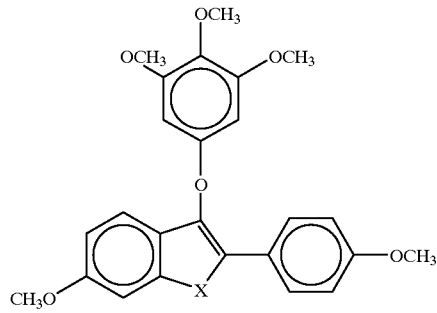

where X is S or S=O.

13. A compound of the structure

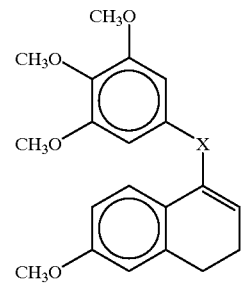

where X is CHOH or C=O.

* * * * *

UNITED STATES PATENT AND TRADEMARK OFFICE
CERTIFICATE OF CORRECTION

| | | |
|---|---|---|
| PATENT NO. | : 6,162,930 | Page 1 of 1 |
| DATED | : December 19, 2000 | |
| INVENTOR(S) | : Pinney et al. | |

It is certified that error appears in the above-identified patent and that said Letters Patent is hereby corrected as shown below:

Claims,
Column 39, claim 1,
Line 5, delete "Ar" and substitute therefor -- Ar' --.

Column 39, claim 6,
Delete "X" of the compound structure and substitute therefor -- S --.

Signed and Sealed this

Twenty-third Day of October, 2001

Attest:

NICHOLAS P. GODICI
Attesting Officer  Acting Director of the United States Patent and Trademark Office